US012558458B2

(12) United States Patent
Myung et al.

(10) Patent No.: US 12,558,458 B2
(45) Date of Patent: Feb. 24, 2026

(54) TARGETED IN SITU THERAPEUTIC DELIVERY OF SECRETED FACTORS FROM STEM CELLS FOR TREATMENT OF DAMAGED TISSUE

(71) Applicants: The Board of Trustees of the Leland Stanford Junior University, Stanford, CA (US); The United States Government as represented by the Department of Veterans Affairs, Washington, DC (US); The Board of Trustees of the University of Illinois, Urbana, IL (US)

(72) Inventors: David Myung, Menlo Park, CA (US); Gabriella Fernandes-Cunha, Redwood City, CA (US); Hyun Jong Lee, Redwood City, CA (US); Ali Djalilian, Redwood City, CA (US)

(73) Assignees: The Board of Trustees of the Leland Stanford Junior University, Stanford, CA (US); The United States Government as Represented by the Department of Veteran Affairs, Washington, DC (US); The Board of Trustees of the University of Illinois, Urbana, IL (US)

( * ) Notice: Subject to any disclaimer, the term of this patent is extended or adjusted under 35 U.S.C. 154(b) by 378 days.

(21) Appl. No.: 16/614,205

(22) PCT Filed: May 18, 2018

(86) PCT No.: PCT/US2018/033528
§ 371 (c)(1),
(2) Date: Nov. 15, 2019

(87) PCT Pub. No.: WO2018/213795
PCT Pub. Date: Nov. 22, 2018

(65) Prior Publication Data
US 2022/0088274 A1 Mar. 24, 2022

Related U.S. Application Data

(60) Provisional application No. 62/625,853, filed on Feb. 2, 2018, provisional application No. 62/508,260, filed on May 18, 2017.

(51) Int. Cl.
| A61L 27/52 | (2006.01) |
| A61K 35/28 | (2015.01) |
| A61K 35/51 | (2015.01) |
| A61K 35/545 | (2015.01) |
| A61L 27/36 | (2006.01) |
| A61L 27/54 | (2006.01) |

(52) U.S. Cl.
CPC .............. *A61L 27/52* (2013.01); *A61K 35/28* (2013.01); *A61K 35/51* (2013.01); *A61K 35/545* (2013.01); *A61L 27/36* (2013.01); *A61L 27/54* (2013.01); *A61L 2300/414* (2013.01); *A61L 2300/426* (2013.01); *A61L 2300/43* (2013.01)

(58) Field of Classification Search
CPC .......... A61L 27/52; A61L 27/36; A61L 27/54; A61L 2300/414; A61L 2300/426; A61L 2300/43; A61K 35/28; A61K 35/51; A61K 35/545
See application file for complete search history.

(56) References Cited

U.S. PATENT DOCUMENTS

| 5,705,485 | A | 1/1998 | Cini et al. |
| 11,213,569 | B2 * | 1/2022 | Hamed ................... A61K 9/06 |
| 2009/0306707 | A1 | 12/2009 | Brownlee et al. |
| 2010/0080840 | A1 | 4/2010 | Cho et al. |
| 2010/0291171 | A1 | 11/2010 | Crescenzi et al. |
| 2015/0112244 | A1 | 4/2015 | Horn-Ranney et al. |
| 2016/0051724 | A1 | 2/2016 | Sahin et al. |
| 2016/0144069 | A1 | 5/2016 | Cho et al. |
| 2016/0228610 | A1 | 8/2016 | Lai et al. |
| 2016/0289219 | A1 | 10/2016 | Song et al. |
| 2020/0038484 | A1 * | 2/2020 | Myung ............. A61K 47/6435 |

FOREIGN PATENT DOCUMENTS

| CN | 103848928 | A | 6/2014 | |
| WO | WO2012/053976 | | 4/2012 | |
| WO | WO-2012053976 | A1 * | 4/2012 | ............. A61K 35/28 |
| WO | 2014039012 | A1 | 3/2014 | |
| WO | WO-2015154078 | A1 * | 10/2015 | ............. A61L 27/20 |
| WO | 2017037655 | A1 | 3/2017 | |
| WO | 2017041133 | A1 | 3/2017 | |
| WO | 2017132639 | A1 | 8/2017 | |

OTHER PUBLICATIONS

Peng, Y., et al., "Freeze-dried rat bone marrow mesenchymal stem cell paracrine factors: a simplified novel material for skin wound therapy," Tissue Engineering Part A 21 (5-6): 1036-46. doi: 10.1089/ten.TEA.2014.01022015 Mar. Epub Dec. 11, 2014. (Year: 2014).*
Bakota, E., et al., "Injectable multidomain peptide nanofiber hydrogel as a delivery agent for stem cell secretome," Biomacromolecules 12(5): 1651-7 doi: 10.1021/bm200035r. Epub Apr. 13, 2011. (2011)). (Year: 2011).*
Miyakoshi, N., et al., "Effects of intraarticular administration of basic fibroblast growth factor with hyaluronic acid on osteochondral defects of the knee in rabbits," Archives of Orthopaedic and Trauma Surgery 125(10): 683-92 doi: 10.1007/s00402-005-0052-y (2005), Epub Sep. 28, 2005) (Year: 2005).*
(Continued)

*Primary Examiner* — Tracy Vivlemore
*Assistant Examiner* — Eric J Rogers
(74) *Attorney, Agent, or Firm* — Pamela J. Sherwood; Bozicevic, Field & Francis LLP

(57) ABSTRACT
Compositions and methods for repairing or regenerating damaged tissue are disclosed. In particular, the invention relates to methods of delivering secreted factors from stem cells to tissues in order to immobilize and concentrate such secreted factors at or under the surface of damaged tissue to promote tissue regeneration.

11 Claims, 37 Drawing Sheets

(56)         References Cited

OTHER PUBLICATIONS

Vizoso, F., et al., "Mesenchymal Stem Cell Secretome: Toward Cell-Free Therapeutic Strategies in Regenerative Medicine," International Journal of Molecular Sciences 18(9): 1852. doi: 10.3390/ijms18091852. Aug. 25, 2017 (Year: 2017).*

Little, C., et al., "The Effect of Chondroitin Sulphate and Hyaluronic Acid on Chondrocytes Cultured within a Fibrin-Alginate Hydrogel," Journal of Functional Biomaterials 5(3): 197-210. doi: 10.3390/jfb5030197. Sep. 18, 2014 (Year: 2014).*

Wu, X., et al., "Retinal Degeneration: Molecular Mechanisms and Therapeutic Strategies," Current Medicinal Chemistry 29(40): 6125-6140. doi: 10.2174/0929867328666211129122908. (Year: 2022).*

Gupta, D., Chen, P. P., "Glaucoma," American Family Physician 93(8): 668-74. (Year: 2016).*

Ziaei, M., et al., "Wound healing in the eye: Therapeutic prospects," Advanced Drug Delivery Systems 126: 162-176. doi: 10.1016/j.addr.2018.01.006. (Year: 2018).*

Lisch, W., and Weiss, J. S., "Early and late clinical landmarks of corneal dystrophies," Exp Eye Res 198:108139. doi: 10.1016/j.exer.2020.108139. (Year: 2020).*

Ma, Y., et al., "Reconstruction of chemically burned rat corneal surface by bone marrow-derived human mesenchymal stem cells," Stem Cells 24(2): 315-321. doi: 10.1634/stemcells.2005-0046. (Year: 2005).*

Sharma et al. (2013) "Human Cartilage Repair with a Photoreactive Adhesive-Hydrogel Composite," Science Translation Medicine, vol. 5, Iss. 167, pp. 1-18.

Zhang et al. (2015) "A Review of Collagen Cross-Linking in Cornea and Sclera," Journal of Ophthalmology, vol. 2015, pp. 1-12.

Little et al. (2014) "The Effect of Chondroitin Sulphate and Hyaluronic Acid on Chondrocytes 53 Cultured within a Fibrin-Alginate Hydrogel," Journal of Functional Bioinformatics, vol. 5, pp. 197-210.

Erica L. Bakota et. al., (2011), "Injectable Multidomain Peptide Nanofiber Hydrogel as a Delivery Agent for Stem Cell Secretome", Biomacromolecules, vol. 12, No. 5, pp. 1651-1657.

Yan Peng et. al., (2015), "Freeze-Dried Rat Bone Marrow Mesenchymal Stem Cell Paracrine Factors: A Simplified Novel Material for Skin Wound Therapy" Tissue Engineering Part A, vol. 21, No. 5-6.

Naohisa Miyakoshi et. al., (2005), "Effects of intraarticular administration of basic fibroblast growth factor with hyaluronic acid on osteochondral defects of the knee in rabbits", Archives of Ortopaedic and Trauma Surgery, vol. 125, No. 10, pp. 683-692.

* cited by examiner

HA/CS + Secretome

No RFP & Light 0.01% RFP, UV 0.01% RFP, BL

TARGETED IN SITU THERAPEUTIC DELIVERY OF SECRETED FACTORS FROM STEM CELLS FOR TREATMENT OF DAMAGED TISSUE

STATEMENT REGARDING FEDERALLY SPONSORED RESEARCH OR DEVELOPMENT

This invention was made with government support under contracts EY028176 and EY026877 awarded by the National Institutes of Health and W81XWH-14-1-585 from the Department of Defense. The government has certain rights in the invention.

TECHNICAL FIELD

The present invention pertains generally to compositions and methods for repairing or regenerating damaged tissue. In particular, the invention relates to methods of delivering secreted factors from stem cells to tissues in order to immobilize and concentrate such secreted factors at or under the surface of damaged tissue to promote tissue regeneration.

BACKGROUND

The following discussion of the background art is intended to facilitate an understanding of the present invention only. The discussion is not an acknowledgement or admission that any of the material referred to is or was part of the common general knowledge as of the priority date of the application.

Tissue regeneration is a complex process involving the temporal and spatial interplay between cells and their extracellular milieu. It can be impaired by a variety of causes including infection, poor circulation, loss of critical cells and/or proteins, and a deficiency in normal neural signaling such as in neurotrophic ulcers (Suzuki et al. (2003) Prog. Retin. Eye Res. 22(2):113-133; Tran et al. (2004) Wound Repair and Regeneration 12(3):262-268). Moreover, uncontrolled wound responses can lead to scarring and contracture (Schultz et al. (2009) Wound Repair and Regeneration 17(2):153-162; Klenkler et al. (2007) The Ocular Surface 5(3):228-239). Ocular and peri-ocular anatomy is particularly vulnerable to severe morbidity, whether it be opacification of the cornea, residual deficits in cranial nerves, or cicatricial changes to the eyelids and adnexa.

Cell based therapies such as stem cell transplantation typically provide only cells without the required matrix upon which to grow, or without the stimulatory factors to which to respond by migration, proliferation, and/or differentiation. Topical approaches to wound healing have been reported using epidermal growth factor, thymosin beta 4, nerve growth factor, substance P and insulin-like growth factor, and fibronectin. However, a clinically proven biopharmacologic therapy has not yet been successfully developed.

Neurotrophic keratopathy (NK) is a degenerative disease of the cornea resulting from trigeminal nerve damage caused by a variety of conditions including diabetes, herpes, neoplasms, or trauma (Bonini et al. (2003) Eye 17(8):989-995; Dunn et al. (2010) Ann NY Acad Sci 1194(1):199-206). It is hallmarked by decreased corneal sensitivity, reduced reflex tearing, and poor wound healing, leaving the cornea susceptible to injury and progressive breakdown (Bonini et al., supra; Dunn et al., supra). NK poses a particularly difficult clinical challenge due to the limited efficacy of current treatments such as frequent lubrication, antibiotic drops or ointment, patching, and bandage contact lenses. In refractory cases, oral doxycycline, autologous serum, and application of an amniotic membrane, a flap of conjunctival tissue, or tarsorraphy are used alone or in combination (Abelson et al. (2014) Thoughts on Healing the Wounded Cornea, Review of Ophthalmology: 52-54). Amniotic membranes in particular have shown promising results, but wound closure times are still reported to be two weeks or greater (Kruse et al. (1999) Ophthalmology 106(8):1504-1511; Chen et al. (2000) Br. J. Ophthalmol. 84(8):826-833). Despite the arsenal of modalities available, a protracted clinical course is often required and the healing response can be erratic (Abelson et al., supra), leaving the cornea at risk of infection, scarring, perforation, and blindness (Abelson et al., supra; Nagano et al. (2003) Invest Ophthalmol. Vis. Sci. 44(9):3810-3815).

Corneal epithelial health is modulated by endogenous neuropeptides supplied by corneal nerves (Bonini et al. (2003) Eye 17(8):989-995). Promising yet limited results have been reported on the therapeutic potential of various topically applied neuropeptides and growth factors (Bonini et al., supra; Dunn et al., supra; Nagano et al., supra; Bonini et al. (2000) Ophthalmology 107(7):1347-1351). For instance, exogenous application of the neuropeptide Substance P (SP) has been shown to improve wound healing in NK, but its effects are enhanced when combined with another trophic agent such as epidermal growth factor (Guaiquil et al. (2014) Proc. Natl. Acad. Sci. USA 111(48): 17272-17277). Topical neuroregenerative ligands such as nerve growth factor (NGF) have been shown in clinical trials to restore corneal innervation (Aloe et al. (2008) Pharmacological Research 57(4):253-258; Guaiquil et al., supra), but treatment requires four times daily administration and anywhere from 9 days to 6 weeks for wound closure to occur (Aloe et al. (2012) J. Transl. Med. 10:239). Recently, vascular endothelial growth factor (VEGF) has been shown in an animal model to stimulate regeneration of injured corneal nerves (Guaiquil et al., supra), but these results have not yet been reported in humans. Thus, to date, a clinically available, rapid-onset biopharmacologic therapy for NK remains elusive.

Thus, there remains a need in the art for better ways to stimulate a regenerative response in order to foster wound healing and restore anatomy and, in turn, tissue functions such as epithelial barrier effects and neural transmission.

SUMMARY

The present invention relates to the use of biocompatible gel carriers to deliver secreted factors from stem cells to human tissue. Uncrosslinked biomaterial in a viscous gel may be used as a vehicle to deliver secreted factors from stem cells to damaged tissue. Alternatively, bioconjugation may be used for direct covalent linkage of the secreted factors from stem cells to damaged tissue. Bioconjugation may also be used to encapsulate secreted factors in a crosslinked hydrogel that covers the damaged tissue where release of the secreted factors promotes healing.

In one aspect, the invention includes a method of treating damaged tissue in a subject, the method comprising: a) collecting one or more secreted factors from a stem cell; b) mixing the one or more secreted factors from the stem cell with a solution comprising at least one biocompatible polymer or biopolymer to form a mixture; and c) applying the mixture to the damaged tissue, wherein the one or more secreted factors from the stem cell accelerate healing of the damaged tissue.

Biocompatible polymers and biopolymers (with or without modification) that may be used include glycoproteins, carbohydrates, and other macromolecules such as, but not limited to, various types of collagen, fibronectin, chitosan, laminin, hyaluronic acid, chondroitin sulfate, heparan sulfate, dermatan sulfate, chondroitin sulfate, methyl cellulose, hydroxy methyl cellulose, polyethylene glycol, polyvinyl pyrrolidone, and polyvinyl alcohol, or combinations thereof. In certain embodiments, hyaluronic acid, chondroitin sulfate, or a mixture of hyaluronic acid and chondroitin sulfate are used. The biocompatible polymers or biopolymers may be adherent or non-adherent to tissue. In one embodiment, the hyaluronic acid (HA) comprises a mixture of methacrylated HA (MA-HA) and thiolated HA (SH-HA) suitable for performing crosslinking by using a thiol-ene reaction.

In certain embodiments, at least one biocompatible polymer or biopolymer encapsulates one of the secreted factors, a subset of the secreted factors or all the secreted factors from the stem cell.

In certain embodiments, at least one biocompatible polymer or biopolymer forms a hydrogel encapsulating the one or more secreted factors from the stem cell.

In certain embodiments, a crosslinked gel carrier is used for delivery of the secreted factors from stem cells. In one embodiment, the invention includes a method of treating damaged tissue in a subject, the method comprising: a) collecting one or more secreted factors from a stem cell; b) mixing the one or more secreted factors from the stem cell with at least one hydrogel-forming molecule; and c) forming a hydrogel encapsulating the one or more secreted factors from the stem cell in situ over the damaged tissue by using a biocompatible bioconjugation method to crosslink said at least one hydrogel-forming molecule, wherein the hydrogel delivers the one or more secreted factors from the stem cell to the damaged tissue to accelerate healing of the damaged tissue. The hydrogel may be adherent or non-adherent to the tissue surface.

In other embodiments, an uncrosslinked gel carrier is used for delivery of the secreted factors from stem cells, wherein uncrosslinked macromolecules or biomacromolecules are mixed with stem cell secreted factors. In one embodiment, the invention includes a method of treating damaged tissue in a subject, the method comprising: a) collecting one or more secreted factors from a stem cell; b) mixing the one or more secreted factors from the stem cell with a solution comprising at least one biocompatible polymer or biopolymer to form a gel; and c) applying the gel to the damaged tissue.

In other embodiments, the gel carrier is non-covalently crosslinked (e.g. electrostatically or ionically crosslinked, or crosslinked by non-covalent interactions such as hydrogen bonds and Van Der Waals interactions) and is used for delivery of the secreted factors from stem cells, wherein non-covalently crosslinked macromolecules or biomacromolecules are mixed with the stem cell secreted factors. In one embodiment, the invention includes a method of treating damaged tissue in a subject, the method comprising: a) collecting one or more secreted factors from a stem cell; b) mixing the one or more secreted factors from the stem cell with a solution comprising at least one biocompatible polymer or biopolymer gel; and c) applying the gel to the damaged tissue, wherein a non-covalently crosslinked gel forms on the tissue.

The gel carrier may comprise, for example, glycoproteins, carbohydrates, and other macromolecules, including, but not limited to, various types of collagen, fibronectin, chitosan, laminin, hyaluronic acid, chondroitin sulfate, heparan sulfate, dermatan sulfate, chondroitin sulfate, methyl cellulose, hydroxy methyl cellulose, polyethylene glycol, polyvinyl pyrrolidone, and polyvinyl alcohol, or combinations thereof. In another embodiment, the gel carrier comprises linear hyaluronic acid, linear chondroitin sulfate, or a mixture of linear hyaluronic acid and linear chondroitin sulfate.

Damage to tissues may be caused, for example, by physical trauma, chemical injury, surgery, or a disease. In certain embodiments, the damaged tissue is ocular tissue (e.g., corneal tissue or stromal tissue). The methods of the invention may be used to treat damage to ocular tissue caused, for example, by a thermal burn, chemical burn, severe dry eye, keratoconjunctivitis sicca, Sjogren's syndrome, ocular graft-versus-host disease, ocular cicatricial pemphigoid (OCP), Stevens-Johnson syndrome, physical trauma, neurotrophic keratopathy, a recurrent corneal erosion, a corneal ulcer (infectious or non-infectious), corneal melt, exposure keratopathy, retinal disease, damage, or degeneration, or optic nerve damage or degeneration. In another embodiment, the method further comprising applying a bandage contact lens to the cornea.

Stem cell secretome may include extracellular vesicles (e.g., exosomes) containing secreted factors as cargo or vesicle-free secreted factors (e.g., solubilized secreted factors). The secreted factors from stem cells may include, but are not limited to, growth factors, cytokines, chemokines, anti-apoptotic factors, hormones, and extracellular matrix components (including but not limited to proteins, glycoproteins, glycosaminoglycans, or carbohydrates).

The stem cells that can be used in the practice of the invention may include, for example, embryonic stem cells, adult stem cells, bone marrow stem cells, umbilical cord stem cells, or induced pluripotent stem cells. In one embodiment, the stem cell is a human mesenchymal stem cell or a pluripotent stem cell.

In certain embodiments, at least one hydrogel-forming molecule is selected from the group consisting of a glycoprotein, a glycosaminoglycan, a carbohydrate, collagen, fibronectin, chitosan, laminin, hyaluronic acid, chondroitin sulfate, heparan sulfate, dermatan sulfate, chondroitin sulfate, methyl cellulose, hydroxy methyl cellulose, polyethylene glycol, polyvinyl pyrrolidone, and polyvinyl alcohol.

In certain embodiments, the hydrogel encapsulates a single secreted factor, a subset of the secreted factors or all the secreted factors from the stem cell. In certain embodiments, one or more secreted factors are contained within extracellular vesicles (e.g., exosomes). In another embodiment, all the secreted factors are contained within extracellular vesicles.

In certain embodiments, the biocompatible bioconjugation (crosslinking) method is a photochemical or non-photochemical bioconjugation method. In certain embodiments, a non-covalent crosslinking method is used, wherein crosslinking involves formation of electrostatic/ionic interactions, or other non-covalent interactions such as hydrogen bonds and Van Der Waals interactions.

For a photochemical bioconjugation method, a photosensitizer may be used to initiate the crosslinking reaction. In certain embodiments, the photosensitizer is selected from the group consisting of riboflavin, rose bengal, Eosin-Y, and a phenyl azide compound, which require light to initiate a photochemical crosslinking reaction. In certain embodiments, the photosensitizer further includes a crosslinking moiety that does not require light to initiate a crosslinking reaction. Exemplary crosslinking moieties that do not require light include N-hydroxysuccinimide, dimethyl suberimidate, formaldehyde, and carbodiimide. The photochemical bioconjugation method may use, for example, visible light or ultraviolet light. In another embodiment, the photochemical bioconjugation method uses blue visible light.

In another embodiment, riboflavin is used as the photo-sensitizer to crosslink thiolated hyaluronic acid and meth-acrylated hyaluronic to form the hydrogel.

In another embodiment, the method further comprises crosslinking a secreted factor from a stem cell with a photosensitizer via a non-light-activatable crosslinking moi-ety to produce a light-activatable bioconjugate of the secreted factor.

In other embodiments, a non-photochemical bioconjuga-tion method is used to form a hydrogel encapsulating secreted factors from a stem cell. In certain embodiments, the non-photochemical bioconjugation method uses strain-promoted azide-alkyne cycloaddition (SPAAC) click chem-istry or thiol-ene click chemistry to crosslink the hydrogel. Crosslinking by SPAAC may use, for example, an alkyne-NHS crosslinker, such as dibenzocyclooctyne-N-hydrox-ysuccinimide (DBCO-NHS), bicyclononyne-N-hydrox-ysuccinimide (BCN-NHS), and dibenzocyclooctyne-sulfo-N-hydroxysuccinimide (DBCO-sulfo-NHS), and/or an azide-NHS crosslinker, such as an azide-polyethylene glycol (PEG)-NHS crosslinker.

In another embodiment, the hydrogel is formed by cross-linking with SPAAC, the method comprising: a) reacting a first solution comprising a first hydrogel-forming molecule with an alkyne-NHS crosslinker to produce an alkyne-conjugated hydrogel-forming molecule; b) reacting a second solution comprising a second hydrogel-forming molecule with an azide-NHS crosslinker to produce an azide-conju-gated hydrogel-forming molecule; and c) crosslinking the azide-conjugated hydrogel-forming molecule with the alkyne-conjugated hydrogel-forming molecule to form the hydrogel. For example, alkyne-conjugated hyaluronic acid can be reacted with azide-conjugated hyaluronic acid to crosslink the hydrogel by SPAAC click chemistry.

In another embodiment, the method further comprises increasing crosslinking of the hydrogel using a multi-arm PEG linker comprising azide or alkyne groups. Exemplary multi-arm PEG linkers include 3-arm PEG, 4-arm PEG, 6-arm PEG, and 8-arm PEG.

In another embodiment, the biocompatible bioconjuga-tion method uses thiol-ene click chemistry. Crosslinking of the hydrogel with thiol-ene click chemistry can be per-formed by reacting a thiolated hydrogel-forming molecule with an acrylate- or methacrylate-functionalized hydrogel-forming molecule. For example, thiolated hyaluronic acid can be reacted with methacrylate-functionalized hyaluronic acid to form a hydrogel by thiol-ene click chemistry. Alter-natively, methacrylate-functionalized hyaluronic acid can be reacted with itself to form a crosslinked gel by polymeriza-tion of the methacrylate groups. In yet another embodiment, thiolated hyaluronic acid can be crosslinked by oxidation of thiol groups to form disulfide bonds to produce a gel that is at least partially mucoadhesive.

In another embodiment, the method further comprises injecting the one or more secreted factors from the stem cell, bioconjugation agents, and the at least one hydrogel-forming molecule into a tissue subsurface (e.g., subcutaneous tissue or subconjunctival space).

In another embodiment, the invention includes a method of treating damaged tissue in a subject, the method com-prising: a) collecting secretome from conditioned media of a culture of stem cells; b) mixing the secretome with hyaluronic acid and chondroitin sulfate to form a hydrogel comprising the secretome; and c) applying the hydrogel comprising the secretome to the damaged tissue. In certain embodiments, the stem cells are embryonic stem cells, adult stem cells, bone marrow stem cells, umbilical cord stem cells, or induced pluripotent stem cells. In one embodiment, the stem cells are human mesenchymal stem cells. In another embodiment, the method further comprises concentrating or lyophilizing the conditioned media.

In some embodiments, the secretome is at a concentration ranging from about 0.01 mg/mL to about 10 mg/ml in the hydrogel, including any concentration in this range such as about 0.01 mg/ml, 0.1 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9.0 mg/ml, 9.5 mg/ml, or 10 mg/ml. In another embodiment, the secretome is at a concentration of at least 1 mg/mL in the hydrogel.

The compositions described herein may be administered locally to a wound, within a wound or anatomical space or potential space (including a body cavity or fluid space, such as cerebrospinal fluid, joint, aqueous humor, vitreous humor, suprachoroidal space, subretinal space, or pleural cavity), or adjacent to a wound. In one embodiment, a wound dressing comprising one or more secreted factors and/or photosensi-tizers, and/or bioconjugation agents is applied to the dam-aged tissue. The wound dressing may comprise, for example, a gel, a viscoelastic solution, putty, a physical matrix or a membrane.

Compositions comprising secreted factors from stem cells and/or bioconjugation agents and/or hydrogel forming agents may take the form of a solution or gel. Moreover, the crosslinking reaction (whether covalent or non-covalent) may change the viscosity of a composition. Additionally, compositions may further comprise a pharmaceutically acceptable excipient.

In certain embodiments, the method further comprises preparing the damaged tissue prior to treating the subject by exfoliation or debridement of fibrotic or necrotic tissue.

In certain embodiments, multiple cycles of treatment are administered to the subject for a time period sufficient to effect at least a partial healing of the damaged tissue or more preferably, for a time period sufficient to effect a complete healing of the damaged tissue or wound closure.

In certain embodiments, treatment by a method described herein accelerates healing of the damaged tissue, increases thickness of an epithelial layer of the damaged tissue, increases the rate of epithelialization at the site of damaged tissue, prevents or reduces scar formation (or in the case of corneal tissue, preserves transparency), reduces inflamma-tion, shortens the time required for wound closure, or promotes nerve regeneration in the damaged tissue.

In another aspect, the invention includes a composition comprising a hydrogel encapsulating secretome from a stem cell.

In certain embodiments, the hydrogel comprises hyaluronic acid (HA) and chondroitin sulfate (CS). In one embodiment, the HA comprises methacrylated HA (MA-HA) and thiolated HA (SH-HA), for example, to allow crosslinking of the hydrogel by carrying out a thiol-ene reaction.

In certain embodiments, the composition further com-prises a photosensitizer (e.g., riboflavin).

In another embodiment, the hydrogel is crosslinked.

These and other embodiments of the subject invention will readily occur to those of skill in the art in view of the disclosure herein.

BRIEF DESCRIPTION OF THE FIGURES

FIG. 1A shows a schematic depicting the constituents of the proposed product, followed by the injection and in situ formation of the hyaluronic acid gel matrix that encapsulates and enables the sustained release of MSC secreted factors at the ocular wound surface. FIG. 1B shows an immunohistochemical cross-section of the photocrosslinkable HA membrane adhered to de-epithelialized corneal stroma. The HA membrane fluoresces in pink due to the chemical incorporation of an Alexa-Fluor 647. FIG. 1C shows a cytotoxicity assay of corneal stromal keratocytes showing nearly 100% viability of cells after direct exposure to the chemical reaction. FIG. 1D shows the bioactivity of epidermal growth factor upon exposure to pulsed blue light. The bioactivity of growth factors is minimally affected by blue light below 10 seconds of exposure. FIG. 1E shows rheology experiments showing the gelation effect of mixing the MSC secretome with the HA gel.

FIG. 4A. The epithelium layer from rat corneas was removed and the gel containing secretome was applied, 1 drop daily. After 24 hours, the group that received gel containing secretome had a smaller wound size compared to control group (FIG. 4B). FIG. 4C shows immunostaining of rat corneas 7 days after treating with HA/CS containing secretome. The epithelium layer was able to form Z0-1 and express CK3.

FIG. 8 shows light-induced thiol-ene reaction of methacrylated HA (MA-HA) and thiolated HA (SH-HA) with riboflavin phosphate (RFP).

DETAILED DESCRIPTION

Figure 1A:
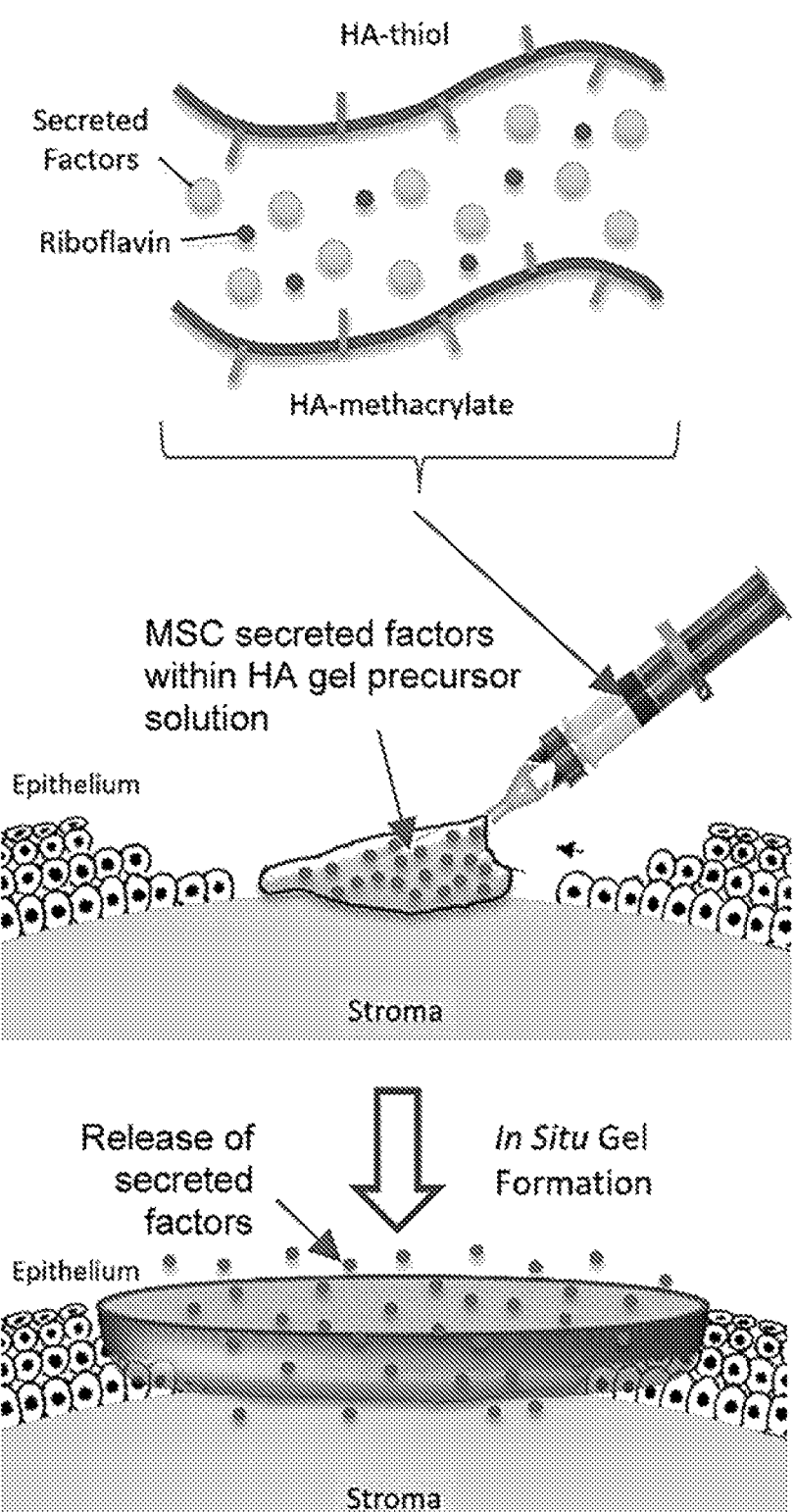
FIGS. 1A-1E show that a mixture of thiolated and methacrylated hyaluronic acid (HA) can be readily crosslinked by visible light in the presence of the FDA-approved photosensitizer riboflavin to create a biocompatible gel membrane that adheres to the ocular surface.
Figure 1B:
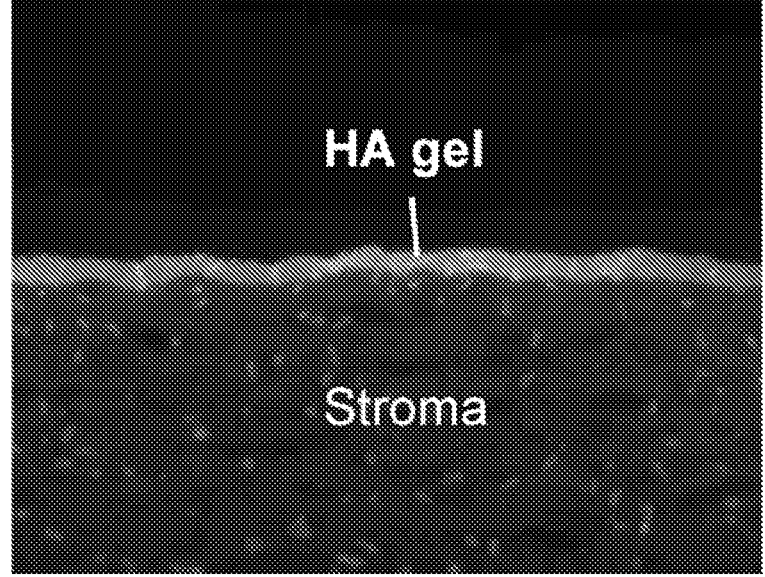
Figure 1C:
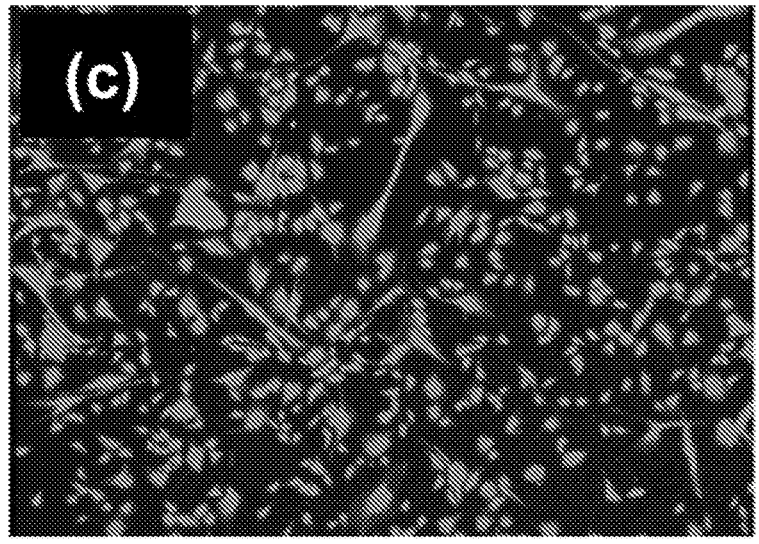
Figure 1D:
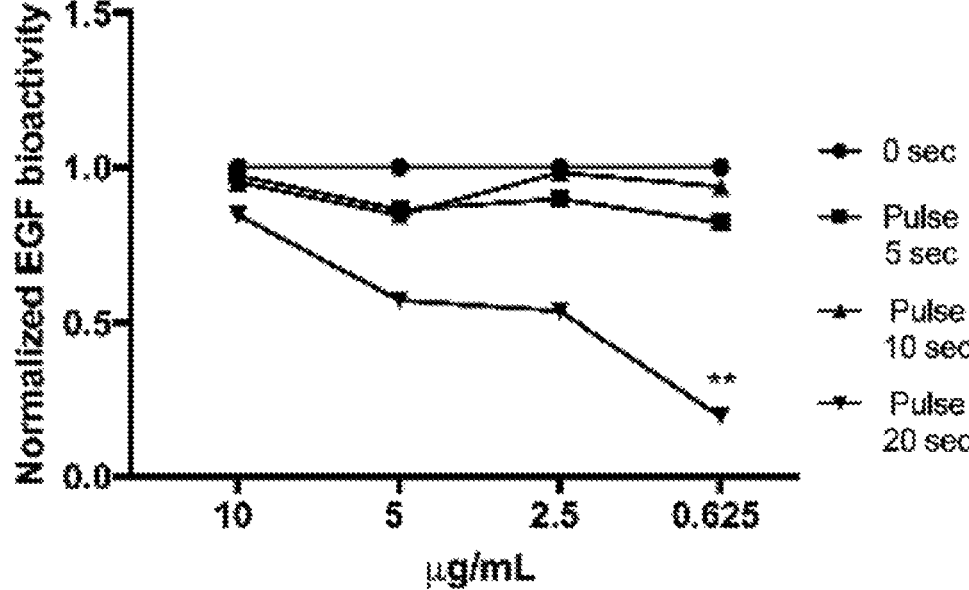
Figure 1E:
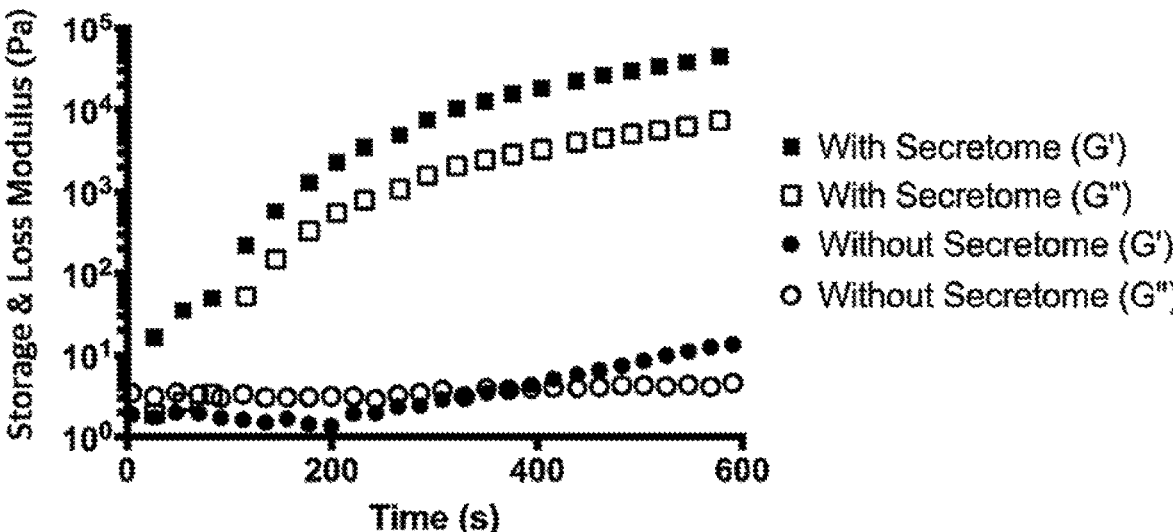

The practice of the present invention will employ, unless otherwise indicated, conventional methods of medicine, pharmacology, chemistry, biochemistry, molecular biology and recombinant DNA techniques, within the skill of the art. Such techniques are explained fully in the literature. See, e.g. S. S. Wong and D. M. Jameson *Chemistry of Protein and Nucleic Acid Cross-Linking and Conjugation* (CRC Press, 2$^{nd}$ edition, 2011); G. T. Hermanson *Bioconjugate Techniques* (Academic Press, 3$^{rd}$ edition, 2013); B. Bowling *Kanski's Clinical Ophthalmology: A Systematic Approach*, 8e (Saunders Ltd., 8$^{th}$ edition, 2015); A. L. Lehninger, *Biochemistry* (Worth Publishers, Inc., current addition); Sambrook et al., *Molecular Cloning: A Laboratory Manual* (3$^{rd}$ Edition, 2001); and *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the"

include plural referents unless the content clearly dictates otherwise. Thus, for example, reference to "a biomolecule" includes two or more biomolecules, and the like.

The term "about," particularly in reference to a given quantity, is meant to encompass deviations of plus or minus five percent.

The term "stem cell" refers to a cell that retains the ability to renew itself through mitotic cell division and that can differentiate into a diverse range of specialized cell types. Mammalian stem cells can be divided into three broad categories: embryonic stem cells, which are derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body by replenishing specialized cells. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal, which distinguishes them from non-stem cells. Induced pluripotent stem cells are a type of pluripotent stem cell derived from adult cells that have been reprogrammed into an embryonic-like pluripotent state. Induced pluripotent stem cells can be derived, for example, from adult somatic cells such as skin or blood cells.

As used herein, the term "cell viability" refers to a measure of the amount of cells that are living or dead, based on a total cell sample. High cell viability, as defined herein, refers to a cell population in which greater than 85% of all cells are viable, preferably greater than 90-95%, and more preferably a population characterized by high cell viability containing more than 99% viable cells.

As used herein, the term "secretome" refers to the factors secreted from stem cells, which may include extracellular vesicles containing secreted factors as cargo or vesicle-free secreted factors (e.g., solubilized secreted factors).

A "wound" is a break or discontinuity in the structure of an organ or tissue, including epithelium, connective tissue, and muscle tissue. Examples of wounds include, but are not limited to, skin wounds, burns, bruises, ulcers, bedsores, grazes, tears, cuts, punctures, perforations, corneal abrasions and disruptions, corneal damage caused by neurotrophic keratopathy and exposure keratopathy, and neurotrophic recurrent corneal erosions. A wound may include tissue damage produced by a surgical procedure, trauma, or disease.

"Topical" application refers to non-systemic local administration of an active ingredient (e.g., biomolecule or photosensitizer) to a surface or subsurface of damaged tissue or a wound.

The term "subject" includes both vertebrates and invertebrates, including, without limitation, mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese, and the like.

"Treatment" of a subject or "treating" a subject for a disease or condition herein means reducing or alleviating clinical symptoms of the disease or condition, including tissue damage or loss, nerve damage, or impaired or slow wound-healing.

By "therapeutically effective dose or amount" of a secreted factor from a stem cell is intended an amount that, when administered as described herein (e.g. alone or in combination with a bioconjugation agent and/or a hydrogel forming agent), brings about a positive therapeutic response in a subject having tissue damage or loss, such as an amount that improves wound healing or nerve regeneration. A therapeutically effective amount of a secreted factor from a stem cell may, for example, accelerate healing of damaged tissue, increase thickness of an epithelial layer of the damaged tissue, increase rate of epithelialization at the site of damaged tissue, shorten the time required for wound closure, or promote nerve regeneration in the damaged tissue. The exact amount required will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein.

The terms "peptide," "oligopeptide," and "polypeptide" refer to any compound comprising naturally occurring or synthetic amino acid polymers or amino acid-like molecules including but not limited to compounds comprising amino and/or imino molecules. No particular size is implied by use of the terms "peptide," "oligopeptide" or "polypeptide" and these terms are used interchangeably. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, linearly-linked peptides), cyclized, branched molecules and the like, are included within the definition. The terms also include molecules comprising one or more peptoids (e.g., N-substituted glycine residues) and other synthetic amino acids or peptides. (See, e.g., U.S. Pat. Nos. 5,831,005; 5,877,278; and 5,977,301; Nguyen et al. (2000) Chem Biol. 7(7):463-473; and Simon et al. (1992) Proc. Natl. Acad. Sci. USA 89(20):9367-9371 for descriptions of peptoids). Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, polypeptides useful in this invention can have a maximum length suitable for the intended application. Preferably, the polypeptide is between about 40 and 300 residues in length. Generally, one skilled in art can easily select the maximum length in view of the teachings herein. Further, peptides and polypeptides, as described herein, for example synthetic peptides, may include additional molecules such as labels or other chemical moieties. Such moieties may further enhance stimulation of epithelial cell proliferation and/or wound healing, and/or nerve regeneration, and/or biomolecule stability or delivery.

Thus, references to polypeptides or peptides also include derivatives of the amino acid sequences of the invention including one or more non-naturally occurring amino acids. A first polypeptide or peptide is "derived from" a second polypeptide or peptide if it is (i) encoded by a first polynucleotide derived from a second polynucleotide encoding the second polypeptide or peptide, or (ii) displays sequence identity to the second polypeptide or peptide as described herein. Sequence (or percent) identity can be determined as described below. Preferably, derivatives exhibit at least about 50% percent identity, more preferably at least about 80%, and even more preferably between about 85% and 99% (or any value therebetween) to the sequence from which they were derived. Such derivatives can include postexpression modifications of the polypeptide or peptide, for example, glycosylation, acetylation, phosphorylation, and the like.

Amino acid derivatives can also include modifications to the native sequence, such as deletions, additions and substitutions (generally conservative in nature), so long as the polypeptide or peptide maintains the desired activity (e.g., promote epithelial cell proliferation and wound healing). These modifications may be deliberate, as through site-directed mutagenesis, or may be accidental, such as through mutations of hosts that produce the proteins or errors due to PCR amplification. Furthermore, modifications may be made that have one or more of the following effects: increasing specificity or efficacy of biomolecule, enhancing epithelial cell proliferation, wound healing, and/or nerve regeneration, and facilitating cell processing.

"Substantially purified" generally refers to isolation of a substance (compound, polynucleotide, protein, polypeptide, peptide composition) such that the substance comprises the majority percent of the sample in which it resides. Typically, in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The invention is based on the discovery that biocompatible gel carriers can be used for delivery of secreted factors from stem cells to damaged tissue to enhance wound healing. In particular, the inventors have used an in situ forming, viscoelastic hyaluronic acid-based gel carrier for delivery of the secreted factors of bone-marrow derived human mesenchymal stem cells (hMSCs) to the eye. Other types of mesenchymal stem cells from other sources can also be used, as well as pluripotent stem cells. The secreted factors of cultured hMSCs can be collected and encapsulated within a hyaluronic acid-based gel on the corneal wound surface. This technology leverages the inherent biocompatibility and favorable biophysical properties of hyaluronic acid as well as the controllable production of secreted factors from cultured stem cells (see Examples).

In order to further an understanding of the invention, a more detailed discussion is provided below regarding methods of delivering therapeutic secreted factors from stem cells to damaged tissue to promote wound healing.

A. Targeted in Situ Therapeutic Delivery of Secreted Factors from Stem Cells

Secreted factors can be harvested from stem cell secretome, which may include extracellular vesicles containing secreted factors as cargo as well as vesicle-free secreted factors (e.g., solubilized secreted factors). The secreted factors from stem cells may include, but are not limited to, growth factors, cytokines, chemokines, anti-apoptotic factors, hormones, and extracellular matrix proteins. In certain embodiments, stem cell secretome is collected from conditioned media of cultured stem cells. The cultured stem cells may include stem cells from embryos, umbilical cord, or adult tissues, or induced pluripotent stem cells. Such stem cells may be totipotent, multipotent, or unipotent. In one embodiment, the stem cells are bone-marrow derived human mesenchymal stem cells (hMSCs). The entire stem cell secretome, a portion of the stem cell secretome (e.g., vesicle fraction or non-vesicle fraction), or one or more secreted factors may be used in the practice of the invention.

Bioconjugation can be used to encapsulate the secreted factors from stem cells in a hydrogel that covers damaged tissue where release of the secreted factors promotes healing. The hydrogel may be adherent or nonadherent to the tissue surface and encapsulate a single secreted factor, a subset of the secreted factors, or all the secreted factors collected from the cultured stem cells. Alternatively, bioconjugation can be used for direct covalent linkage of one or more of the secreted factors from stem cells to damaged tissue. In some embodiments, an uncrosslinked gel carrier is used for delivery of the secreted factors from stem cells. The secreted factors can be enclosed within extracellular vesicles, or solubilized without extracellular vesicles, or a combination thereof (some factors within vesicles, some not within vesicles).

The gel carrier may comprise, for example, glycoproteins, carbohydrates, and other macromolecules, including, but not limited to, various types of collagen, fibronectin, chitosan, laminin, hyaluronic acid, chondroitin sulfate, heparan sulfate, dermatan sulfate, chondroitin sulfate, methyl cellulose, hydroxy methyl cellulose, and synthetic macromolecules such as polyethylene glycol, polyvinyl pyrrolidone, or polyvinyl alcohol. In particular, hyaluronic acid and collagen I are useful for producing crosslinked or uncrosslinked hydrogels. A number of engineered elastin-like proteins have also been described for use in producing protein hydrogels (see, e.g., Straley et al. (2009) Soft Matter 5 (1):114-124, Madl et al. (2016) Adv. Funct. Mater. 26(21):3612-3620; herein incorporated by reference).

The secreted factors from the stem cells, biocompatible polymers or biopolymers (e.g., forming gel carrier), and in some cases, bioconjugation agents for crosslinking are applied to damaged tissue at a surface or a subsurface. For example, one or more secreted factors, biocompatible polymers or biopolymers, and/or bioconjugation agents may be applied at the surface of tissue (e.g., to promote wound closure) or beneath the surface (e.g. in stromal or subcutaneous tissue), or at the location of a damaged nerve (e.g., to promote nerve regeneration). In addition, damaged tissue may be prepared prior to treatment by exfoliation or debridement of fibrotic or necrotic areas.

In certain embodiments, a hydrogel encapsulating the secreted factors from stem cells is formed in situ on a wounded tissue surface through photochemical means. The secreted factors from stem cells together with a photosensitizer and hydrogel forming molecules (i.e., biocompatible polymers or biopolymers that form gel carrier) are applied to the tissue followed by exposure to non-visible or visible light (e.g., UV, white light, or blue visible light) at a suitable wavelength to initiate the crosslinking reaction between the hydrogel-forming molecules resulting in formation of the hydrogel on the tissue. Exemplary photosensitizers include riboflavin, rose bengal, eosin, and methylene blue, which upon exposure to light, produce reactive singlet oxygen and free radicals that generate covalent bonds between adjacent segments of macromolecules (e.g. hydrogel-forming molecules) that contain carbonyl functional groups. The appropriate wavelength for initiation of photochemical reactions depends on the photosensitizer that is used. For example, riboflavin absorbs UV light (360-370 nm) and blue visible light (about 458 nm), rose bengal and eosin both absorb green light (480-550 nm), and methylene blue absorbs visible light in the yellow to red range (550-700 nm). Additionally, molecules containing photo-activatable reactive chemical groups such as aryl azides and diazirines can be used as photosensitizers. For example, exposure of azidobenzamido groups to UV light (250-320 nm) generates aromatic nitrenes, which can insert into a variety of covalent bonds. Exposure of diazirines to UV light (330-370 nm) generates reactive carbene intermediates, which can form covalent bonds through addition reactions with amino acid side chains or the peptide backbone of proteins. For a description of photosensitizers and photocrosslinking techniques, see, e.g., DeRosa et al. (2002) Coordination Chemistry Reviews 233-234:351-371, Kamaev et al. (2012) Invest. Ophthalmol. Vis. Sci. 53(4):2360-2367, Mastropasqua et al. (2015) Eye Vis. 2:19, Lombardo et al. (2015) J Cataract Refract Surg. 41(2):446-459, Omobono et al. (2015) J Biomed Mater Res A. 103(4):1332-1338, Cherfan et al. (2013) Invest. Ophthalmol. Vis. Sci. 54(5):3426-3433, Liu et al. (1999) Methods Mol. Biol. 118:35-47, S. S. Wong and D. M. Jameson *Chemistry of Protein and Nucleic Acid Cross-Linking and Conjugation* (CRC Press, $2^{nd}$ edition, 2011), G. T. Hermanson *Bioconjugate Techniques* (Academic Press, $3^{rd}$ edition, 2013); herein incorporated by reference in their entireties). In one embodiment, riboflavin is used as the photosensitizer to crosslink thiolated hyaluronic acid and methacrylated hyaluronic to form a hydrogel encapsulating secreted stem cell factors.

In other embodiments, a non-photochemical bioconjugation method is used for forming a hydrogel encapsulating secreted factors from stem cells. For example, strain-promoted azide-alkyne cycloaddition (SPAAC), a Cu-free variation of click chemistry that is generally biocompatible with cells can be used for crosslinking hydrogel-forming molecules to generate a hydrogel. SPAAC utilizes a substituted cyclooctyne having an internal alkyne in a strained ring system. Ring strain together with electron-withdrawing substituents in the cyclooctyne promote a [3+2] dipolar cycloaddition with an azide functional group. SPAAC can be used for bioconjugation and crosslinking by attaching azide and cyclooctyne moieties to hydrogel-forming molecules. For a description of SPAAC, see, e.g., Baskin et al. (2007) Proc Natl Acad Sci USA 104(43):16793-16797, Agard et al. (2006) ACS Chem. Biol. 1: 644-648, Codelli et al. (2008) J. Am. Chem. Soc. 130:11486-11493, Gordon et al. (2012) J. Am. Chem. Soc. 134:9199-9208, Jiang et al. (2015) Soft Matter 11(30):6029-6036, Jang et al. (2012) Bioconjug. Chem. 23(11):2256-2261, Ornelas et al. (2010) J. Am. Chem. Soc. 132(11):3923-3931; herein incorporated by reference in their entireties.

Heterobifunctional crosslinking agents can be used to attach suitable azide and alkyne moieties to molecules for performing SPAAC. In particular, reactions with N-hydroxysuccinimide (NHS) can be used for bioconjugation of proteins such as collagen and elastin, which have multiple primary amines available as targets for coupling with NETS-activated reagents. Exemplary alkyne-NHS-crosslinker agents include dibenzocyclooctyne-N-hydroxysuccinimide (DBCO-NHS), bicyclononyne-N-hydroxysuccinimide (BCN-NHS), and dibenzocyclooctyne-sulfo-N-hydroxysuccinimide (DBCO-sulfo-NHS). Exemplary azide-NHS crosslinker agents include azide-polyethylene glycol (PEG)-NHS crosslinkers with PEG polymers of various lengths (azide-$PEG_n$-NHS). The length of the PEG polymer can be used to control the spacing between the NETS and azide moieties. The PEG spacer arms may range from one PEG unit to many PEG units in length up to an average molecular weight of about 14,000 Da. The spacer arm may also comprise other types of chemical backbones, such as an aliphatic backbone. Heterobifunctional crosslinking agents suitable for performing SPAAC are commercially available from a number of companies, including JenKem Technology USA (Plano, TX), Sigma-Aldrich, Inc. (St. Louis, MO), BroadPharm (San Diego, CA), Quanta BioDesign (Plain City, OH), Thermo Fisher Scientific Inc. (Waltham, MA), and Nanocs Inc. (New York, NY); herein incorporated by reference.

For example, an alkyne-conjugated hydrogel-forming molecule can be produced by reacting the hydrogel-forming molecule (e.g., in a first solution) with an alkyne-NHS crosslinker. An azide-conjugated hydrogel-forming molecule can be produced by reacting the hydrogel-forming molecule (e.g., in a second solution) with an azide-NHS crosslinker. SPAAC is then performed to crosslink the azide-conjugated hydrogel-forming molecule with the alkyne-conjugated hydrogel-forming molecule (e.g., by mixing the first and second solutions) to form the hydrogel. A multi-arm PEG linker comprising an azide or alkyne group may be used to further increase crosslinking of the hydrogel. Exemplary multi-arm PEG linkers include 3-arm PEG, 4-arm PEG, 6-arm PEG, and 8-arm PEG. Such crosslinkers are commercially available from JenKem Technology USA (Plano, TX).

In addition, the secreted factors from stem cells can be crosslinked to the hydrogel-forming molecule within the hydrogel using SPAAC. For example, secreted factors can be conjugated for SPAAC with an azide-N-hydroxysuccinimide (NHS) crosslinker to produce an azide-conjugated secreted factor. The hydrogel-forming molecule can be conjugated with an alkyne-NHS crosslinker to produce an alkyne-conjugated hydrogel-forming protein, which is subsequently reacted with the azide-conjugated secreted factor, thereby crosslinking the hydrogel-forming molecule and the secreted factor within the hydrogel. Alternatively, a secreted factor can be reacted with an alkyne-NHS crosslinker to produce an alkyne-conjugated secreted factor. A hydrogel-forming molecule can be reacted with an azide-NHS crosslinker to produce an azide-conjugated hydrogel-forming molecule, which is subsequently reacted with the alkyne-conjugated secreted factor thereby crosslinking the hydrogel-forming molecule and the secreted factor within the hydrogel.

Alternatively, thiol-ene click chemistry can be used to form a hydrogel. Bioconjugation using thiol-ene click chemistry involves reacting a thiol group with an alkene group via Michael addition. The thiol-ene click reaction can be optionally augmented by light (i.e., photo-click reaction). In one embodiment, thiol-ene click chemistry is used to produce a hydrogel by crosslinking a thiolated macromolecule with an acrylate-functionalized macromolecule. Hydrogels can be produced in this manner using suitable hydrogel-forming proteins, polymers or macromolecules, such as described above. For example, thiolated hyaluronic acid can be crosslinked with acrylate-functionalized hyaluronic acid to produce a hydrogel encapsulating secreted factors from stem cells. For a description of the use of thiol-ene click chemistry for crosslinking and forming hydrogels, see, e.g., Grim et al. (2015) J. Control Release 219:95-106; Scanlan et al. (2014) Molecules 19(11):19137-151; Hoyle et al. (2010) Angew Chem. Int. Ed. Engl. 49(9):1540-1573; van Dijk et al. (2009) Bioconjug. Chem. 20(11):2001-2016; herein incorporated by reference in their entireties.

In another embodiment, in situ gel formation is accomplished using multi-functional succinimidyl esters of polyethylene glycol (PEG). Hydroxysuccinimide (NHS) ester-activated PEG crosslinkers react efficiently with primary amino groups (—NH$_2$) at a pH ranging from about 7 to about 9 to form stable amide bonds. In particular, proteins such as collagen and growth factors have multiple primary amine groups available for coupling with NETS-activated reagents. Sulfonated crosslinkers have the advantage that they tend to be water soluble and can be applied to tissue in situ safely without an organic solvent. Amine-reactive NHS moieties on multi-arm PEG crosslinkers have the added advantage of enabling adhesion to stromal tissue. Multifunctional PEG-NETS esters also provide a systematic way to tune the mechanical and adhesive properties of a hydrogel to optimize its effects on wound healing. In one embodiment, a multi-functional PEG-NETS is mixed with a hydrogel-forming protein (e.g., collagen) and at least one secreted factor from a stem cells to form a stem cell secreted factor conjugated hydrogel on the surface of a tissue. Exemplary multi-arm PEG-NETS linkers that can be used in the practice of the invention include 3-arm PEG, 4-arm PEG, 6-arm PEG, and 8-arm PEG.

Photochemical or non-photochemical bioconjugation methods can also be used for direct covalent linkage of secreted factors from stem cells to damaged tissue as well as crosslinking the secreted factors with one another. Secreted factors from stem cells may include more than one functional group that can be crosslinked to allow formation of bonds among multiple secreted factors and a tissue surface or subsurface. For example, secreted factors from stem cells can be covalently attached to tissue using SPAAC by reacting the damaged tissue with an azide-N-hydroxysuccinimide (NETS) crosslinker to produce azide-derivatized tissue, wherein proteins such as collagen in the damaged tissue are covalently coupled to azide functional groups. One or more secreted factors can be reacted with an alkyne-NHS crosslinker to produce alkyne-conjugated secreted factors, which can be subsequently reacted with the azide-derivatized tissue using SPAAC to covalently link the secreted factors to the damaged tissue.

Alternatively, the damaged tissue can be reacted with an alkyne-NHS crosslinker to produce alkyne-derivatized tissue, wherein proteins such as collagen are covalently coupled to alkyne functional groups. One or more secreted factors can be reacted with an azide-PEG-NHS crosslinker to produce azide-conjugated secreted factors, which can be subsequently reacted with the alkyne-derivatized tissue using SPAAC to covalently link the secreted factors to the damaged tissue.

In certain embodiments, more than one bioconjugation step is performed. For example, at least one bioconjugation step may be performed in vitro, and at least one bioconjugation step may be performed directly on the damaged tissue. Alternatively or additionally, more than one bioconjugation technique may be used for crosslinking. For example, SPAAC click chemistry can be combined with thiol-ene click chemistry to crosslink different molecules. As will be clear to one of skill in the art, some bioconjugation chemistries are more advantageous depending on the conditions, tissue being treated, and the particular secreted factors, polymers, or other factors being crosslinked.

B. Applications

The methods of the invention can be applied to any number of medical applications where tissue regeneration or improved wound healing is needed. Any condition where healing is impaired may especially benefit from such treatment. For example, tissue damage caused by physical trauma, burns, chemical exposure, disease, or surgery, including, but not limited to, chemical injuries, skin injuries, nerve injuries, or eye injuries may benefit from treatment as described herein.

For example, damage to corneal tissue, such as caused by a chemical burn, severe dry eye, keratoconjunctivitis sicca, Sjogren's syndrome, ocular graft-versus-host disease, ocular cicatricial pemphigoid (OCP), Stevens-Johnson syndrome (SJS), physical trauma, neurotrophic keratopathy, a recurrent corneal erosion, a corneal ulcer, exposure keratopathy, retinal disease or degeneration, or optic nerve damage or degeneration may be treated by the methods described herein. The corneal surface can be prepared by optionally debriding the edges of an epithelial defect and its base, followed by application of one or more secreted factors from stem cells alone or in combination with bioconjugation agents (e.g., photochemical bioconjugation agents and photosensitizers, or nonphotochemical bioconjugation agents) and/or hydrogel-forming agents to the surface using sterile week-cells. For photochemical bioconjugation, the tissue surface is exposed to UV or visible light, depending on the selected photosensitizer, to initiate photocrosslinking. For UV crosslinking, an optional contact lens (non-UV absorbing) can be placed at the time of a UV exposure to limit the crosslinking reaction to the corneal surface. In one embodiment, secreted factors from stem cells are encapsulated in a matrix using thiolated and methacrylated hyaluronic acid in the presence of riboflavin and blue light to create a gel generated by "photo-click" thiol-ene chemistry. An optional bandage contact lens may be placed on the eye after the reaction.

In other embodiments, non-covalent crosslinking methods are used such as ionic or electrostatic crosslinking, or through the use of hydrogen bonds or Van Der Waals interactions. In still other embodiments, no chemical crosslinking is used at all, and instead linear biomolecules or polymers are used as a carrier for the stem cell secreted factors such as a glycoprotein, a glycosaminoglycan, a carbohydrate, collagen, fibronectin, chitosan, laminin, hyaluronic acid, chondroitin sulfate, heparan sulfate, dermatan sulfate, chondroitin sulfate, methyl cellulose, hydroxy methyl cellulose, polyethylene glycol, polyvinyl pyrrolidone, and polyvinyl alcohol. Combinations of these molecules can also be used as a carrier for the stem cell secreted factors.

C. Pharmaceutical Compositions

Secreted factors from stem cells, biocompatible polymers or biopolymers (e.g., forming gel carrier), and bioconjugation agents (e.g., photochemical bioconjugation agents and photosensitizers, or nonphotochemical bioconjugation agents) can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amounts of secreted factors from stem cells, biocompatible polymers or biopolymers (e.g., forming gel carrier), and bioconjugation agents (e.g., when contained in a drug delivery system) in a composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, NJ (1998), and Kibbe, A. H., Handbook of Pharmaceutical Excipients, 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for topical, subcutaneous, or localized delivery.

The pharmaceutical preparations herein can also be housed in a syringe, an implantation device, a microneedle injection system, or the like, depending upon the intended mode of delivery and use. Preferably, the compositions comprising therapeutic factors and/or photosensitizers, prepared as described herein, are in unit dosage form, meaning an amount of a conjugate or composition of the invention appropriate for a single dose, in a premeasured or prepackaged form.

The compositions herein may optionally include one or more additional agents, such as other drugs for treating a wound or tissue damage, or other medications used to treat a subject for a condition or disease. Compounded preparations may be used including therapeutic factors and/or photosensitizers and one or more other drugs for treating a wound or tissue damage, such as, but not limited to, analgesic agents, anesthetic agents, antibiotics, anti-inflammatory agents, or other agents that promote wound healing. Alternatively, such agents can be contained in a separate composition from the composition comprising biomolecules and co-administered concurrently, before, or after the composition comprising biomolecules.

D. Administration

At least one therapeutically effective cycle of treatment with at least one secreted factor from a stem cell will be administered to a subject in need of tissue regeneration or repair. By "therapeutically effective dose or amount" of a secreted factor from a stem cell is intended an amount that, when administered as described herein (e.g., alone or in combination with bioconjugation agents (e.g., photochemical bioconjugation agents and photosensitizers, or nonphotochemical bioconjugation agents) and/or biocompatible polymers or biopolymers (forming gel carrier), brings about a positive therapeutic response in a subject having tissue damage or loss, such as an amount that improves wound healing or nerve regeneration. A therapeutically effective amount of a therapeutic factors may, for example, accelerate healing of damaged tissue, increase thickness of an epithelial layer of the damaged tissue, increase rate of epithelialization at the site of damaged tissue, promote regeneration of tissues or organs, shorten the time required for wound closure, or promote nerve regeneration. Additionally, an "effective amount" of a bioconjugation agent is an amount sufficient for crosslinking secreted factors from stem cells directly onto tissue or crosslinking hydrogel-forming agents to generate a hydrogel in situ encapsulating secreted factors from stem cells on tissue.

In certain embodiments, multiple therapeutically effective doses of compositions comprising one or more secreted factors from stem cells, and/or bioconjugation agents, and/or biocompatible polymers or biopolymers (e.g., forming gel carrier), and/or photosensitizers and/or one or more other therapeutic agents, such as other drugs or agents for treating a wound or damaged tissue, or other medications will be administered. The compositions of the present invention are typically, although not necessarily, administered topically, via injection (subcutaneously or intramuscularly), by infusion, or locally. Additional modes of administration are also contemplated, such as transdermal, intradermal, and so forth.

The preparations according to the invention are also suitable for local treatment. Compositions comprising one or more secreted factors from stem cells, and/or bioconjugation agents, and/or biocompatible polymers or biopolymers (e.g., forming gel carrier), and/or photosensitizers may be administered directly on the surface of a wound, adjacent to a wound, or beneath the surface of a wound (e.g. in stromal or subcutaneous tissue). Additionally, compositions may be applied at the location of a damaged nerve (e.g., to promote nerve regeneration). For example, a composition may be administered by spraying the composition on a wound, or as drops or a topical paste. One or more secreted factors from stem cells, and/or bioconjugation agents, and/or biocompatible polymers or biopolymers (e.g., forming gel carrier), and/or photosensitizers may also be added to wound dressings. A wound dressing may comprise, for example, a gel, a viscoelastic solution, putty, a physical matrix or a membrane. The particular preparation and appropriate method of administration are chosen to target secreted factors from stem cells to the site in need of tissue regeneration or repair.

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising therapeutic factors, photosensitizers, and other agents may be administered using the same or different modes of administration in accordance with any medically acceptable method known in the art.

In another embodiment, the pharmaceutical compositions comprising one or more secreted factors from stem cells, and/or bioconjugation agents, and/or hydrogel-forming molecules, and/or photosensitizers, and/or other agents are administered prophylactically. Such prophylactic uses will be of particular value for subjects who suffer from a condition which impairs or slows down the healing of a wound or causes tissue damage or prior to a procedure that will cause tissue damage.

In another embodiment of the invention, the pharmaceutical compositions comprising biomolecules and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising secreted factors from stem cells (e.g. secreted factor-photosensitizer conjugate) as provided herein to a patient suffering from a condition that is responsive to treatment with the secreted factors from stem cells contained in the conjugate or composition. The method comprises administering, via any of the herein described modes, a therapeutically effective amount of the conjugate or drug delivery system, preferably provided as part of a pharmaceutical composition. In one embodiment, hyaluronic acid is conjugated in one batch with thiols groups and conjugated in a second batch with acrylate or methacrylate groups. When mixed together and exposed to UV or blue light in the presence of riboflavin, a so-called photoinitiated "thiol-ene" or "photo-click" reaction takes place that rapidly forms a hyaluronic acid gel. This gel can be used alone or to encapsulate other secreted factors from stem cells (with or without a thiol or acrylate/methacrylate functionality) on wounds to promote healing as described herein. In other embodiments, methacrylated hyaluronic acid alone can be crosslinked or thiolated hyaluronic acid alone can be crosslinked, the latter forming a tissue-adherent gel.

The actual dose of secreted factors from stem cells (e.g., alone or in combination with bioconjugation agents (e.g., photochemical bioconjugation agents and photosensitizers, or nonphotochemical bioconjugation agents) and/or biocompatible polymers or biopolymers (e.g., forming gel carrier) to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. The amount of secreted factors from stem cells administered will depend on the potency of particular secreted factors and the magnitude of their effect on tissue regeneration and repair (e.g., wound epithelialization and healing, nerve regeneration) and the route of administration.

Secreted factors from stem cells, prepared as described herein (again, preferably provided as part of a pharmaceutical preparation), can be administered alone or in combination with one or more other therapeutic agents for treating a wound or tissue damage, such as, but not limited to, analgesic agents, anesthetic agents, antibiotics, anti-inflammatory agents, or other agents that promote wound healing, or other medications used to treat a particular condition or disease according to a variety of dosing schedules depending on the judgment of the clinician, needs of the patient, and so forth. Secreted factors from stem cells, drugs, or other agents can be trapped within a gel either through physical entanglements or via covalent bonds that are either non-specific or specific. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day. In some cases, only a single administration will be needed.

Secreted factors from stem cells (e.g., alone or in combination with bioconjugation agents (e.g., photochemical bioconjugation agents and photosensitizers, or nonphotochemical bioconjugation agents) and/or biocompatible polymers or biopolymers (e.g., forming gel carrier) can be administered prior to, concurrent with, or subsequent to other agents. If provided at the same time as other agents, secreted factors from stem cells can be provided in the same or in a different composition. Thus, secreted factors from stem cells and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising secreted factors form stem cells and a dose of a pharmaceutical composition comprising at least one other agent, such as another drug for treating a wound or damaged tissue, which in combination comprise a therapeutically effective dose, according to a particular dosing regimen. Similarly, secreted factors from stem cells and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Figure 2:
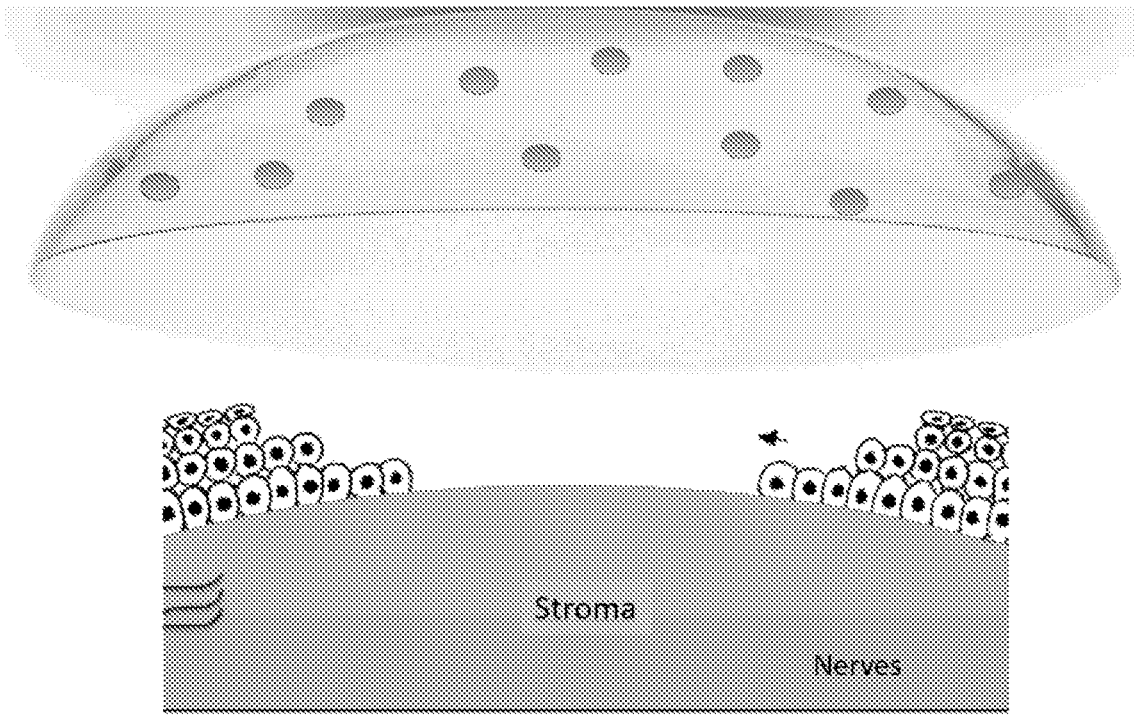
FIG. 2 shows a schematic depicting an in situ forming "contact lens" with encapsulated growth factors or stem cell secreted factors. This contact lens may or may not be adherent to the tissue surface.

In some embodiments, the secreted factors of stem cells are encapsulated in a biomaterial, such as hyaluronic acid formed by a photo-click reaction (thiolated hyaluronic acid reacted with methacrylated hyaluronic acid, activated by a photosensitizer such as riboflavin and exposure to blue light). In one embodiment, the stem cell secretome is encapsulated within a mucoadherent gel that adheres to living tissue, to form a wound dressing. In another embodiment, the secretome is encapsulated within a non-adherent gel membrane, such as one formed by SPAAC click chemistry (reaction of azide and alkyne groups) to crosslink exogenous matrix proteins such as conjugated collagen or conjugated hyaluronic acid, which are not crosslinked to the wound. In that case, the encapsulated matrix would gelate to form (in situ), a "contact lens" that conforms to the contour of the ocular surface. If applied followed by eyelid closure, the collagen (or other type of gel, such as a hyaluronic acid) gel is "molded" to the surrounding ocular structures and acts as a contact lens that protects the eye while serving as a depot for therapeutic factors such as the stem cell secretome. FIG. 2 shows an example of such a contact lens—this lens could be formed ex vivo (outside the eye or body) or formed in situ, i.e. directly on the eye surface (or other wound site). The lens can then be removed, or allowed to break apart or resorb/extrude on its own once it has served its purpose.

E. Kits

The invention also provides kits comprising one or more containers holding compositions comprising secreted factors from stem cells, bioconjugation agents (e.g., photochemical bioconjugation agents and photosensitizers, or nonphotochemical bioconjugation agents) and/or biocompatible polymers or biopolymers (e.g., forming gel carrier), and optionally one or more other drugs for treating a wound or tissue damage, such as, but not limited to, analgesic agents, anesthetic agents, antibiotics, anti-inflammatory agents, or other agents that promote wound healing or tissue regeneration. Compositions can be in liquid form or can be lyophilized. Suitable containers for the compositions include, for example, bottles, vials, syringes, and tubes. Containers can be formed from a variety of materials, including glass or plastic. A container may have a sterile access port (for example, the container may be a vial having a stopper pierceable by a hypodermic injection needle). Additionally, the kit may contain a light source that produces light (e.g., UV or visible) at a wavelength capable of activating a photosensitizer included in the kit, a UV filter, a non-UV absorbing contact lens, or a topical applicator or dispenser.

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions describing methods for treating damaged tissue with secreted factors from stem cells as described herein. The package insert can be an unapproved draft package insert or can be a package insert approved by the Food and Drug Administration (FDA) or other regulatory body.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

General Overview: Harnessing the Therapeutic Potential of the Stem Cell Secretome Through Biomolecular Engineering The management of corneal and ocular surface wounds has not changed significantly in the last few decades and consists mainly of measures such as lubrication, patching, and antibiotics that support but do not promote wound healing. In severe injuries and disease such as chemical burns and Stevens-Johnson Syndrome, irreversible visual loss often occurs in spite of such measures. Thus, there remains a major clinical need for technologies that specifically promote regeneration of the cornea and ocular surface.

Mesenchymal stem cells (MSCs) play an important role in tissue repair and maintenance and have been extensively studied for regenerative therapies. Animal studies have shown that MSCs can prevent scarring, block neovascularization, inhibit inflammation, and promote epithelial healing in the cornea after injuries. The primary mechanism of action for most of the observed therapeutic effects of MSCs appears to be the production of immunomodulatory and trophic cytokines. In spite of their demonstrated benefit in animal models, clinical studies of MSCs in eye diseases are very limited.

The administration of the therapeutic factors secreted by harvested stem cells is an attractive and viable option for treating wounded or diseased tissue that avoids the uncertainties and challenges of delivering actual stem cells into patients. Yet, simple topical delivery of soluble therapeutic factors to the eye is limited and cost-inefficient due to fluid turnover from tearing and drainage through the lacrimal pathway. Of particular benefit would be a vehicle that could deliver these therapeutic factors in a sustained fashion while maintaining their bioactivity and also serving as a protective membrane to the wound itself. Here we describe an in situ forming, viscoelastic gel carrier that can facilitate the optimum delivery of the secreted factors of bone-marrow derived human mesenchymal stem cells (hMSCs) to the eye.

In one part of this work, the secreted factors of hMSCs are produced, collected, and packaged in lyophilized form ex vivo, and then encapsulated within a protective, tissue-adherent hyaluronic acid-based gel on the corneal wound surface. This technology leverages the inherent biocompatibility and favorable biophysical properties of hyaluronic acid as well as the controllable production of secreted factors from cultured stem cells.

Example 2

Experimental Design

Here we describe an exemplary delivery system for MSC-based therapeutics, which utilizes a biocompatible in situ forming HA-conjugate that forms an adherent membrane on a wound in situ. A ubiquitous proteoglycan found in connective tissues throughout the body, HA is already FDA-approved as a biomaterial for ophthalmic viscosurgical devices (OVD) for cataract surgery to create and maintain space in the anterior chamber of the eye as well as to protect delicate intraocular structures. Readily manufactured, packaged, sterilized, and highly biocompatible, HA itself also has known effects on wound healing, and is available in various derivative forms that confer the capacity to form a crosslinked gel in situ. The membrane forms within minutes upon exposure to body temperature.

We have developed a novel wound healing modality combining (1) MSC secreted factors produced, harvested, and packaged in lyophilized form ex vivo, and (2) a light-cured, hyaluronic acid-based gel to encapsulate and secure the secreted factors within a protective membrane on a wound surface. The lyophilized secreted factors are re-constituted, mixed into the OVD, and applied to the ocular surface at the point-of-care to form a depot of hMSC secreted factors within a gel matrix. The idea leverages the inherent biocompatibility and favorable biophysical properties of hyaluronic acid (HA), the safety profile of riboflavin-based crosslinking via visible light, and the highly controllable production of secreted factors from cultured, bone-marrow derived hMSCs that promote wound healing.

We have developed a mucoadherent, in situ forming hyaluronic acid gel that forms upon mixing and exposure to blue light in the presence of riboflavin. We use gel cross-linking techniques to create low and high crosslinking density microenvironments for cells in both 2D and 3D cultures that modulate the expression profile of the MSC secretome.

Another embodiment provides a non-adherent, in situ forming gel (e.g. hyaluronic acid or collagen-based, at least in part) that encapsulates the secretome with or without the help of photosensitizers like riboflavin and light such as blue light (e.g. by SPAAC click chemistry or succinimidyl chemistry that does not require a catalyst).

We have developed a product that combines (1) MSC secreted factors produced, harvested, and packaged in lyophilized form ex vivo and (2) an HA-based gel to encapsulate and secure these secreted factors within a protective membrane on a wound surface. As discussed above, other carrier matrices can be used including but not limited collagen (or combinations of biomolecules such as collagen and hyaluronic together, or other combinations). The lyophilized secreted factors are re-constituted, mixed into the gel, and applied to the ocular surface at the point-of-care to form a depot of hMSC secreted factors within a mucoadherent, gel matrix. The idea leverages the inherent biocompatibility and favorable biophysical properties of HA and the highly controllable production of secreted factors from cultured, bone-marrow derived hMSCs that promote wound healing. This technology may be useful in treatment of severe ocular surface injuries such as chemical burns and Stevens-Johnson Syndrome and also have broad applicability to the treatment of chemical burns and poorly healing wounds of the skin and other tissues as well as in the regeneration of a wide variety of tissues including but not limited to mucosal, nerve, and musculoskeletal tissue.

Example 3

Producing a Biocompatible Gel Membrane that Adheres to the Ocular Surface

We have shown that (1) a mixture of thiolated and methacrylated hyaluronic acid can be readily crosslinked by visible light in the presence of the FDA-approved photosensitizer riboflavin phosphate to create a biocompatible gel membrane that adheres to the ocular surface (FIG. 1), and (2) the secretome of human bone marrow-derived MSCs can accelerate wound healing in total epithelial injuries of the cornea in a murine model. We are using this light-curable hyaluronic acid to encapsulate MSC secreted factors within a thin membrane that covers and stabilizes wounds on the ocular surface.

Other gels such as collagen gels formed by copper free click chemistry (via azide and/or alkyne functionalization of hyaluronic acid and crosslinkers with corresponding alkyne or azide groups), succinimidyl chemistry (using multi-functional crosslinkers such as 4-arm or 8-arm PEG crosslinking), thiol-ene chemistry, and blue light photochemistry (e.g. using riboflavin phosphate as photosensitizer) to directly crosslink collagen or other proteins can also be used. In addition, other types of hyaluronic acid gels can be used, such as amine-functionalized hyaluronic acid crosslinked via multi-functional succinimidyl crosslinkers (e.g. PEG crosslinkers) and copper free click chemistry (via azide and/or alkyne functionalization of hyaluronic acid and crosslinkers with corresponding alkyne or azide groups). The common thread is the use of the secreted factors of stem cells such as (but not limited to) mesenchymal stem cells derived from human bone marrow, for instance (but also from other sources). Pluripotent stem cells may also be used to generate the secreted factors. Stem cells can be stimulated using various methods such as varying stiffness of the surface on which (or matrix within) they are grown, and various growth factor(s) can be used in either 2D or 3D culture to stimulate growth and differentiation (or differential production by) the stem cells.

Example 4

HA Gel Synthesis and Characterization

HA gels are prepared as follows. Thiolated and methacrylated HA (Vornia Biomaterials) and riboflavin phosphate are mixed with 40 mg/mL lyophilized MSC secretome and exposed to pulsed blue light (~458 nm). The concentrations of conjugated HA, riboflavin phosphate, as well as blue light intensity and exposure time are systematically varied to optimize for secretome bioactivity. The rheological and protein release properties of these gels are characterized at the Stanford Soft Materials Facility while the biological response to the gels tested through in vitro primary corneal epithelial wound healing assays for cell viability, proliferation, migration, and phenotype.

Example 5

Photo-Click Hyaluronic Acid Gel Formation and Rheology Measurements

Thiolated hyaluronic acid (SH-HA) and methacrylated hyaluronic acid (MA-HA) (Vornia Biomaterials) were dis-solved in pH 7.4 phosphate buffered saline (PBS) as 10 mg/mL, respectively. Riboflavin phosphate (Sigma-Aldrich) was dissolved in PBS as 1 mg/mL. SH-HA, MA-HA, and riboflavin phosphate solutions were mixed as 50:50:1 volume ratio, and then the mixed solution was incubated at 4° C. To fabricate the photo-click HA gel, 100 mW/cm$^2$ of blue light was exposed to the solution. ARES-G2 (TA instruments) rheometer was used for measuring rheology. Time sweeps were performed at 1% strain and 1 Hz oscillatory frequency, and frequency sweeps from 0.1-10 Hz with a fixed 1% strain were performed.

The reaction of thiols with alkenes is regarded click reaction by some characteristics such as high yields, regio-specificity/sterospecificity, insensitivity to oxygen or water, solventless or aqueous mild reaction condition, and orthogonality. The thiol-ene click reaction can be divided into two specific reactions. One is thiol Michael addition proceeded by anionic chain of catalyst, and the thiol reacts with electron-deficient carbon-carbon double bonds. Another is thiol-ene radical addition proceeded by a radical initiated by light, heat, or radical initiators. Commonly, the thiol-ene radical reaction generated by photo-initiator with light have been called photo-click chemistry.

The photo-click reaction has been achieved using UV light. However, UV light can lead harmful effects on the eye. Here, visible (blue) light was applied with riboflavin phosphate to avoid side effects of UV light. Other forms of catalysts/initiators can be used in combination with this.

The stem cell secretome can also be encapsulated within other types of gels (e.g. collagen) and other chemistries such as SPAAC copper-free click chemistry, to form a "contact lens" or injected into the subconjunctival space or other spaces in the eye (e.g. the vitreous, etc. . . . ) or other areas of the body to deliver the secretome in a site-specific, controlled release fashion.

The fabricated HA gel is biocompatible and provides not only a matrix drug reservoir, but also, therapeutic factors itself by degradation.

Rheology

1. Blue Light Exposure Time Effect

The HA gels formed by photo-click chemistry were dependent on the blue light exposure time. The mixture solution without blue light exposure (HA 0 s) showed no transition during 600 seconds, which indicates that the reaction between SH-HA and MA-HA did not occur near body temperature without radical initiation.

The initial modulus of photo-click HA gel increased with blue light exposure time, and the critical exposure time was pulsed for 10 seconds (p 10 s). The storage modulus of HA p 10 s showed a significant difference to the 0 and pulse 5 seconds, and it also slightly increased for 600 seconds.

In comparison, with pulses of 15 and 20 seconds (p15 s and p20 s, respectively), there was difference in the initial storage modulus, but the increasing rate of p15 s was higher than p20 s, and the storage modulus became similar after 600 seconds. The loss modulus of p15 s was gradually increased for 600 seconds, while p20 s maintained high loss modulus for all time. Both p15 s and p20 s had gel points near 300 seconds.

2. Temperature Effect

When two different temperatures were used for gelation, there was no significant effect of temperature on gel formation. The blue light-exposed HA mixture solution did not form gels immediately, though samples exposed to blue light for longer times showed a slightly increased and stable modulus. To fabricate a photo-click HA gel, the dissolution of riboflavin phosphate is an important factor. Riboflavin phosphate, which has good solubility in water, is a preferable form of riboflavin for the purposes of this invention.

3. Addition of Secretome

To evaluate the change in physical properties resulting from addition of secretome, rheology of the secretome added HA photo-click gel was also measured. Interestingly, the modulus was greatly increased with addition of secretome.

Example 6

Additive Corneal Wound Healing Effects of Human Mesenchymal Stem Cell Secreted Factors and Hyaluronic Acid-Based Viscoelastic Gel Human mesenchymal stem cells (hMSC) applied to the wounded eye have been shown to improve the rate of wound healing possibly due to the paracrine factors produce by these cells (the secretome). We hypothesized that combining secretome and a gel carrier would provide an additive effect on corneal wound healing over topical delivery of the secretome alone. Here, we aimed to deliver the hMSC secretome to the corneal surface using a viscous gel formulation of hyaluronic acid (HA) and chondroitin sulfate (CS) as a vehicle.

Conditioned media was produced, collected and lyophilized from bone marrow-derived hMSCs. Primary rabbit corneal epithelial cells (CECs) at passage two were starved in serum-free medium for 12 hours, and then the various treatments were added. Lyophilized secretome and HA/CS were serially diluted in phosphate buffered saline down to 0.01 mg/mL. Various concentrations of each were applied to starved CECs cells. At 24, 48 and 72 hours, cell proliferation was measured using a cell counting kit. The same assay was repeated for a mixture of secretome and HA/CS with the optimal concentrations that had been determined for each component individually. For in vivo assays in mice, 2 mm mechanical corneal epithelial debridements were performed, followed by 20 µL of the various treatments to each injured cornea (secretome with HA/CS gel carrier, secretome alone, HA/CS gel carrier alone, and PBS) both right after the debridement and six hours later. After 24 and 48 hours, the corneas were stained with fluorescein and photographed. The wound size was analyzed using Image J.

Secretome concentrations between 7.5 and 1 mg/mL statistically significantly improved cell proliferation. HA/CS alone performed better at higher concentrations. When mixed and applied together, secretome and HA/CS increased cell proliferation and survival at 48 and 72 hours compared to each substance alone. The same result was observed in vivo; while no statistically significant improvement in wound closure was observed for the HA/CS gel and secretome alone compared to saline controls, when the secretome was applied with the HA/CS gel carrier, wound closure was nearly 100% at 24 hours (p<0.01).

The results obtained showed that the hMSC secretome and HA/CS may have additive effects on epithelial cell proliferation and corneal wound closure after mechanical injury compared to either the secretome or HA/CS gels alone.

Example 7

Effects of Secretome and HA/CS on Corneal Wound Healing

Figure 3:
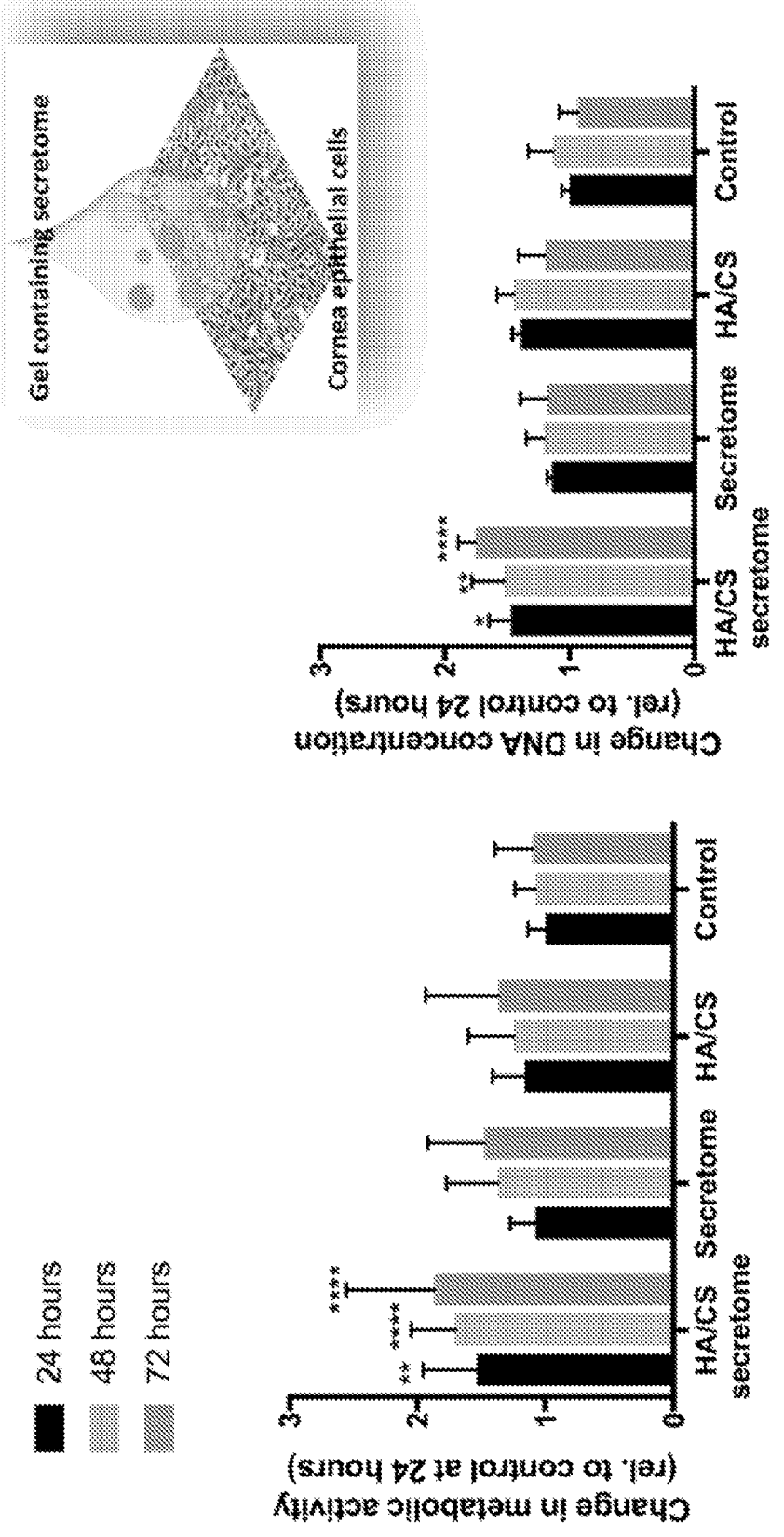
FIG. 3 shows additive effect on primary human cornea cell proliferation treated with both secretome and HA/CS (gel containing secretome). Cell proliferation was measured by the increase in cell metabolic activity and the DNA concentration at 24, 48 and 72 hours. The data was normalized to the no treatment group at 24 hours.

Additive Effects on Primary Human Cornea Cell Proliferation with Treatment with Both Secretome and HA/CS An additive effect on primary human cornea cell proliferation was observed when both secretome and HA were applied to the cells, compared to a positive control (cells grown in complete growth medium). This result was similar to that for rabbit cell data. Secretome concentration was 1.25 mg/mL for all secretome treatments. Gel containing secretome statistically increased cell proliferation at 48, 72 and 96 hours. This additive effect was also evaluated as a change in cell DNA concentrations (FIG. 3). Primary human cornea cell treated with gel containing secretome, increased DNA concentration, which was directly related with the increase in cell proliferation. The increase in the DNA concentration was observed at 48 and 72 hours. No difference was observed at 24 hours comparing to control group.

Mechanical Corneal Wound Model in Rats

Figure 4A:
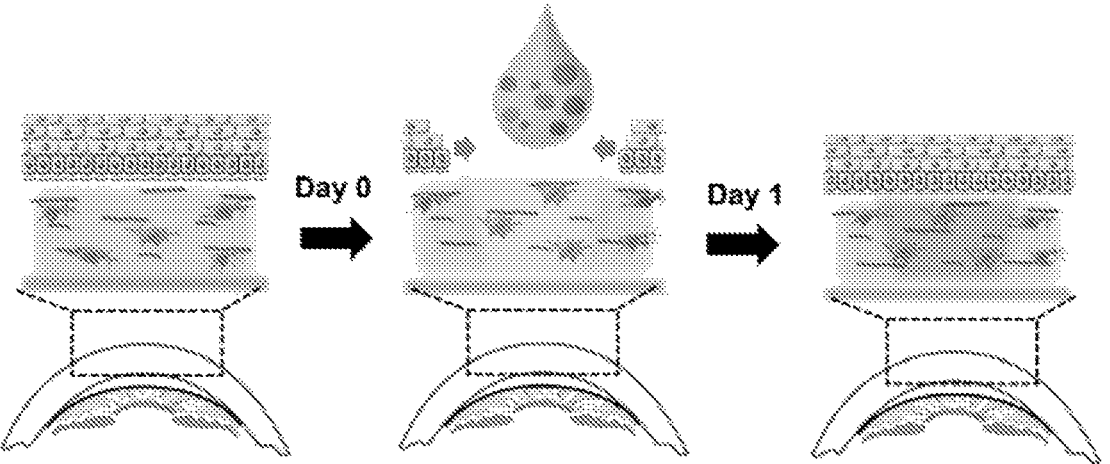
FIGS. 4A-4C show the effects of treatment in a mechanical corneal wound model in rats.
Figure 4B:
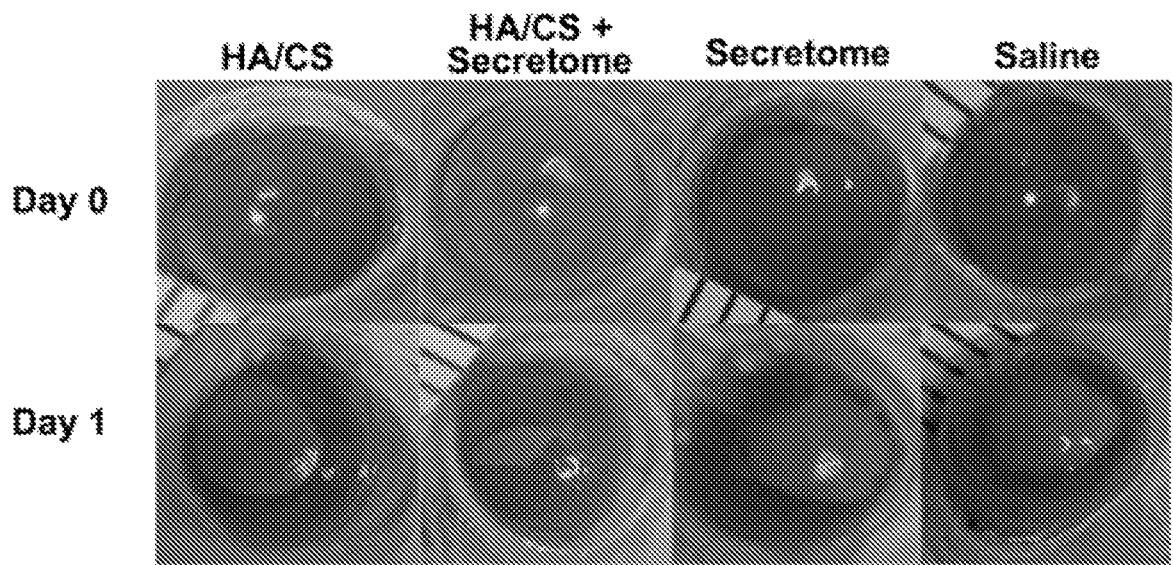
Figure 4B:
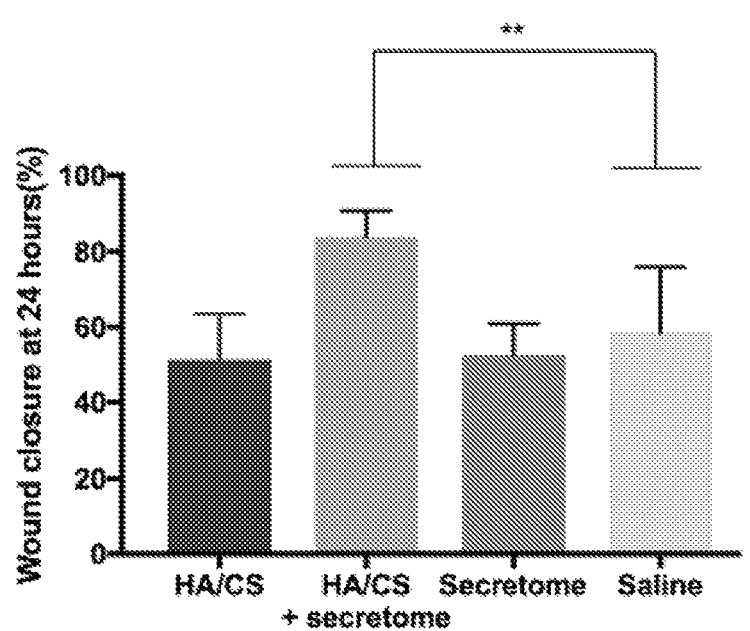
Figure 4C:
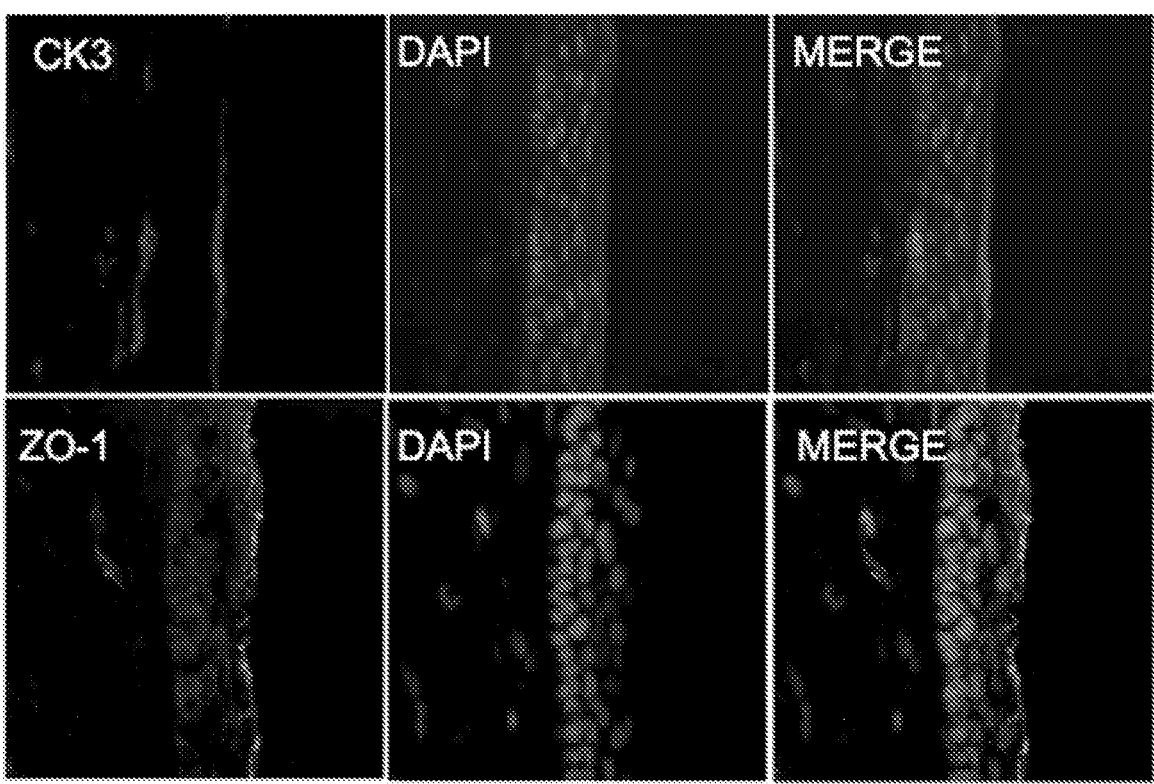

We next aimed to evaluate if the additive effect would occur in pre-clinical models. The cornea epithelium layer from rat was mechanically removed. Twenty-four hours after applying the treatments, the wound closure for the group that received gel containing secretome was around 90%, compared to 50 to 60% for only HA/CS, secretome alone and saline group. The wound closure for the group that received gel containing secretome was statistically significant from the saline group, while the others were not. To evaluate the normal epithelium function after treatment and healing, the cornea was stained with ZO-1 and CK3, markers of epithelial cells. In normal conditions the epithelial layer express CK3 and ZO-1. FIG. 4C shows that these markers were present after treating the cornea with gel containing secretome.

Corneal Alkaline Burn Corneal Wound Model in Rats

Figure 5:
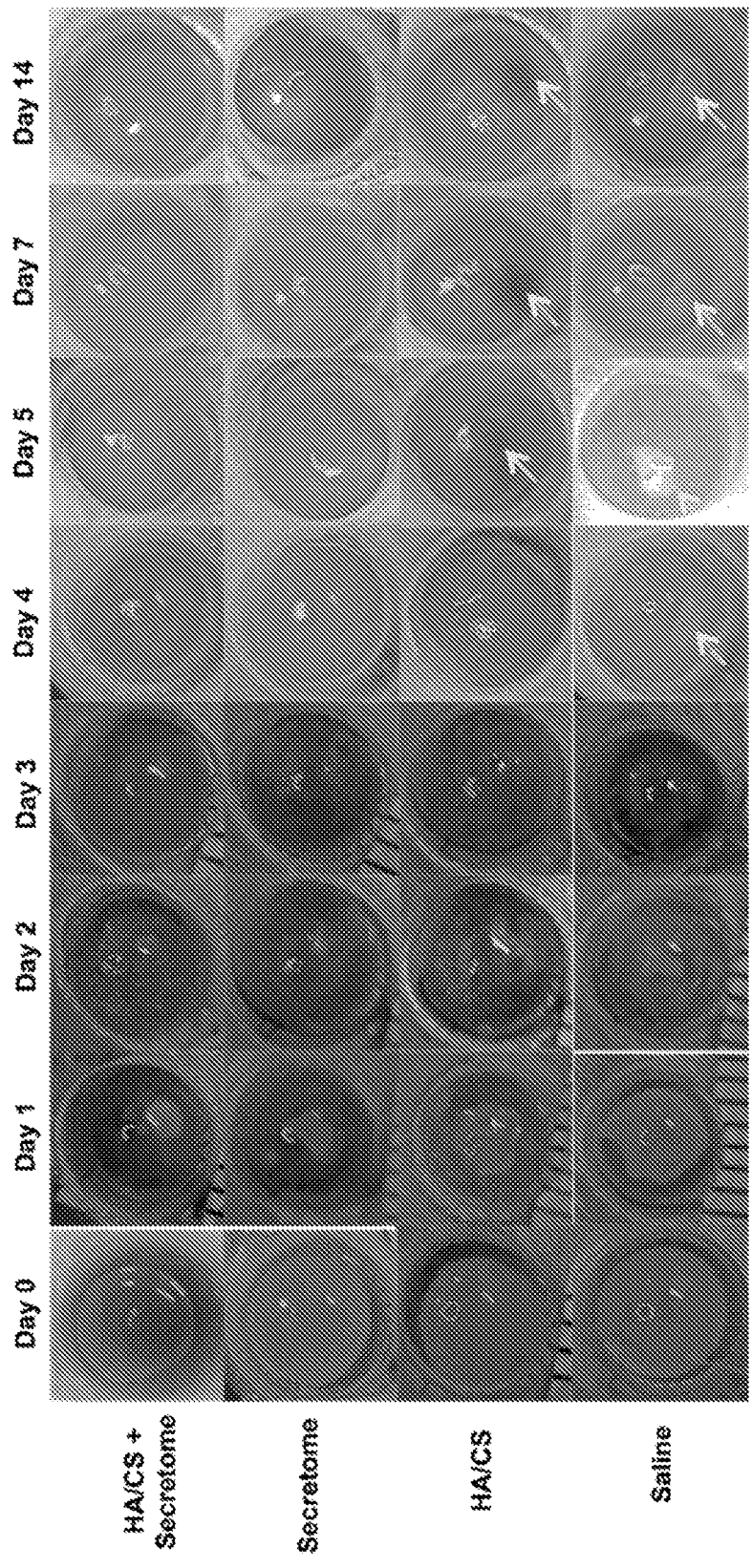
FIG. 5 shows corneal alkaline burn corneal wound model in rats. Sodium hydroxide was applied on the epithelium layer from rat corneas for 1 minute, and then the cornea was stained with fluorescein to evaluate the wounded area. The treatments were applied right after the lesion, 1 drop daily. The wound progression was followed for 14 days.

Sodium hydroxide was applied on the epithelium layer from rat corneas for 1 minute, and then the cornea was stained with fluorescein to evaluate the wounded area. The treatments were applied right after the lesion, 1 drop daily. The wound progression was followed for 14 days (FIG. 5).

After evaluating the wound closure, we continued the evaluation of other cornea problems that are associated with severe inflammation, such as scar formation, neovascularization and hemorrhage. We observed that for gel containing secretome the wound was completely closed at day 2. At day 4, scar formation is observed for the saline group and at day 5 neovascularization with hemorrhage was present in the HA/CS group. The scar formation and hemorrhage got worse every day for 14 days. The groups in which there was no scar formation and hemorrhage were the secretome groups.

Figure 6:
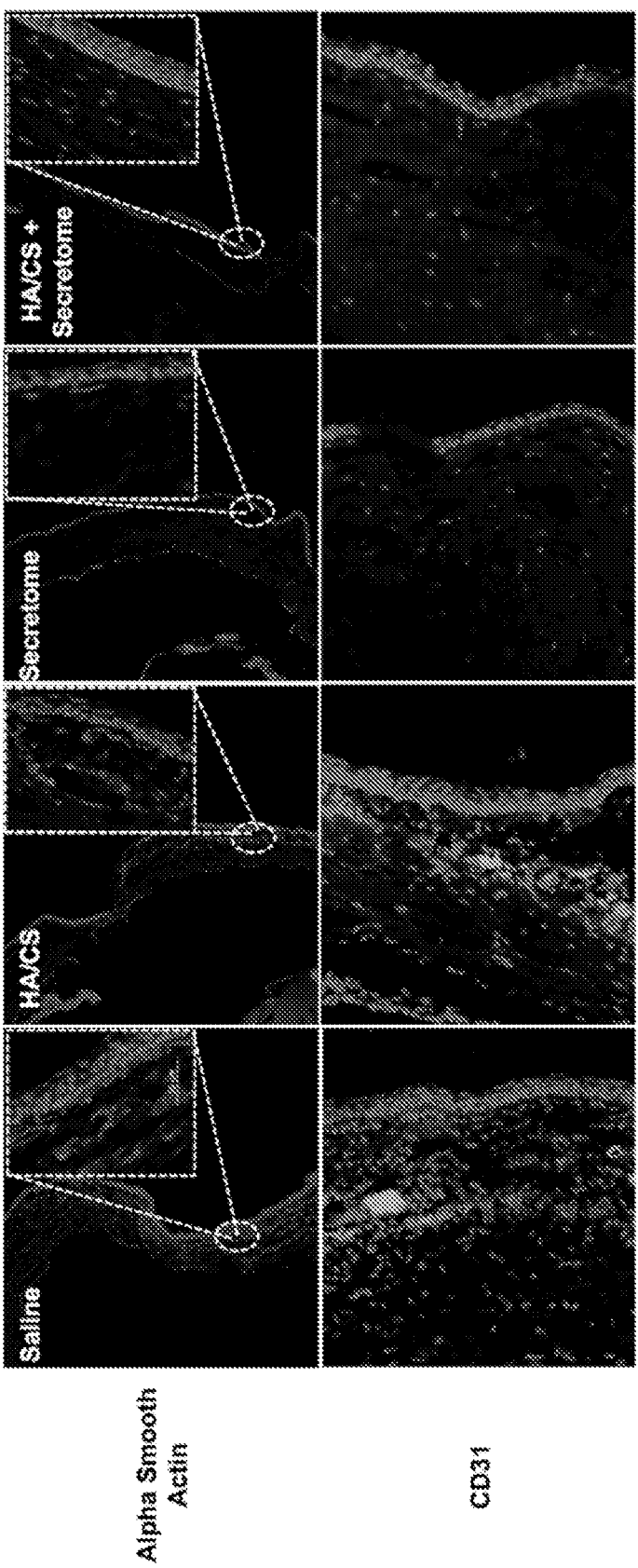
FIG. 6 shows immunostaining of rat corneas 14 days after treatment with gel containing secretome, secretome, HA/CS and Saline. The red color shows alpha smooth actin stain that is a marker for myofibroblasts. Alpha smooth actin stain is observed for HA/CS and saline group. The pink color shows CD31 staining which is a marker for blood cells. CD31 staining is observed for HA/CS and saline group.

Immunostaining of Rat Corneas 14 Days after Treatment with Gel Containing Secretome Treated corneas were stained with alpha smooth actin, a marker for myofibroblasts. Alpha smooth actin staining was encountered in corneas treated with HA/CS and saline, but not for secretome groups (FIG. 6). The transformation of keratocytes into myofibroblasts occurs after a stromal injury. The problem of this transformation is that myofibroblasts do not express GAGs such as keratin sulfate but others that are related to the haze. Treated corneas were stained with CD31, which is a stain for blood cells. CD31 staining was encountered in corneas treated with HA/CS and saline, but not for secretome groups. Blood cells were present in the corneas for the groups that were not treated with secretome.

Mechanical Corneal Wound Model in Rats

Figure 7A:
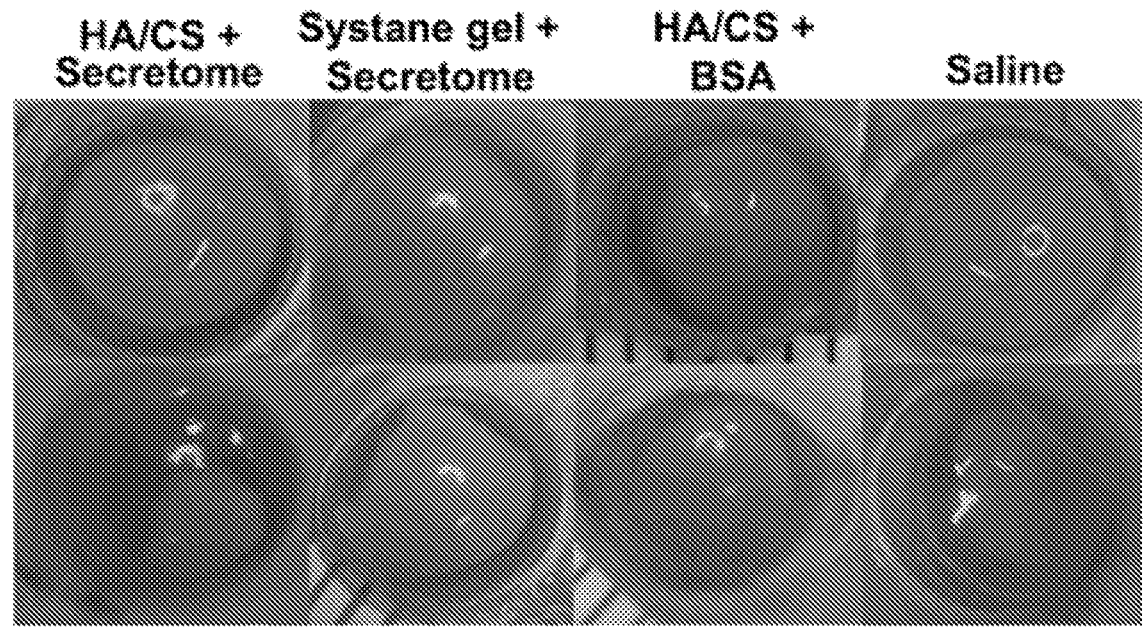
FIGS. 7A-7C show effects of treatment in a mechanical corneal wound model in rats. To evaluate if the additive effect was specific to HA/CS gel or due to the increase of secretome residence time on the cornea surface, different treatments were applied, such as systhane gel with secretome, HA/CS with BSA and gel containing secretome and saline. The treatments were applied right after the lesion, 1 drop daily (FIG. 7A). CD44 expression after treatment with HA/CS containing secretome, secretome, HA/CS and complete growth medium (control) (FIG. 7B). CD44 expression in vivo 7 days after treatment with HA/CS containing secretome, secretome, HA/CS and saline (FIG. 7C).
Figure 7A:
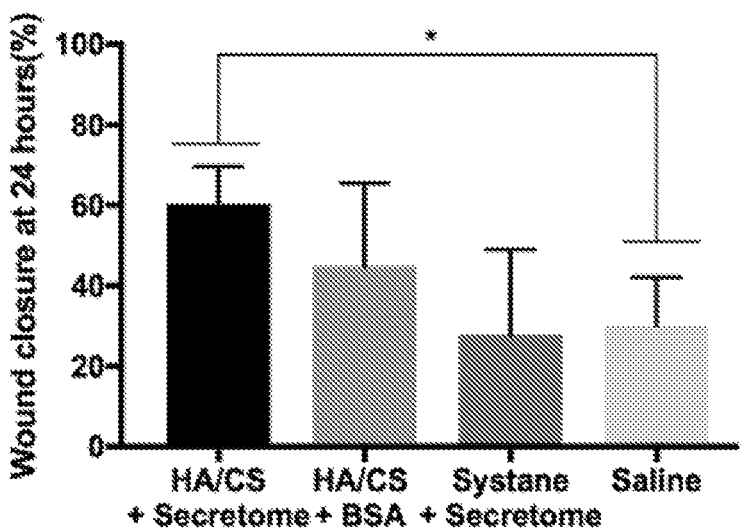
Figure 7B:
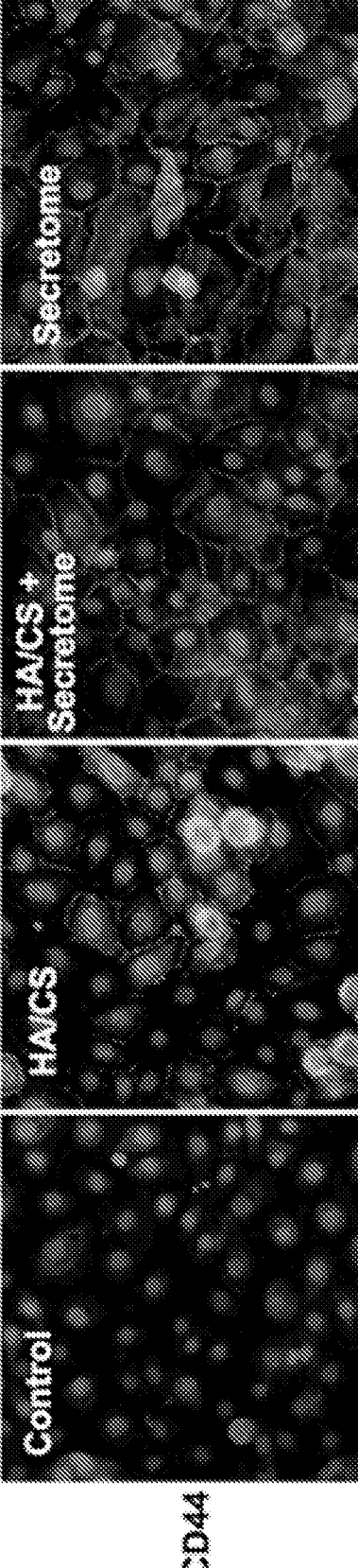
Figure 7C:
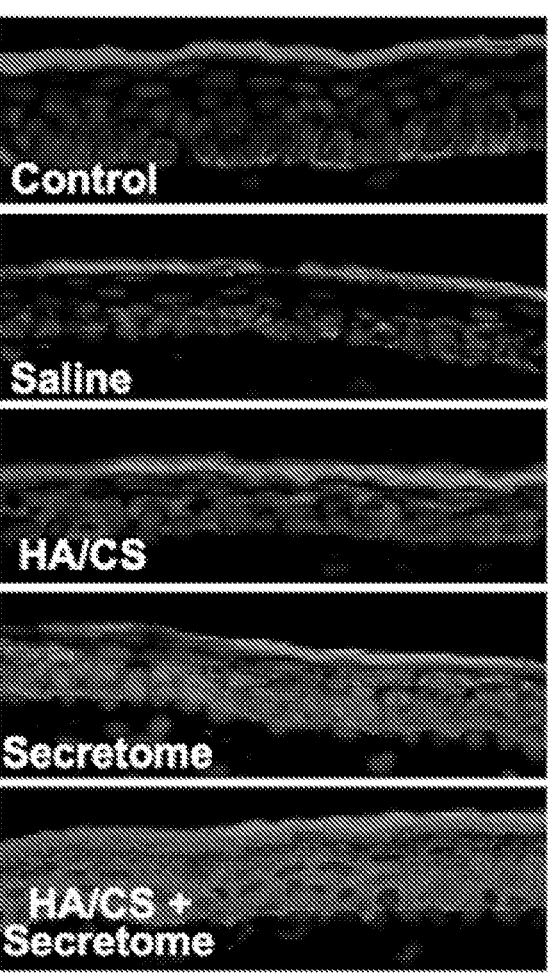

We next aimed to evaluate the mechanism behind the additive effect. We tested the hypothesis if this was due to the increase of secretome time on the cornea surface and if it is specific to HA/CS gel. To answer this question, we performed the mechanical wound model and we applied gel containing secretome, a commercial available gel called systhane with secretome, HA/CS containing BSA and saline group. The results showed that the additive effect is not simply due to the increase of secretome time on cornea surface and that it is specific to HA/CS hydrogel. FIG. 7B shows CD44 expression on primary human corneal epithelial cells. Cells in the control group, showed weak expression of CD44 receptor. In addition, CD44 receptor was not homogeneously distributed to all the cells. After treating the cells with HA/CS, a higher number of cells started to express CD44 receptor compared to the control group. After applying the treatments with secretome, the cells showed an upregulation of CD44 receptor compared to all other groups. CD44 expression was also evaluated in vivo after the mechanical wound in rats (FIG. 7C). In normal cornea, without injury, CD44 receptor is expressed in the basal layer and also in the apical layer. After injury, the saline group showed higher expression of CD44 receptor in the basal layer of the cornea. The HA/CS and secretome group showed an upregulation of CD44 receptors, in the basal layer, compared to injured group treated with saline. The group that received HA/CS with secretome showed an upregulation of CD44 receptors compared to the groups treated with the substances alone.

Discussion

The delivery of secreted factors from human mesenchymal stem cells and the cells themselves have been used in pre-clinical studies as a strategy to enhance corneal wound healing. While few studies have shown the delivery of secretome itself to the cornea surface, the main focus is the subconjunctival application of the hMSCs (Oh et all. Stem Cells 2008; Ke et al. Plos one 2015; Mittal et al. Stem Cell reports 2016; Di et al. IOVS, 207). This is because the delivery of secretome to the cornea surface has limitations with regard to the delivery method. So far, studies have shown the increase in the epithelial cell proliferation and in the wound healing of organ cultured cornea, by the incubation with conditioned medium containing secretome (Wee et al. IOVS 2014; Connon et al. Plos One 2014). Thus, appropriate delivery methods are required in order to enhance secretome biological functions. In this study, we applied secretome to the cornea surface using a hydrogel as a carrier, constituted of hyaluronic acid (HA) and chondroitin sulfate (CS). This hydrogel has important advantages of being biocompatible and has shown beneficial effects on cornea wound healing (Carlson et al. Journal of Ocular Therapeutics and Pharmacology, 2018; Tosi et al. Cornea, 2014). In addition, the combination of HA and CS have been used in ophthalmic viscosurgical devices and as eye drops therapeutic agents (Limberg et al. American Journal of Ophthalmology, 1987). Thereby, the use of a hydrogel can overcome limitations regarding the bioavailability of secretome to the cornea surface. Previous studies showed increased cornea wound healing by the subconjunctival delivery of hMSCs, together with topical application of polysaccharide hydrogel. However, cellular therapy has drawbacks such as cell viability, phenotypic stability, regulatory issues, and high costs. Here, besides of the advantages already mentioned, of each substance individually, we hypothesized that the combination of both secretome and HA/CS hydrogel would have an additive effect, in enhancing cornea wound healing.

In order to determine the best concentration of each substance individually, we performed a titration assay for HA/CS and secretome. The increase in cornea epithelial cell proliferation, compared to the no treatment group, was achieved by using higher concentrations of HA/CS.

Secretome at the highest concentration was toxic to the cells, probably due to the pH (9.0) after diluting in medium. Secretome increased cell proliferation in a dose depended response. We chose to work with the final concentration of 1.25 mg/mL. This concentration statistically increased cell proliferation and required less quantity of secretome lyophilized powder. Then, to determine any cell toxicity that the combination of these substances may provide, we stained live cells with calcein and propidium iodide. We observed that there was no significant cell death compared to control group. Next, to evaluate the additive effect, we treated the cells with gel containing secretome, secretome and HA/CS alone, and complete growth medium. We were able to observe the additive effect that was characterized by an increase in cell metabolic activity and in the DNA concentration, compared to the substances alone and the control group.

We have shown the in vitro additive effect provided by the combination of both secretome and HA/CS hydrogel. To determine if this result would be translated to pre-clinical studies, we performed a mechanical corneal injury model in rats, and then we applied the treatments, one-drop daily, for 2 days. After 24 hours, we observed that the eyes that received saline, secretome and HA/CS had a similar wound closure, of around 60%. In contrast, 90% of the wound was closed for the group that received gel-containing secretome. This result suggested an in vivo additive effect on cornea wound healing, provided by the combination of both secretome and HA/CS. The group that received secretome alone did not show improvement in the rate of re-epithelization, compared to the saline group. Thus, we can suggest that the application of a liquid state substance, on the cornea surface, is not an efficient delivery method, and it would require several applications during the day, to produce positive effects.

Next, we evaluated if the treatment of both secretome and HA/CS would provide a normal re-epithelization. In this regard, we stained the cornea sections with ZO-1 and CK3. ZO-1 is an important epithelial corneal marker because it provides a continuous seal around the cells, preventing the free passage of molecules between adjacent cells. CK3 is a marker of final cornea epithelial cell differentiation, thereby related with normal cell phenotype. We observed that the group treated with gel containing secretome, had a normal epithelial layer phenotype and expressed ZO-1.

We have showed so far that gel-containing secretome had an additive effect in increasing corneal wound healing in a mechanical wound model. Next, we evaluated whether the gel containing secretome would decrease the inflammatory response, by reducing neovascularization and scar formation in a chemical burn wound model. Similarly to the mechanical wound model, we observed that 24 hours after applying the gel containing secretome, 90% of the wound was closed for the group that received the gel containing secretome, comparing to around 50% for the other groups. At day 2, the wound was completely closed only for the group that received gel-containing secretome. In the following days, a severe scar is observed for the saline group, and hemorrhage with neovascularization was present for the HA/CS group. Thus, only for the groups that received secretome, we observed a reduced neovascularization and the absence of scar and hemorrhage. We also stained the cornea for smooth alpha actin and CD31. Smooth alpha actin is associated with keratocytes transformation to myofibroblast and it was intensively present in the corneas treated with saline. This result correlates with our macroscopic analysis of the eyes during 14 days. Myofibroblast formation is associated with scar due to the extracellular matrix produced by these cells (Torricelli et al. Exp. Eye Research, 2016). CD31 staining was present for the eyes treated with HA/CS and saline, thereby confirming the hemorrhage observed macroscopically for HA/CS group. Previous work has shown that secreted factors from hMSC can reduce cornea inflammation and decrease epithelial cells apoptosis (Oh et al. IOVS 2014; Oh et al. Stem Cells 2008). Another showed that hMSC maintained cornea transparency after injury (Mittal et al. Stem Cell Reports, 2006). In this model, we observed that secretome alone did not increase the wound healing rate but reduced neovascularization and scar formation. This is probably due to the study time course, in which secretome was applied every day for 7 days. The novelty of our study is the additive effect observed in the cornea wound healing in the mechanical and chemical burn wound model.

Finally, we aimed to understand the mechanism behind this additive effect. First, we hypothesized that it could be related to the increase of the secretome residence time on the cornea surface. To evaluate this hypothesis, we performed a mechanical wound model and we incorporated secretome in a commercially available gel, systhane gel. After 24 hours, the additive effect was not observed for secretome in systhane gel. This suggests that the additive effect is specific to our gel and it is not simply due to the increase of secretome time to the cornea surface. One could also say that this effect would happen with any other protein that is incorporated to the HA/CS hydrogel. To evaluate this, we added BSA to HA/CS hydrogel. Twenty-four hours later, we saw that HA/CS plus BSA did not increase cornea wound healing.

Secondly, we wondered if this mechanism was related to the CD44 receptors. CD44 receptors are well-characterized transmembrane protein and are the main surface receptor for HA. It has been also reported that CS can bind to CD44 receptors (Esford et al. Journal of Cell Science, 1998). The bound of CD44 to HA induces important biological roles, such as cell proliferation and change in cell cytoskeleton (Warren Knudson and Richard S. Peterson, Chemistry and Biology of Hyaluran, 2004). An interesting fact is that HA does not bind to the CD44 receptors in normal conditions. CD44 can be activated and upregulated by pro-inflammatory cytokines and growth factors (Pure and Cuff Trends in Molecular Medicine, 2001). This activation induces HA bind to CD44 receptors. We have shown the presence of pro-inflammatory cytokines and growth factors in the lyophilized secretome. In this regard we evaluated if the secretome could upregulate CD44 receptors. In normal conditions, corneal epithelial cells express CD44 receptors on cell surface. However, this expression is not homogeneously distributed to all cells. After adding HA/CS, we observed a modest increase of the CD44 receptors expression. The addition of gel containing secretome and secretome, substantially upregulated the CD44 receptors compared to control group. This upregulation was also observed in vivo, 7 days after a mechanical wound model. We and others have shown that normal cornea express CD44 on the basal and apical layer (Zhu et al. British Journal of Ophthalmology 1997). After an injury, the CD44 expression increases for the cells in the basal layer as shown in FIG. 7 and by Yu and collaborators (IOVS, 1998). The application of the HA/CS and secretome in an injured cornea increased CD44 expression, compared to saline group. After applying gel-containing secretome, the CD44 receptors increased in all layers of the cornea, showing an upregulation compared to the other groups. Based on these results, we proposed a mechanism behind this additive effect. In the presence of secretome, CD44 receptors are upregulated and activated inducing HA binding and endocytosis to the cells. Once inside cells, HA is transformed in low molecular weight chains that are responsible for the biological response (Warren Knudson and Richard S. Peterson, Chemistry and Biology of Hyaluran, 2004). In addition, secretome itself contains growth factors that are directly related to cell proliferation.

This work has provided an optimal way to delivery secretome to the cornea surface, through a delivery strategy that not only increases secretome residence time on the cornea surface, but also induces an additive effect in increasing cornea wound healing. In this regard, these promising results could potentially be an alternative to the application of amniotic membrane and autologous serum, in patients with severe cornea disorders.

Example 8

In Situ-Forming Hyaluronic Acid Hydrogel through Visible Light-Induced Thiol-Ene Reaction Here we present hyaluronic acid (HA) hydrogels cross-linked via thiol-ene reaction initiated by visible blue light exposure in the presence of riboflavin phosphate (RFP). The fabrication procedure is rapid and proceeds as effectively with exposure to blue light as it does with UV light. We successfully initiated the thiol-ene reaction by RFP with blue light, which triggered gelation that proceeds over about 5 minutes at 36° C. after an initial small change in modulus upon light exposure. Gel transparency was also evaluated, and the HA gel exhibited over 80% transmittance in the visible spectrum. The degradation and protein release kinetics of the photo-crosslinked HA hydrogel are also presented. The capacity of blue light to initiate thiol-ene reaction was equal to or more effective than UV light of the same energy. The cytocompatibility of hydrogels was evaluated using corneal fibroblasts, and the light-induced fabrication procedure and resultant gel materials did not affect the cell viability. The results indicate that an RFP and BL-based photo-reaction to gelate HA may be an effective and promising modality for applications where in situ gelation is desired.

1. Introduction

Hyaluronic acid (HA) has been extensively studied as a biomaterial for therapeutic applications, and has been used in eye drops as viscosity-increasing agents that improve drug bioavailability by increasing contact time in the pre-corneal space (Eljarrat-Binstock et al. Pharm. Res. 27(4) (2010) 530-543). However, the residence time on the ocular surface is under one hour, and 90% of HA is cleared within half an hour (Mochizuki et al. Br. J. Ophthalmol. 92(1) (2008) 108-111). Crosslinking is one way to increase the residence time of macromolecules and can be accomplished through a variety of means, including the free radical crosslinking of acrylic pendant groups using UV light and a photo-initiator (Marklein et al. Soft Matter 6(1) (2010) 136-143, Ma et al. Chem. Commun. 50(1) (2014) 112-114). Thiol-ene chemistry is a highly efficient reaction between a thiol and an alkene to form an alkyl sulfide that is not mediated by free radicals and has been used to crosslink conjugated HA and other biomolecules (Gramlich et al. Biomaterials 34(38) (2013) 9803-9811, Mergy et al. J. Polym. Sci., Part A: Polym. Chem. 50(19) (2012) 4019-4028). Light-induced thiol-ene reactions (so-called "photo-click chemistry") using UV light have been developed as a crosslinking method to maintain the bioactivity of cross-linked proteins while also providing spatial and temporal control over the reaction (McCall et al. Biomacromolecules 13(8) (2012) 2410-2417, Hoyle et al. Angew. Chem. Int. Ed. 49(9) (2010) 1540-1573). Certain naturally occurring, photosensitive molecules have been explored for the purpose of crosslinking biomolecules. Eosin-Y activated by green light has also been shown to mediate thiol-ene crosslinking of HA and exhibit in vitro cytocompatibility (Shih et al. Rapid Commun. 34(3) (2013) 269-273). Rose Bengal has been studied as well, as a mediator of collagen crosslinking upon exposure to green light (Cherfan et al. Invest. Ophthalmol. Vis. Sci. 54(5) (2013) 3426-3433). Riboflavin phosphate (RFP), a water-soluble form of riboflavin also known as vitamin B2, has been studied extensively as a photo-initiator and was approved in 2016 by the FDA for crosslinking of collagen with UV light (Spoerl et al. Cornea 26(4) (2007) 385-389). We recently reported the use of blue light to trigger the crosslinking between heterologous proteins (growth factors and collagen) via photoactivation of RFP (Fernandes-Cunha et al. Biomacromolecules 18(10) (2017) 3185-3196).

We present here the use of blue light (BL) to trigger gelation of HA via the thiol-ene reaction between methacrylated (MA-HA) and thiolated HA (SH-HA). The system exhibits an interesting gelation delay behavior, where the gelation is triggered but not completed during the BL exposure interval (20-40 seconds), and instead the gelation reaction takes place over several minutes. This provides some optionality over how the gel could be applied in various research or clinical settings, where direct light exposure over cells or tissues may not be desired. At the same time, we chose to study BL as an alternative illumination source to UV due to its safe and ubiquitous use in ophthalmology as a diagnostic aid in combination with fluorescein dyes to evaluate corneal disease and injury, to measure intraocular pressure, and to perform retinal vascular angiography. RFP was added to a mixture of MA-HA and SH-HA solution as a photo-initiator. Due to its success as a photo-initiator for unconjugated natural collagen, we hypothesized that it could be used to accelerate thiol-ene reaction as well, which are known to be photosensitive. The triggering capability of BL was compared to UV, and the rheological properties, transparency, degradation characteristics, protein release, and cytocompatibility were evaluated.

2. Experimental 2.1. Materials

Unless otherwise noted, all chemicals and solvents were of analytical grade and used as provided by the manufacturers. Methacrylated HA and thiolated HA were purchased from Vornia Biomaterials (Tallaght, Dublin, Ireland). Riboflavin phosphate (RFP), phosphate-buffered saline (PBS), bovine serum albumin (BSA), 1,9-dimethylmethylene blue (DMMB), ethanol, glycine, sodium chloride, hydrochloric acid, Pierce BCA protein assay kit, gelatin, collagen, fibronectin, dimethyl sulfoxide (DMSO), Cholera Subunit A, and insulin were purchased from Sigma-Aldrich (St. Louis, MO, USA). Dulbecco's phosphate-buffered saline (DPBS), antibiotic-antimycotic, Dulbecco's modified eagle medium/nutrient mixture F-12 (DMEM/F-12) with 4-(2-hydroxyethyl)-1-piperazineethanesulfonic acid (HEPES), fetal bovine serum (FBS), epidermal growth factor (EGF), and LIVE/DEAD viability/cytotoxicity kit were purchased from Thermo Fisher Scientific (Waltham, MA, USA).

2.2. Fabrication of HA Gels by Light-Induced Thiol-Ene Reaction

Methacrylated HA (MA-HA) and thiolated HA (SH-HA) were dissolved in PBS as 10 mg/mL, and then the solutions were mixed as 1:1 ratio. The riboflavin dissolved in PBS and added to the mixed HA solution. 20 s of UV and 40 s of blue light (BL) were exposed through 3 W UV LED Spot Cure system (Doctor UV, Redondo Beach, CA, USA) and commercial 1.5 W dental LED curing light, respectively.

2.3. Characterization of HA Gels

FTIR spectra were recorded on a Nicolet iS50 FTIR spectrometer (Thermo Fisher Scientific, Waltham, MA, USA) at Stanford Soft & Hybrid Materials Facility (SMF, Stanford, CA, USA). MA-HA and SH-HA were measured as powder provided by without dissolving in PBS. The HA gels were gently dried at room temperature and then measured.

Rheology of HA gel was evaluated by ARES-G2 rheometer (TA Instruments, New Castle, DE, USA) at SMF. The UV or BL was exposed after the HA and RFP mixture solutions were mounted on the plate, and then the rheometer ran immediately. To determine gelation time, sweeps were performed at 36° C. for 1800 s at 1% strain and 1 Hz oscillatory frequency. To evaluate definitive storage and loss moduli of gels, the samples were incubated at 36° C. overnight after light exposure, and then frequency sweeps from 0.1 to 10 Hz with a fixed 1% stain were performed.

The absorbance spectra from 300 to 700 nm of RFP and resultant HA gels in 96 well plates were measured using SpectraMax M Series Multi-Mode Microplate Reader (Sunnyvale, CA, USA). The gel samples were fabricated in 96 well plate from 100 μL of precursor solution with light exposure. After absorbance measurement, 150 of PBS was added to each well and incubated. The absorbance spectra were measured after 24 hours with removing incubation solution. The procedure was repeated and measured at 48 hours.

2.4. Degradation of HA Gels and BSA Release

For evaluation of HA gel degradation and BSA release, the BSA was added to the HA and RFP solution, and gels were fabricated in 24 well plates. After a 30 minute incubation at 36° C., the gels were rinsed with PBS, and the washing solution was collected at day 0. Fresh PBS was added to each well and incubated at 36° C. The collection and incubation were repeated at certain days until day 21.

The degraded HA was quantified using a DMMB assay. DMMB was dissolved in ethanol as 3.2 mg/mL and incubated overnight at room temperature. Hydrochloric acid was added to DI water to make pH 3.5, and then glycine and sodium chloride were added to make 40 mM, respectively. The DMMB and acidic solutions were mixed with 1:199 ratio to make DMMB assay working solution. In 96 well plate, 25 μL of collected sample solution with 10-time dilution and 200 μL of DMMB assay working solution were mixed and measured absorbance immediately.

The released BSA was quantified using BCA protein assay. We followed the BCA protein assay kit protocol to make BCA protein assay working solution. In 96 well plate, 25 μL of collected sample solution without dilution and 200 μL of BCA protein assay working solution were mixed and incubated for 30 minutes at 36° C.

The absorbance was measured using SpectraMax M Series Multi-Mode Microplate Reader. After the standard curves of HA and BSA solutions were measured, and the amounts of HA and BSA were accumulated and divided by initially added amounts.

2.5. Cell Culture and Viability Assay

Primary corneal fibroblasts were obtained from rabbit corneas. Plates were precoated with a solution of collagen and fibronectin (1:1) and BSA (1%) for 1 hour at 37° C. Rabbit eyes were washed with DPBS, in the presence of antibiotic-antimycotic. The endothelial layer was removed, and the corneas were placed side up on a sterile surface and cut into triangular wedges. The cornea was then placed upside down on the precoated plates. The tissue was allowed to dry for 20 minutes, and then one drop of DMEM/F12 with HEPES, FBS (15%), DMSO (0.5%), Cholera Subunit A (1 μg/mL), EGF (10 ng/mL), and insulin (5 μg/mL) was added to each segment. On the next day, 1 mL of medium was added to each well. After confluence, the cells were subcultured and used at passage two.

To evaluate cytotoxicity of HA gels, the mixture of MA-HA, SH-HA, and 0.01% RFP was prepared. After UV or BL exposure, 100 μl of precured solution was applied to each well of 24-well plates. After incubation for 30 min at 37° C., $1 \times 10^4$ cells/cm$^2$ were seeded and incubated overnight. The cell viability was assessed via LIVE/DEAD staining following the manufacturer's instructions. The plates were mounted and observed using laser scanning microscope (ZEISS LSM 880, Carl Zeiss Ag, Oberkochen, Germany).

Figure 8:
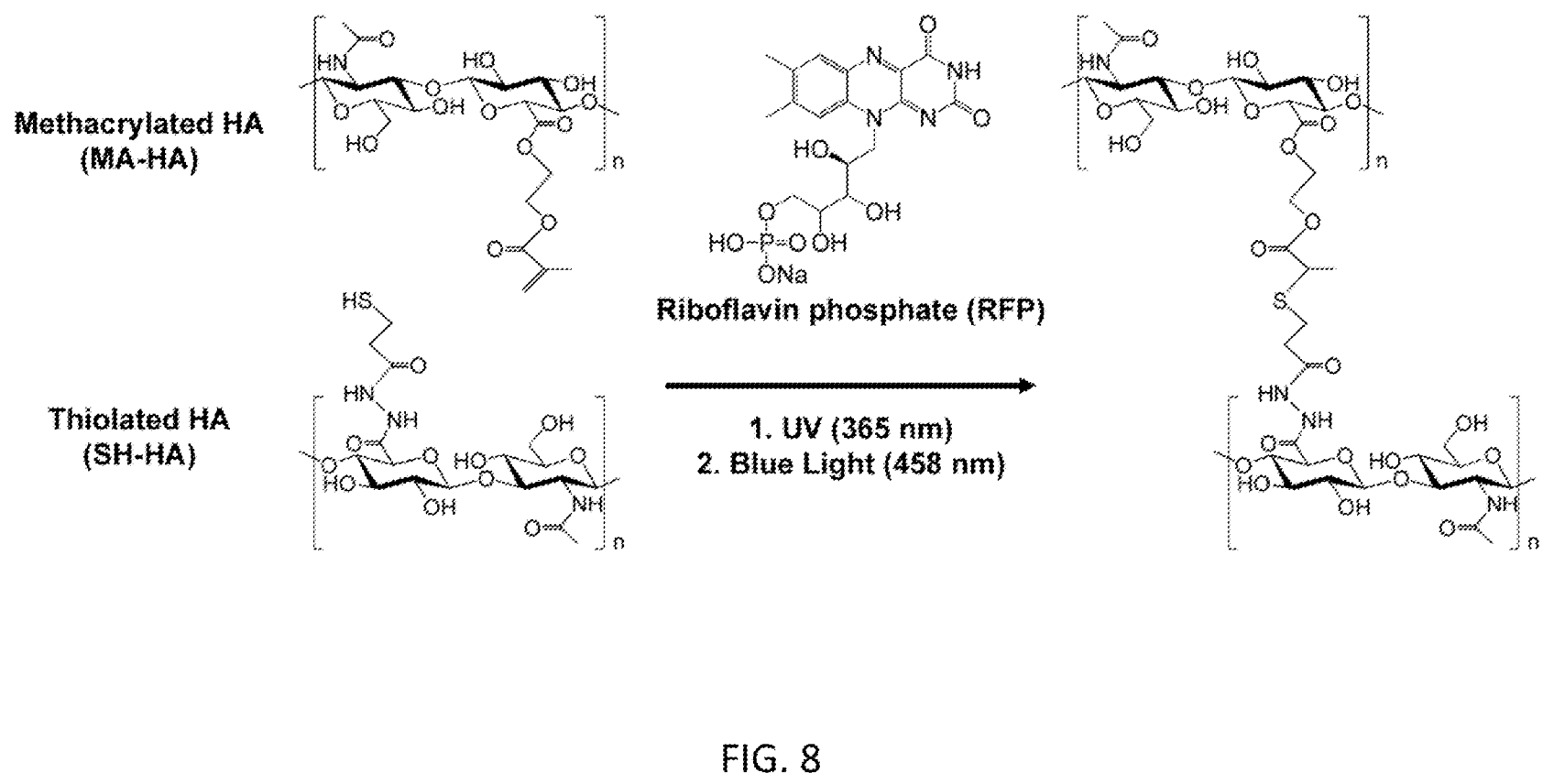

3. Results and Discussion 3.1. HA Gel Formation by Light-Induced Thiol-Ene Reaction In this study, we investigated the use of BL to crosslink conjugated HA through thiol-ene photochemistry. We hypothesized that a light-induced thiol-ene reaction could be used to rapidly form HA gel. The methacrylate and thiol group were utilized for light-induced thiol-ene reaction, and the functionalized HA by the two chemical groups were commercially available. RFP was introduced as a photo-initiator for thiol-ene reaction, and then either BL and UV lights were used to irradiate the solution to form the alkyl sulfide bond (FIG. 8). Our proposed procedure provides the use of BL, but the UV was also used to be compared. Of note, RFP has two absorbance peaks at wavelengths of 370 and 445 nm (FIG. 9A) and thus absorbs visible light in the blue spectrum as well as light in the UV spectrum. A commercial dental LED curing light was used as the BL source (FIG. 9B) while a UV LED Spot Cure system was used as the UV light source.

Figure 9A:
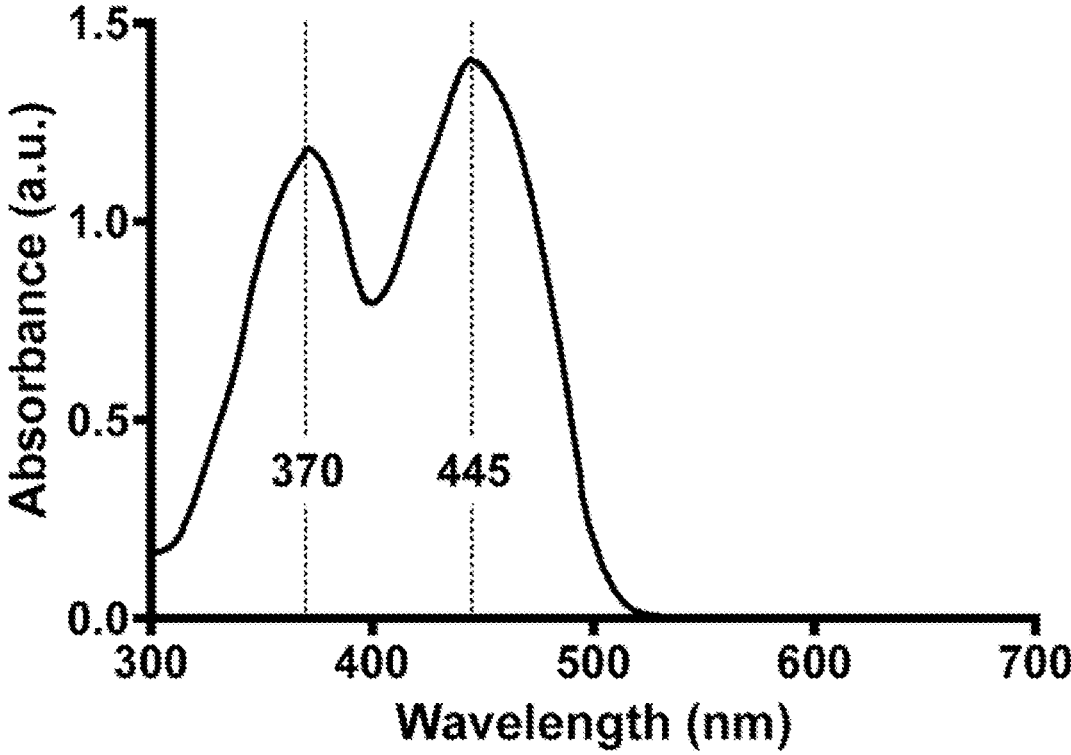
FIG. 9A shows the absorbance spectrum of RFP.
Figure 9B:
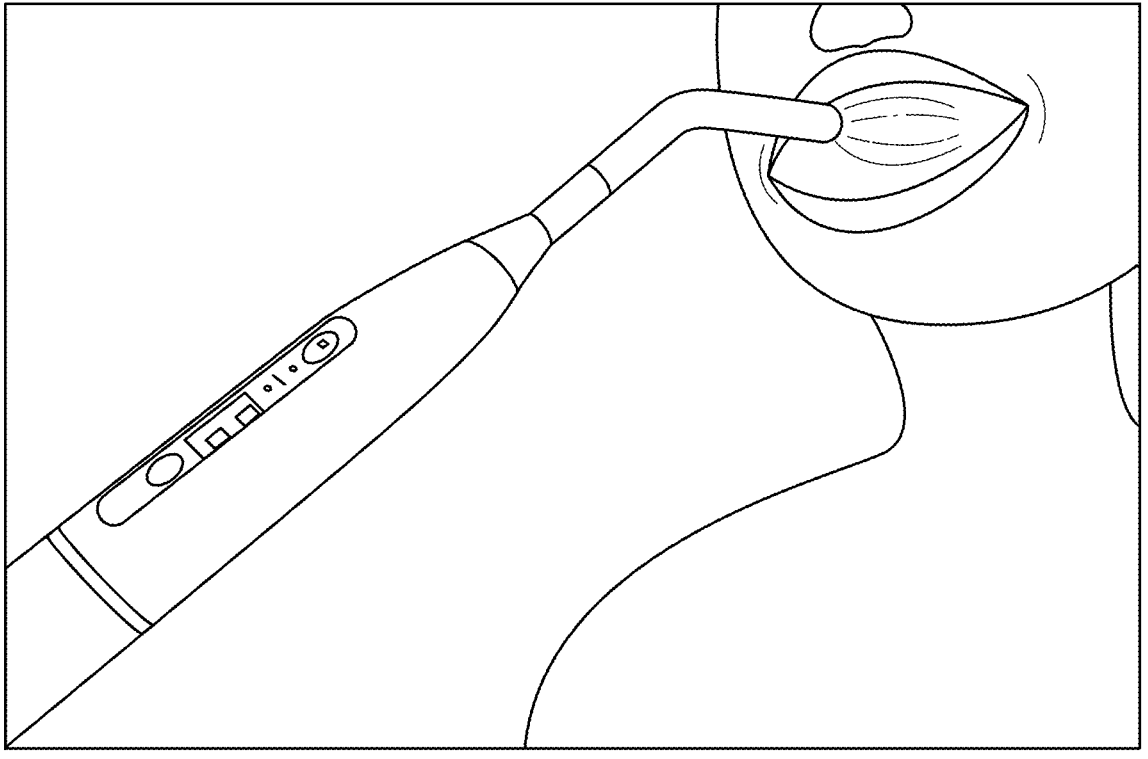
FIG. 9B shows the photographic image of LED dental blue light. The tip of light source was wrapped with paper to prevent light spreading.

Here, we introduce the combination of RFP and BL to initiate the thiol-ene reaction. RFP and UV have been used to strengthen the mechanical properties of the cornea through crosslinking of the collagen matrix (Spoerl et al. Cornea 26(4) (2007) 385-389, McCall et al. Invest. Ophthalmol. Vis. Sci. 51(1) (2010) 129-138). Although the FDA-approved method used in the clinic applies UV light as the energy source, we use BL here, which we showed previously to be effective at inducing crosslinks between collagen and growth factors (Fernandes-Cunha Biomacromolecules 18(10) (2017) 3185-3196). UV exposure of RFP generates singlet oxygen in an oxygenated environment, a phenomenon which has been applied to produce crosslinking of corneal tissue (McCall et al. Vis. Sci. 51(1) (2010) 129-138). We hypothesized that BL near 445 nm activates RFP in the same way that UV light does (FIG. 9A). In this study, UV (3 W/cm$^2$) and BL (1.5 W/cm$^2$) were applied, and we compared the effect of the light source on the photo-click chemistry reaction and gel formation. To provide the same light energy for the thiol-ene reaction, the light exposure times were set to 20 and 40 seconds for UV and BL respectively.

Figure 10:
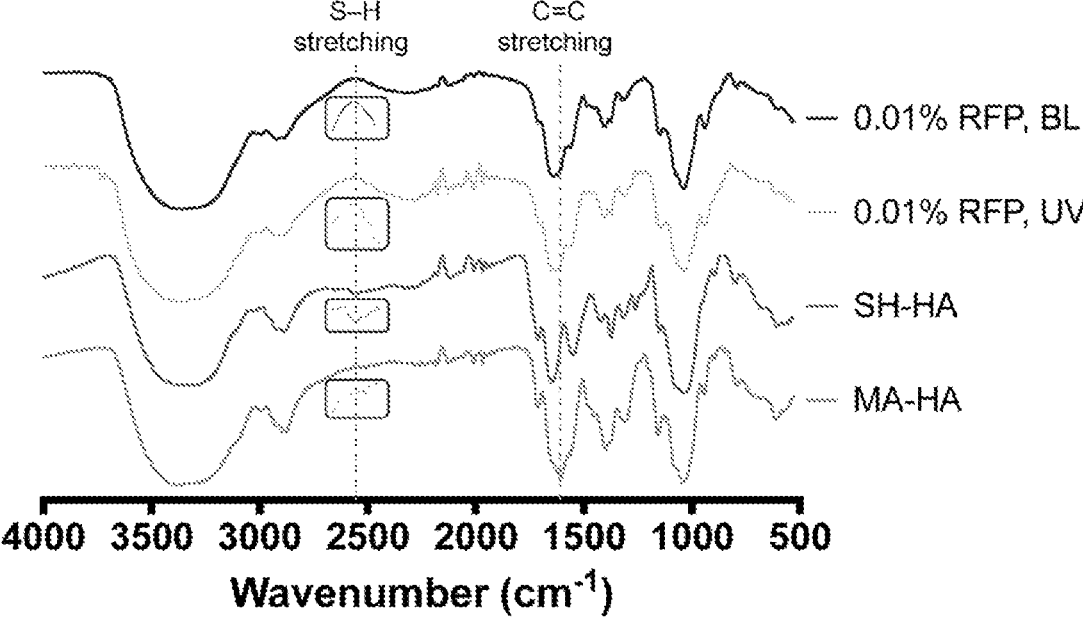
FIG. 10 shows FTIR spectra of hyaluronic acid before gelation (MA-HA, HA-HA) and after gelation by photoclick chemistry with UV and BL.

Fourier transform infrared (FTIR) spectra were acquired to monitor the reaction between the thiol and methacrylate (FIG. 10). Generally, the S—H peak of FTIR is weak, but we could observe S—H signal at 2550 cm$^{-1}$ from SH-HA. The thiol peak disappeared after the light-induced thiol-ene reaction, indicating its consumption during the reaction. The C=C signal from the methacrylate was observed at 1610 cm$^{-1}$, and the peaks were slightly reduced but remained after light exposure. There was no difference between the gels by photo-click chemistry with UV and BL.

The FTIR result showed that the change in the spectrum of the thiol group was greater than that of the methacrylate group before and after the thiol-ene reaction, indicating that the thiols were more consumed than the methacrylates (FIG. 10). The degrees of substitution for MA-HA and SH-HA were 46% and 63%, so all methacrylate should be consumed if the thiol-ene reaction was completed. The fact that the methacrylate peak remained after the reaction suggests that not all the methacrylates were consumed by the reaction. It can be seen that not all thiol and methacrylate were involved in the reaction. This is likely due to the fact that methacrylate is more stable than thiols in air or aqueous environments, so unreacted methacrylate remains after the thiol-ene reaction while unreacted thiol is oxidized to form disulfide bonds. Also, there were no differences between gels formed by UV and BL, which means that BL accelerated the thiol-ene reaction to the same extent that UV did.

3.2. Dynamic Moduli of HA Gels by Light-Induced Thiol-Ene Reaction

Figure 11A:
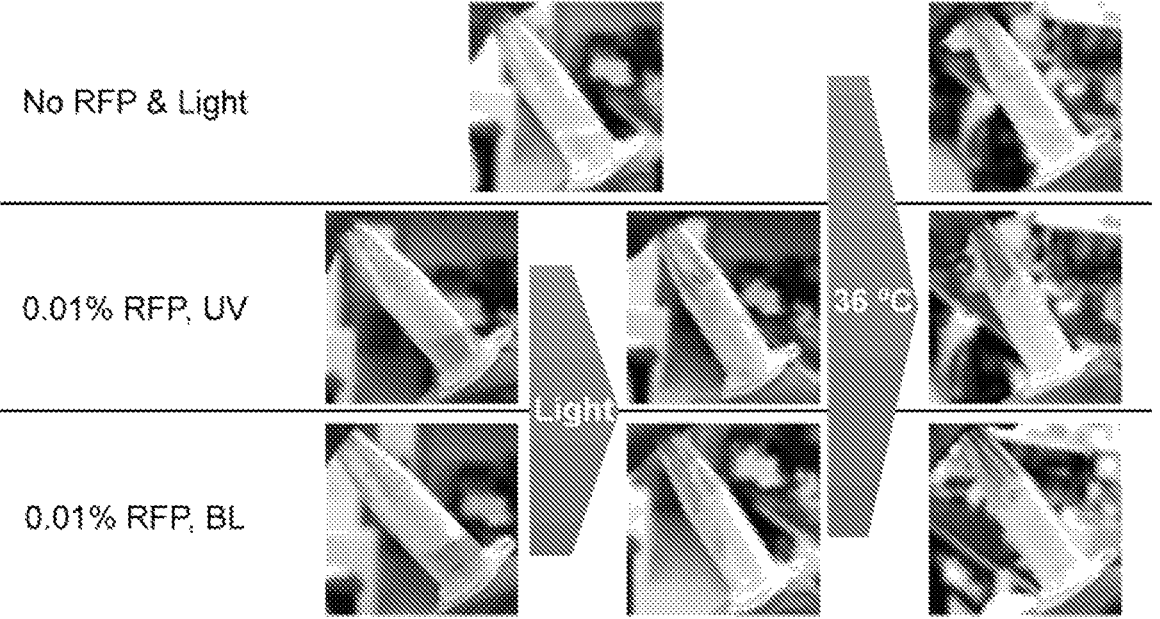
FIG. 11A shows photographic images of resultant HA gels. The 'No RFP & Light' group included MA-HA and SH-HA, and light was not applied. For light-induced thiolene reaction, 0.01% RFP was added to the mixture of MA-HA and SH-HA, and then UV and BL lights were exposed respectively. Dynamic moduli (G': storage moduli, G": loss moduli) as a function of (FIGS. 11B, 11D, and 11F) time and (FIGS. 11C, 11E, and 11G) frequency of HA gels by light-induced thiol-ene reaction with (FIGS. 11B and 11C) 0.01%, (FIGS. 11D and 11E) 0.1%, and (FIGS. 11F and 11G) 0.001% RFP.

The HA mixture of MA-HA and SH-HA without RFP showed the same solution state after incubation for 15 minutes at 36° C., while light-exposed HA mixture with RFP gradually formed gels (FIG. 11A). After UV or BL exposure in the presence of RFP, the solution started to form gel partially, which had slightly flowable property (yellow background region). Following incubation for 15 minutes at 36° C. let the gelation completed by both UV and BL, and there was no significant difference macroscopically (green background region).

Figure 11B:
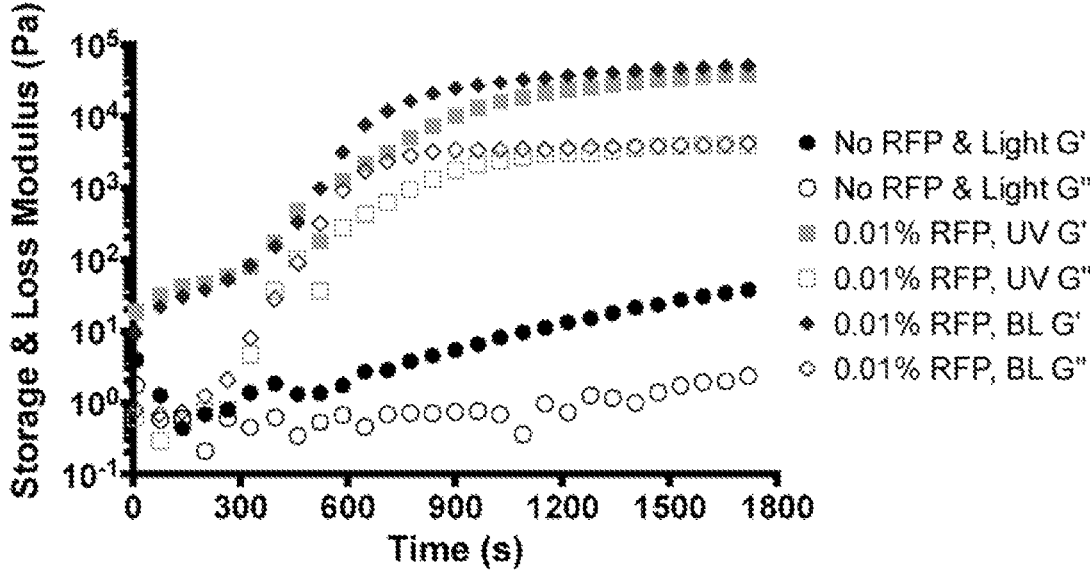
Figure 11C:
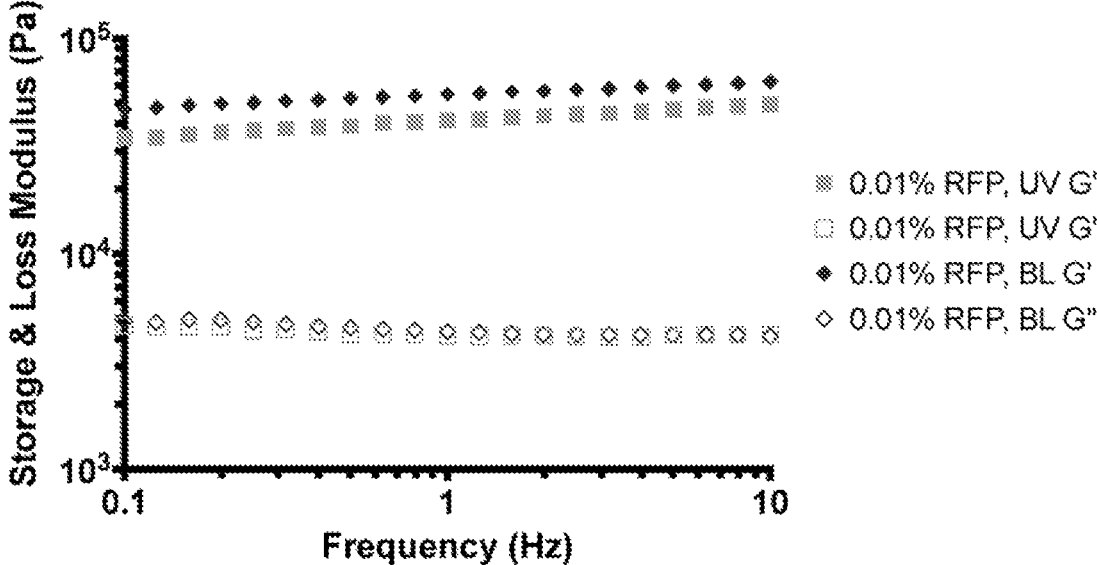

The dynamic moduli changes by crosslinking of HA molecules were measured at 36° C. as a function of time without additional light exposure (FIG. 11B). The mixture solution of MA-HA and SH-HA without RFP and light exposure showed gradually increased storage modulus, and it reached 40.52 Pa in 1800 s. The storage modulus was higher than loss modulus during incubation at 36° C., but there was no drastic increase of dynamic moduli. On the other hands, the gelation kinetics of light-induced thiol-ene reaction with RFP as a photo-initiator showed delayed and steeply increased moduli during incubation. Regardless of light wavelength, the mounted samples showed higher storage moduli than loss moduli (UV G': 18.7 Pa, UV G": 0.8 Pa; BL G': 5.4 Pa, BL G": 0.6 Pa), which means that the samples exhibit elastic behavior as a result of crosslinking. After about 300 seconds, the moduli of gels were drastically increased. Upon UV exposure, the rate of increase of dynamic moduli and storage moduli at 1800 s were relatively lower than that observed with BL exposure (UV: 39.8 kPa; BL: 52.5 kPa). The storage and loss moduli of crosslinked HA gel by UV and BL were measured as a function of frequency, and both gels maintained their viscoelastic behavior in 0.1-10 Hz, which indicates completion of the gelation reaction (FIG. 11C).

Figure 11D:
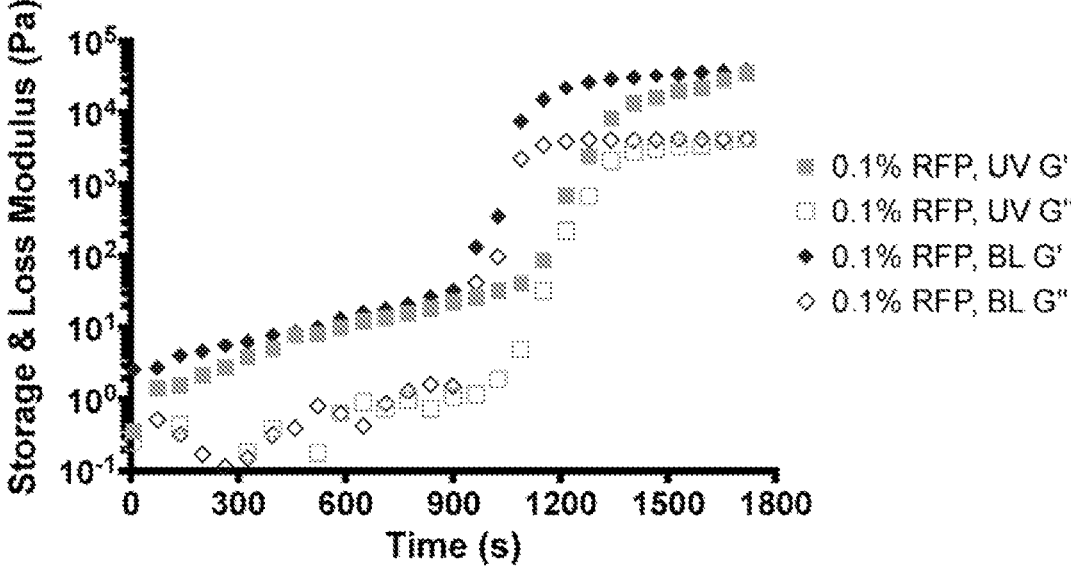
Figure 11E:
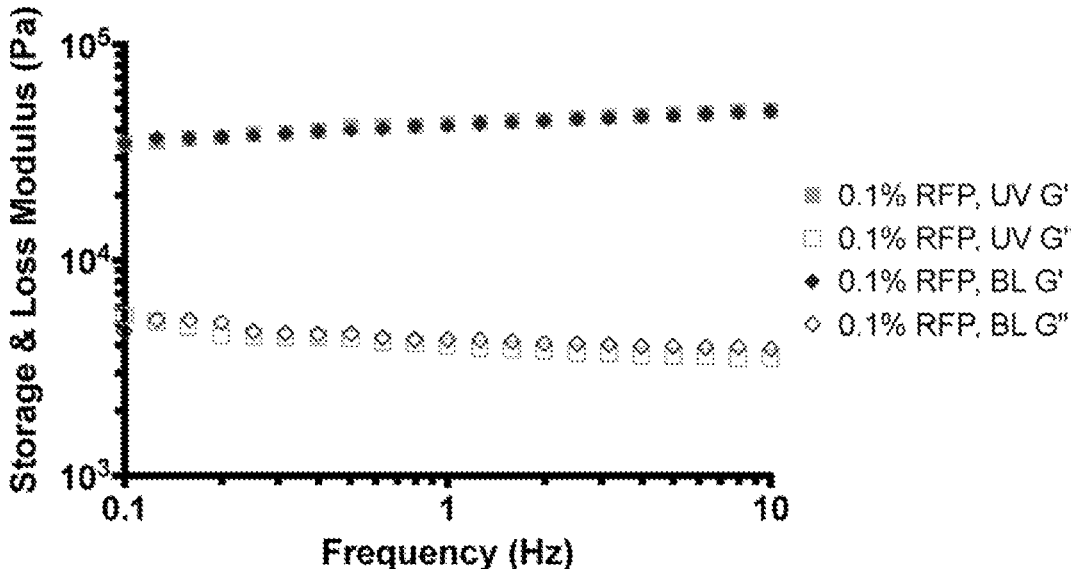
Figure 11F:
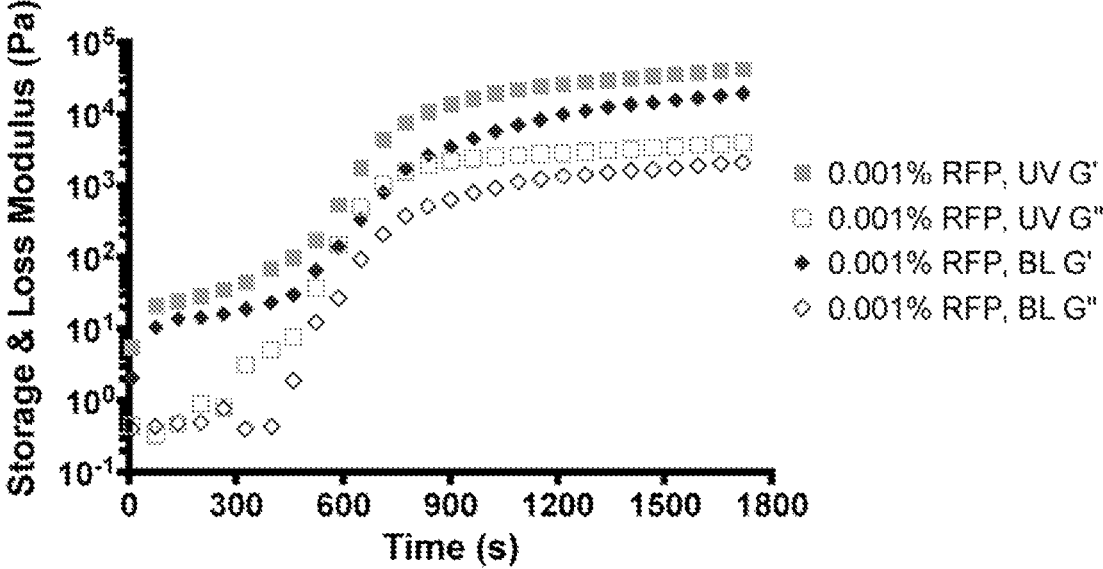
Figure 11G:
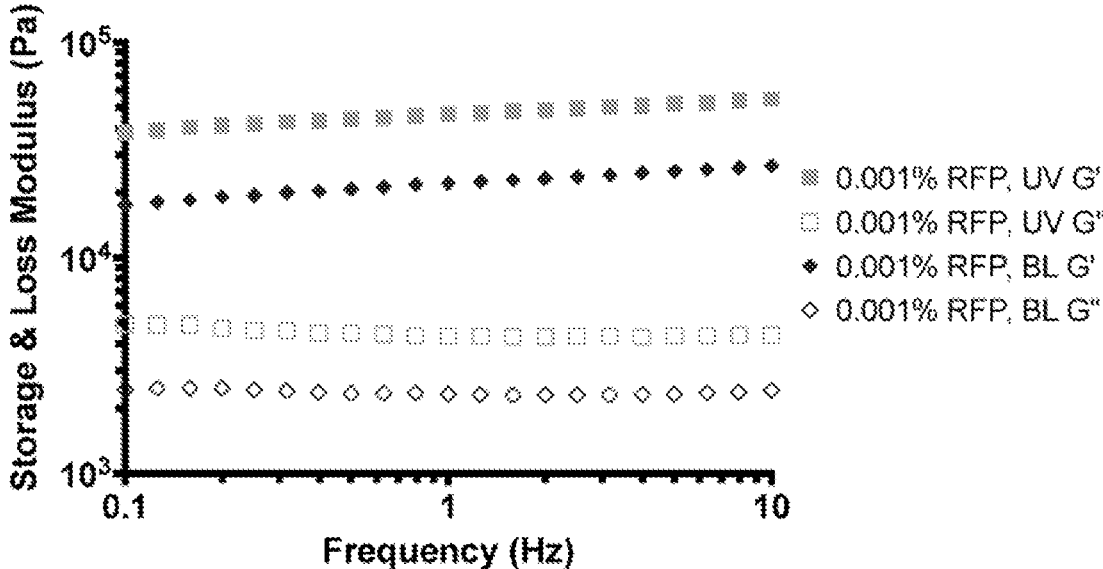

We measured the dynamic modulus with different concentrations of RFP (FIGS. 11D and 11F). The gelation of solutions including 0.1 and 0.001% RFP was completed within 1800 s similar to 0.01%, but the starting time points of the observed modulus increases were slightly different. The moduli of the HA solutions including 0.001% RFP started to increase near 300 s after light exposure drastically, and the point moved to about 900 s for 0.1% RFP. Also, immediately after light exposure, although the 0.1% concentration was highest, it showed low storage and loss moduli (UV G': 0.4 Pa, UV G": 0.3 Pa; BL G': 2.6 Pa, BL G": 0.1 Pa). The effects of RFP concentration were evaluated, and the 0.1% RFP showed a delay in the point at which modulus increases (FIG. 11D). This suggests that the yellow color of RFP in solution could affect the efficiency of reaction due to reduced light penetration. The 0.1% RFP was excessive for the thiol-ene reaction between MA-HA and SH-HA, so it not only initiated the reaction but also interfered with the transfer of light. Nevertheless, there were no big differences on the storage moduli after gelation compared to 0.01% RFP (FIG. 11E). Although the storage moduli of UV/BL-induced gels from 0.001% RFP showed over 10 kPa, the resultant gels were not completely formed (FIG. 11G).

Figure 15:
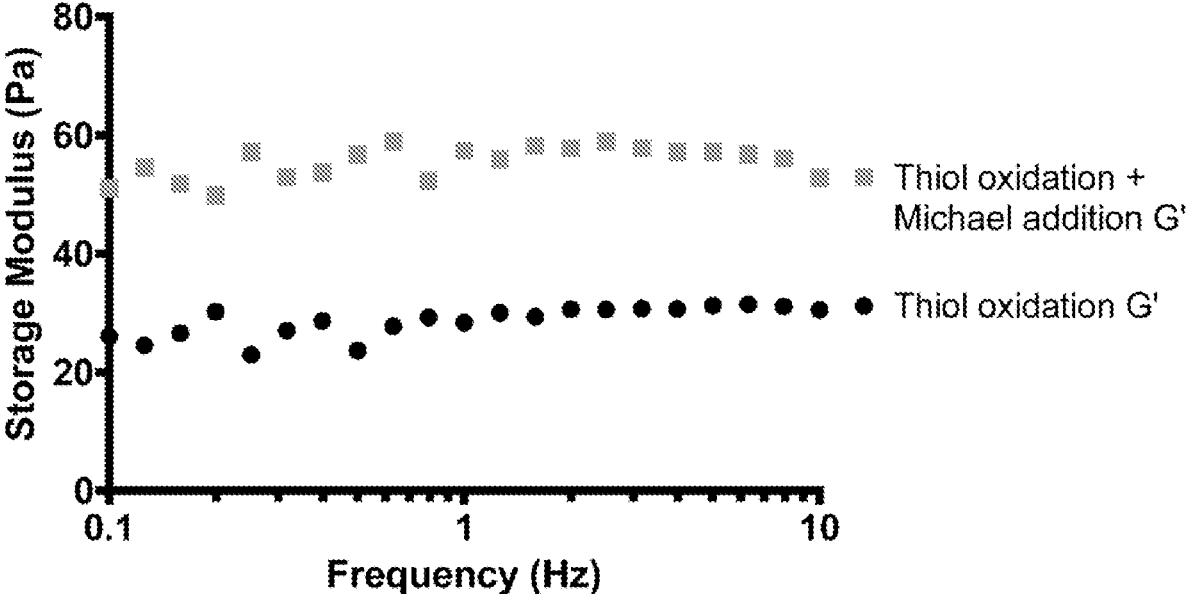
FIG. 15 shows storage moduli of HA gels formed by thiol oxidation and thiol oxidation with Michael addition.

The gelation of MA-HA and SH-HA without RFP and light was not observed macroscopically (FIG. 11A), but there were increases of dynamic moduli from the mixture without light mediation (FIG. 11B). The increase in storage modulus is a result of two crosslinking reactions in the mixture solution. The first reaction is the formation of disulfide bonds via oxidation of thiol groups. The second reaction is Michael addition pathway between thiol and methacrylate groups, where thiolate anion addition to the electron-deficient carbon-carbon double bond occurs (Yu et al. Polymer Chemistry 6(9) (2015) 1527-1532). Our reaction proceeded at 36° C. to approximate body temperature; higher temperatures could promote the Michael addition pathway further. To determine the influence of the thiol oxidation and Michael addition, the storage modulus was measured after 1 day, and it corresponded with the storage modulus change of the mixture of MA-HA and SH-HA without RFP (FIG. 15). From the result, we confirmed that the gelation of mixture of MA-HA and SH-HA without external triggering by light or RFP has a slow reaction rate and yields gels with low modulus. Of note, BL or UV light exposure in the presence of RFP does not trigger gelation of MA-HA alone in the absence of SH-HA. This indicates, as expected, that photo-initiation by RFP does not generate free radicals to catalyze polymerization of methacrylate groups. Furthermore, BL or UV light exposure does not trigger gelation of HA-SH either, indicating that the photo-reaction is not sufficiently oxidizing enough to form disulfide bonds. Thus, the light-induced activation of RFP in our system specifically targets the thiol-ene reaction.

The delayed gelation of light-induced thiol-ene reaction is unique potentially useful for clinical situations. For example, due to the delay in complete gelation after light exposure, the precursor solution can be irradiated prior to being applied to the patient's tissue surface, with the gel then forming in situ. Thus, the HA gel layer can be fabricated on the tissue surface without direct exposure of the tissue to light. The absence of light irradiation during treatment can reduce potential harmfulness, especially for light-sensitive tissue such as an eye.

Figure 16:
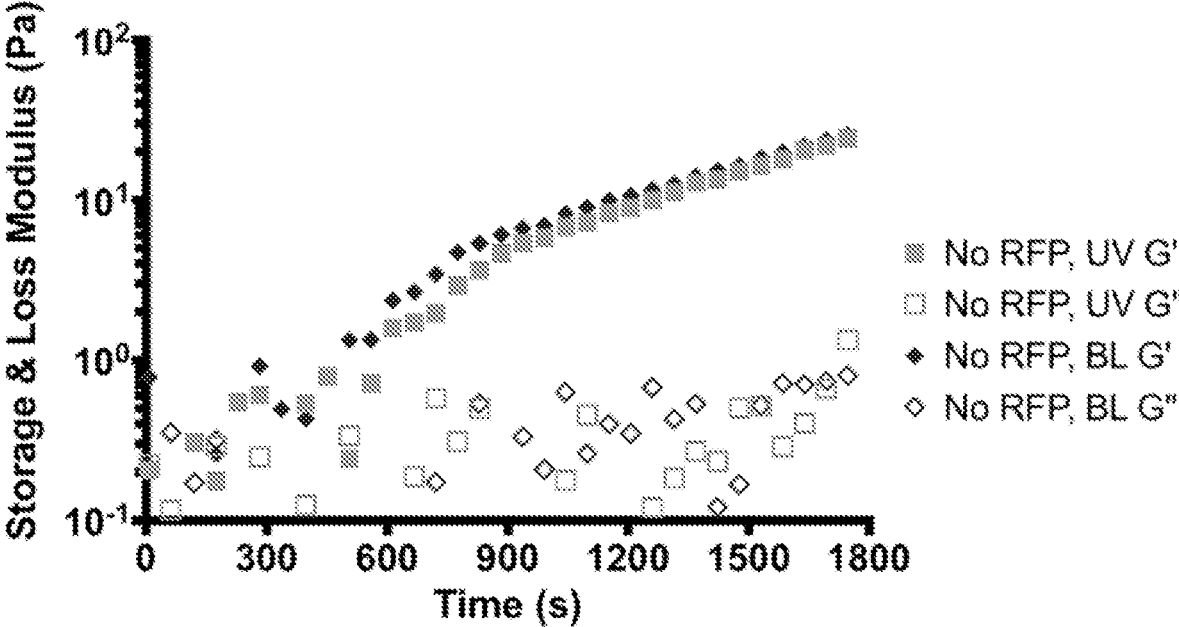
FIG. 16 shows dynamic moduli as a function of time of mixture of SH-HA and MA-HA without RFP.

A previous study introduced riboflavin as an initiator for thiol-norbornene reaction for synthetic hydrogel formation, but the gel formations were quick and required light until completion of the reaction (Batchelor et al. Polymer Chemistry 8(6) (2017) 980-984). The difference is due to the alkene group. The photo-initiated thiol-methacrylate reaction is relatively slow compared to thiol-norbornene (Northrop et al. J. Am. Chem. Soc. 134(33) (2012) 13804-13817), making the light-induced thiol-methacrylate reaction potentially more convenient from a handling perspective. To evaluate the effect of light without RFP on gelation, the mixture solution of MA-HA and SH-HA was exposed to UV or BL, and the dynamic moduli were found to be the same as the unexposed mixtures (FIG. 16). This indicates that there was no additional crosslinking reaction without RFP despite light exposure, and this result means that RFP has an important and essential role in the light-induced thiol-ene reaction.

3.3. Transparency of HA Gels by Light-Induced Thiol-Ene Reaction

Figure 12A:
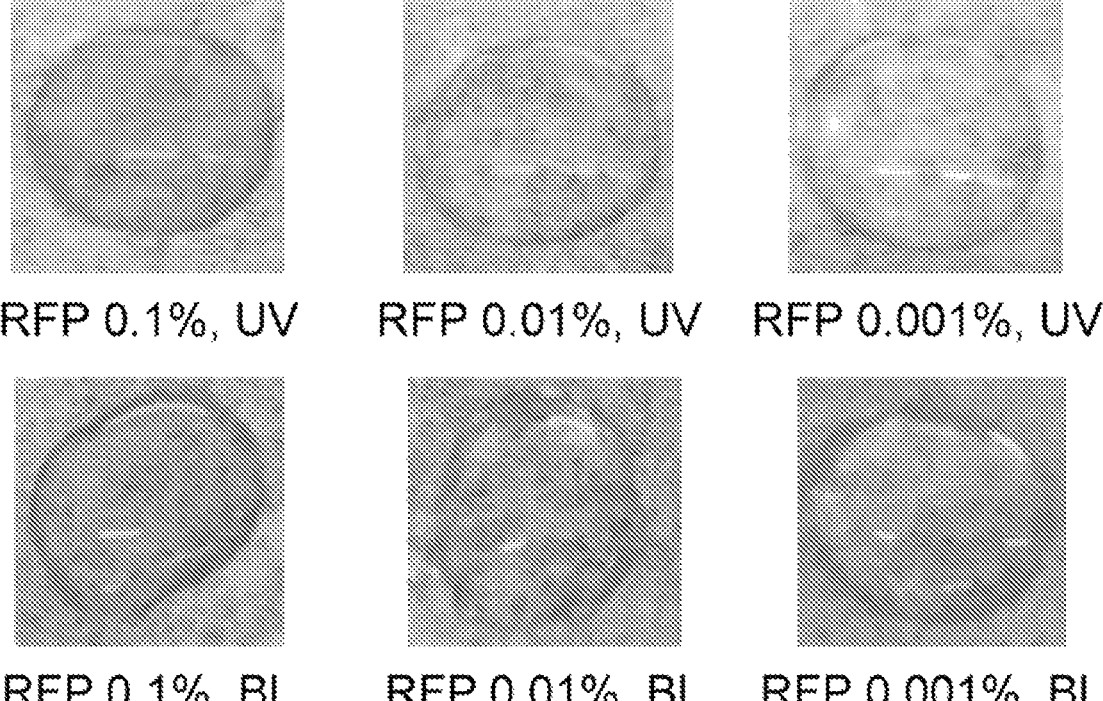
FIG. 12A shows photographic images of HA gels after light exposure with different concentration of RFP. Transmittance spectra of HA gels by (FIG. 12B) 0.01% and (FIG. 12C) 0.1% RFP with time.
Figure 12B:
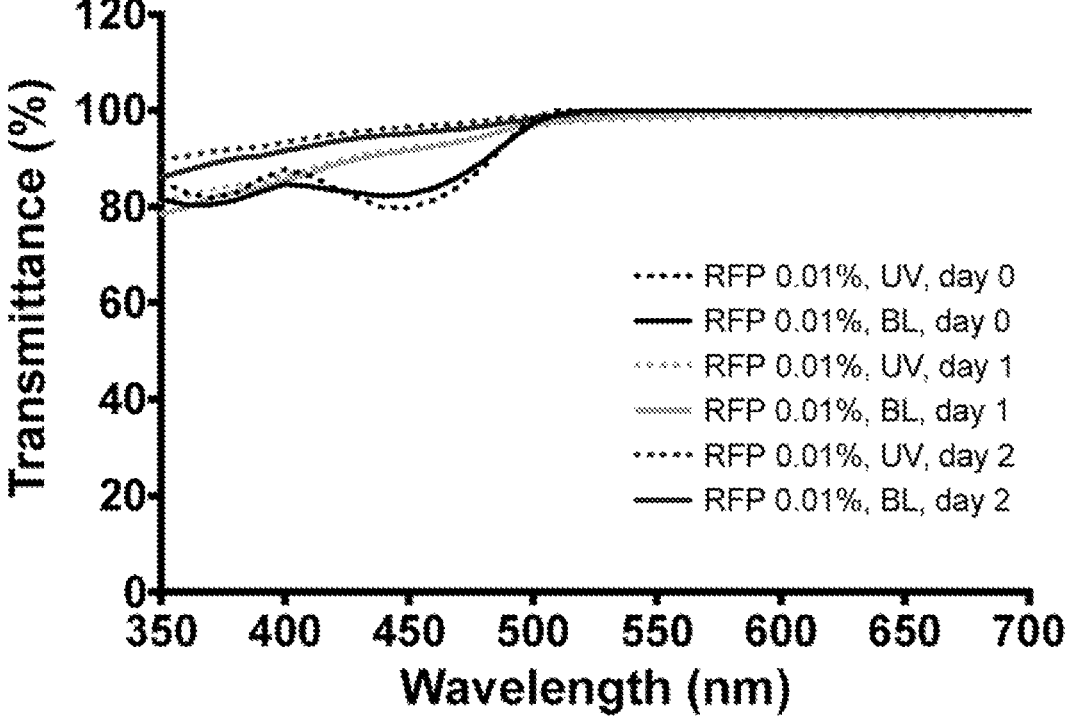
Figure 12C:
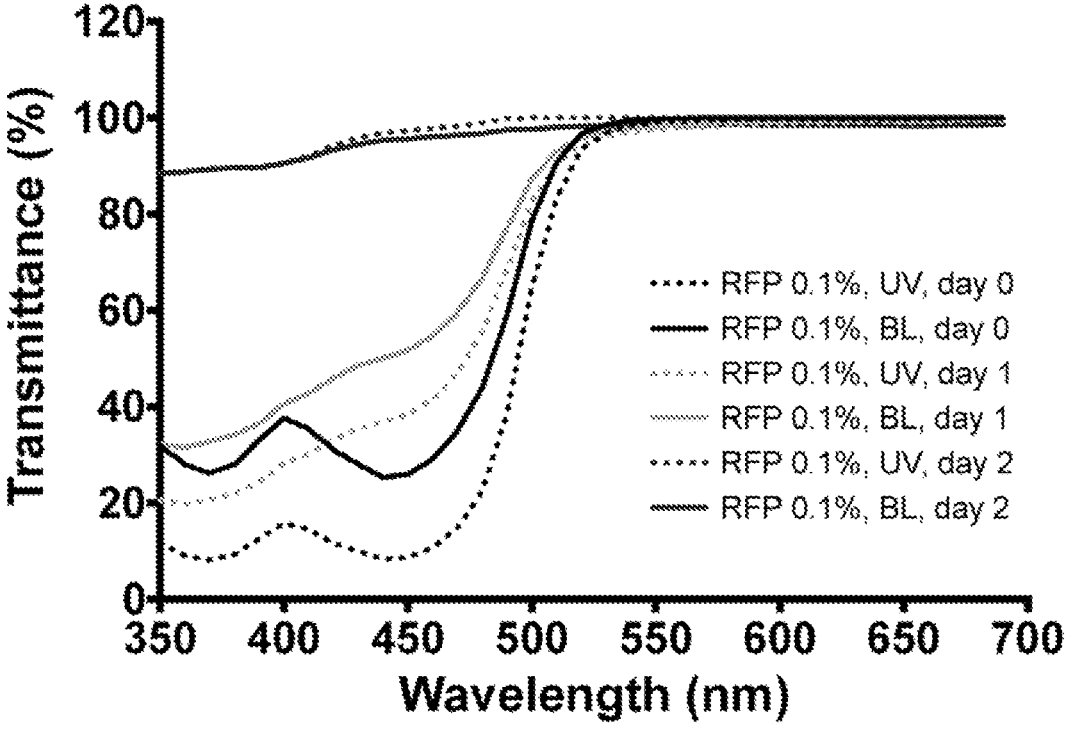

The transparency of the gel was measured by evaluation of transmittance after gelation. The gels were fabricated in 96 well plate at 100 µl volumes. The resultant gels were slightly yellow in color, and transmittance was determined by the concentration of RFP (FIG. 12A). RFP 0.001% contained HA gels were macroscopically clear. For the HA gel by 0.01% RFP, both UV and BL-induced HA gels had similar transmittance spectra, and they were over 80% in the visible wavelength range (FIG. 12B). The HA hydrogel containing 0.1% RFP showed about 20% transmittance under 480 nm of wavelength region, but transparency became increased in 2 days after the gel incubation in the aqueous solution (FIG. 12C). The transparency increase with time indicates that the RFP was able to diffuse out from the HA gel matrices.

The transmittance spectra corresponded with the concentration of RFP, and there was significant decrease between 0.01% and 0.1% RFP from about 80% to 20% in the visible wavelength range. The sharp decrease of transmittance supports that the high concentration of RFP interferes the thiol-ene reaction initiation by the deterioration of light penetration.

3.4. Degradation of HA Gels and BSA Release

We measured the degradation of HA and release of bovine serum albumin (BSA) from the gel matrices (FIG. 13). The gels were fabricated in 24 well plate, and PBS solution was added, and then the incubation solution was collected and refreshed at certain day. For evaluation of HA degradation, HA in the collected solution was quantified using a dimethylmethylene blue (DMMB) assay. The washing solution at day 0 contained little HA in the cases of both UV and BL photo-crosslinking (UV: 4.41±1.10%, BL: 6.09±0.61%), suggesting that 95% of HA molecules participated in the gel formation (FIG. 13A). Both HA gels were degraded to half their mass in about 2-3 days. There was no statistical difference between gels made by UV and BL, but the BL-induced gel exhibited slightly faster degradation rate than the UV-induced gel. Most of the HA was degraded within 12 days, at which point the HA degradation rate was markedly reduced for both gels. When we evaluated the HA degradation from the gel which was fabricated with 0.001% RFP, the washing solution at day 0 contained 50.29±4.46 and 55.98±2.78% for UV and BL, respectively (FIG. 13B). These gels were completely degraded within 2-3 days, indicating that the low RFP concentration was not sufficient to support the thiol-ene reaction for hydrogel network crosslinking.

Figure 13A:
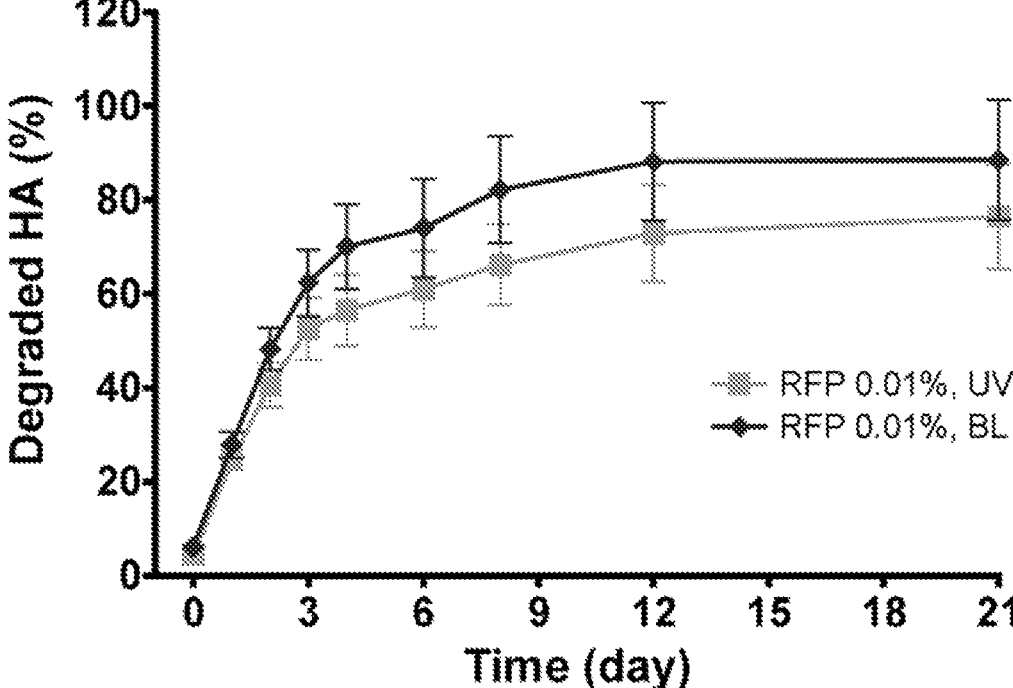
FIGS. 13A-13D show the degradation profiles of HA gels by (FIG. 13A) 0.01%, (FIG. 13B) 0.001% and 0.1% RFP. The BSA release profiles of HA gels by (FIG. 13C) 0.01%, (FIG. 13D) 0.001% and 0.1% RFP.
Figure 13B:
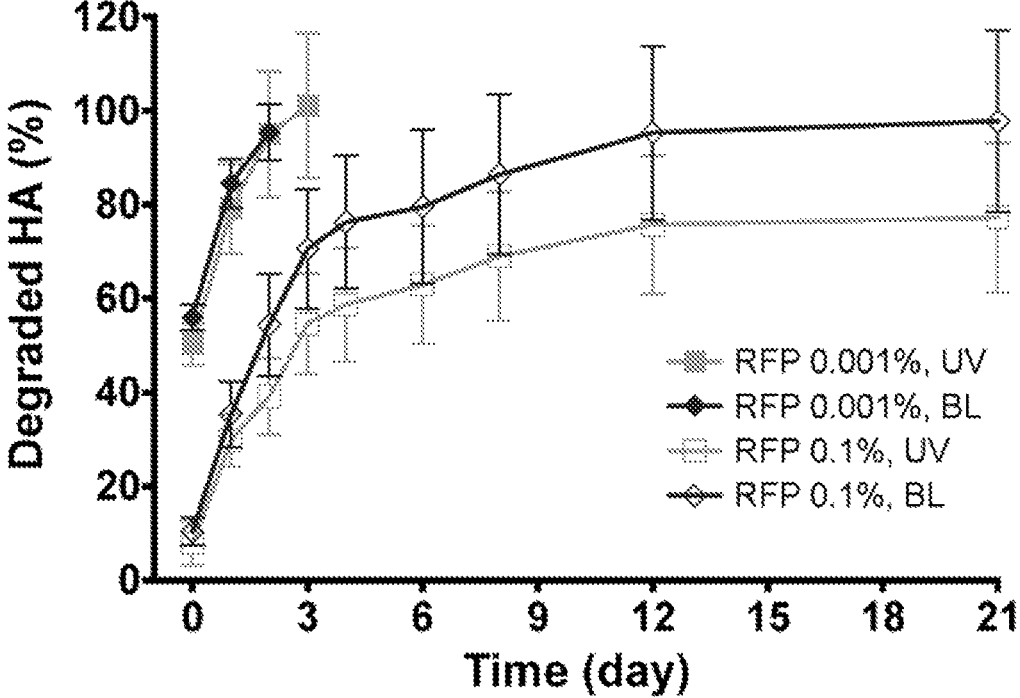

From the HA degradation results, the HA gels initiated by 0.01% and 0.1% RFP formed completely. The amount of HA that participated in the formation of gel matrix was over 90% for both concentrations of 0.01% and 0.1% RFP. On the other hand, 0.001% RFP showed similar dynamic modulus curves with 0.01% RFP (FIG. 11F), but the gels formed only partially. Almost half of HA was not included hydrogel reaction, and the HA molecules were detected in the rinsing solution (FIG. 13B). The 0.001% RFP concentration was not enough to initiate the thiol-ene reaction of MA-HA and SH-HA.

Figure 13C:
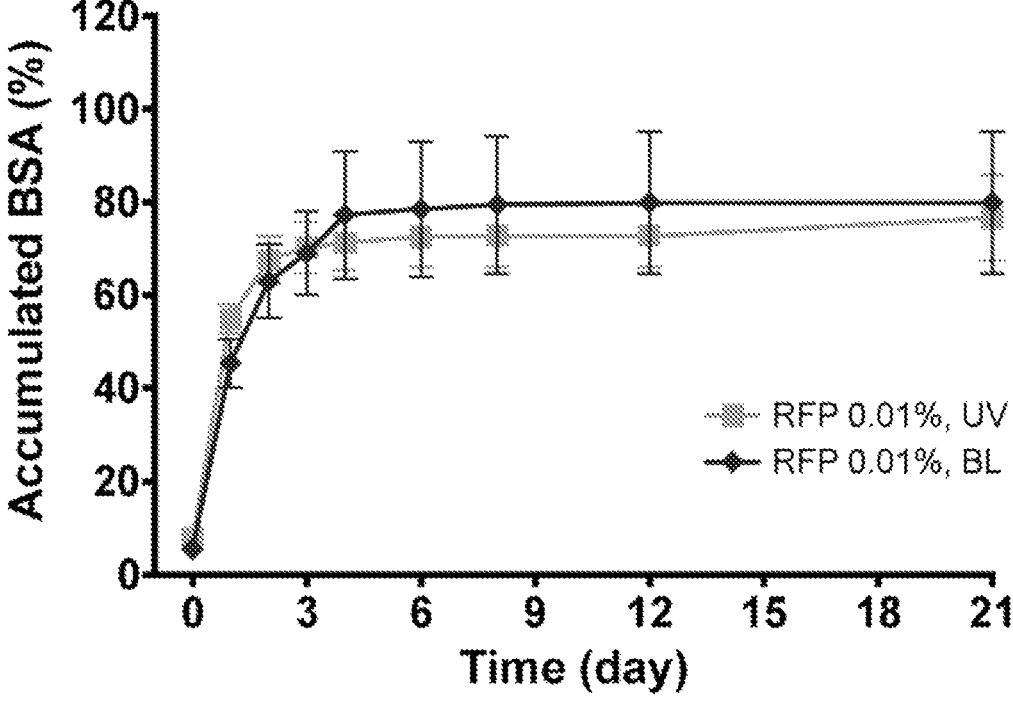
Figure 13D:
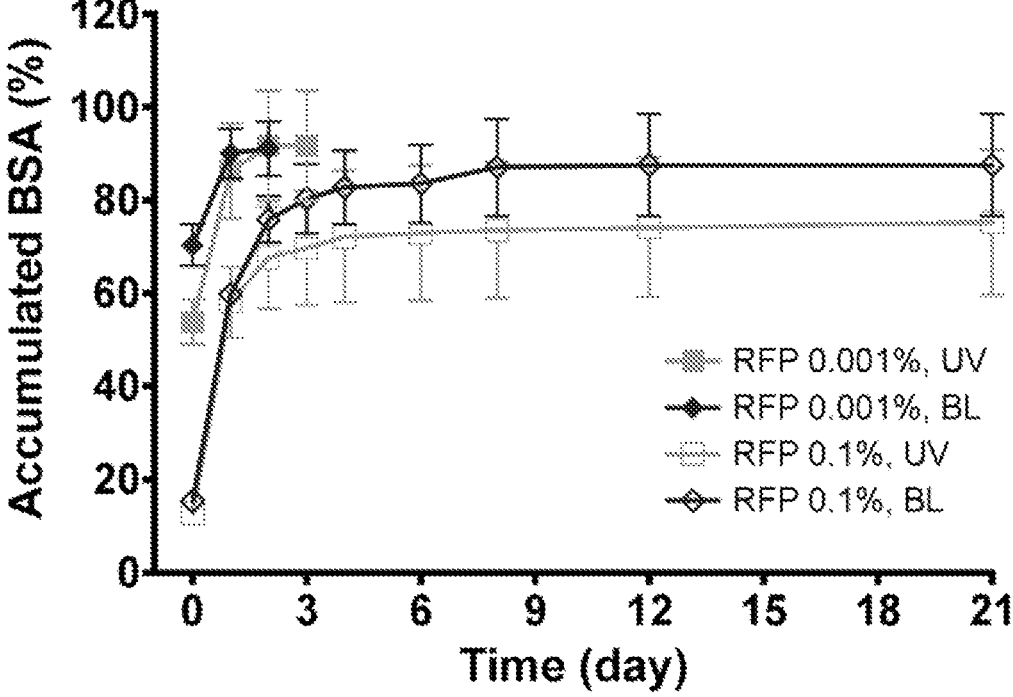

The release profile of BSA from the HA gel was measured by quantification of protein in the collected aqueous solution. The release of BSA generally followed the HA degradation profile, with greater release as the gel was further degraded (FIG. 13C). The BSA was well-incorporated into the HA gel because the washing solution at day 0 contained 7.74±0.48 and 5.59±0.41% for UV and BL exposure, respectively. On the other hand, at the 0.001% RFP, BSA release profiles corresponded with HA degradation. As more than 50% HA did not form a gel, more than 50% of BSA was in the washing solution at day 0 without being encapsulated in HA gel (FIG. 13D). Most of the encapsulated BSA was released within 4 days in all cases, and HA gels with 0.1% RFP showed similar release profile those with 0.01% RFP (FIG. 13D).

BSA was used as a model protein, and the release profile was evaluated in this study. The BSA was encapsulated in the HA gel matrix, and the protein was released from the matrix with HA degradation. The protein release profiles were matched with HA degradation curves, so the main driving force for release was matrix degradation rather than diffusion.

Also, the results of this study showed that BL exhibits a similar ability to UV for the purposes of HA gelation via the thiol-ene reaction. Although BL and UV are interchangeable for initiation of the thiol-ene reaction, the BL provides potentially a safer energy source than UV, and may be preferable when biomolecules such as proteins, or living cells are being irradiated simultaneously. Thus, the substitution of UV with BL may be advantageous for certain biomedical applications of HA gels.

3.5. Corneal Fibroblast Viability

Figure 14A:
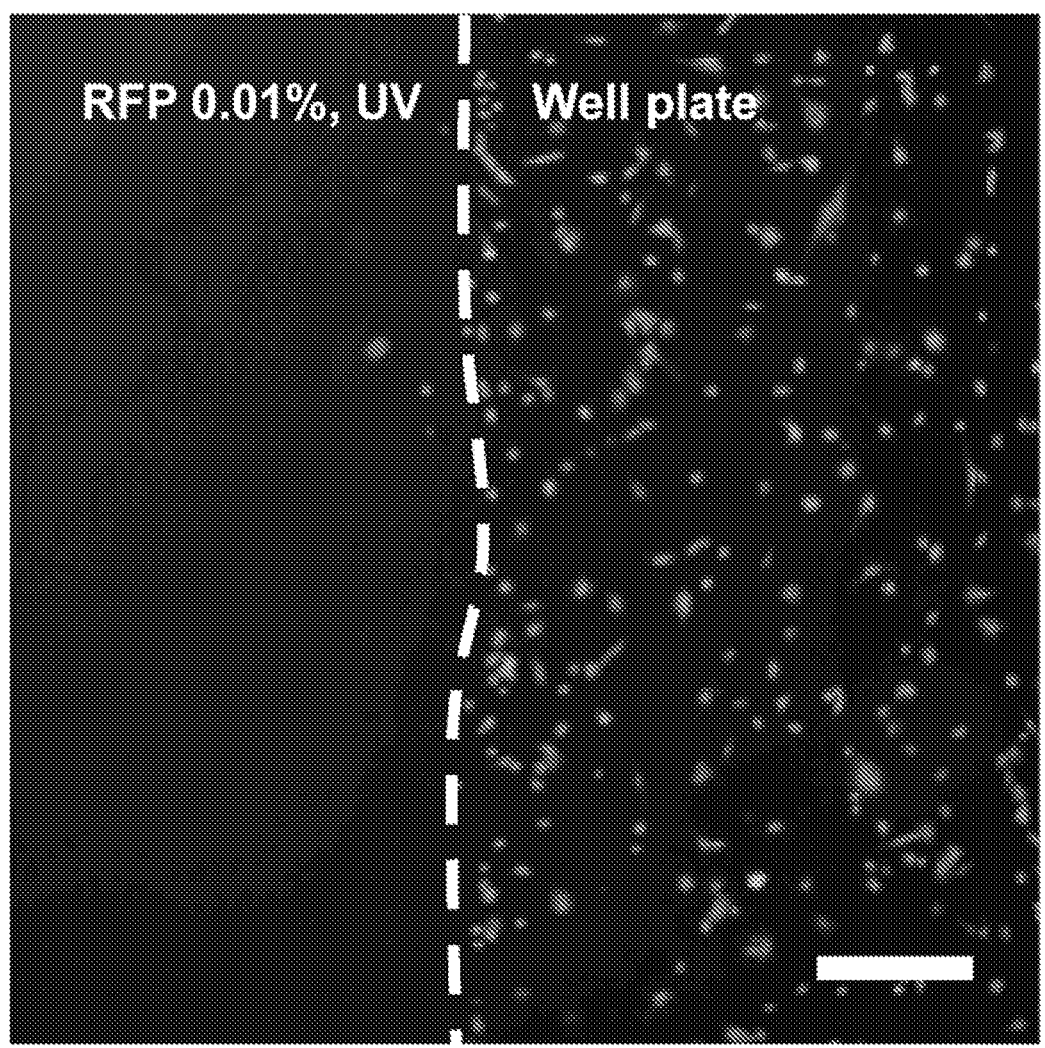
FIGS. 14A and 14B show fluorescence images of corneal fibroblasts LIVE/DEAD assay. The cells cultured with HA gels initiated by (FIG. 14A) UV and (FIG. 14B) BL. Scale bars represent 500 μm.
Figure 14B:
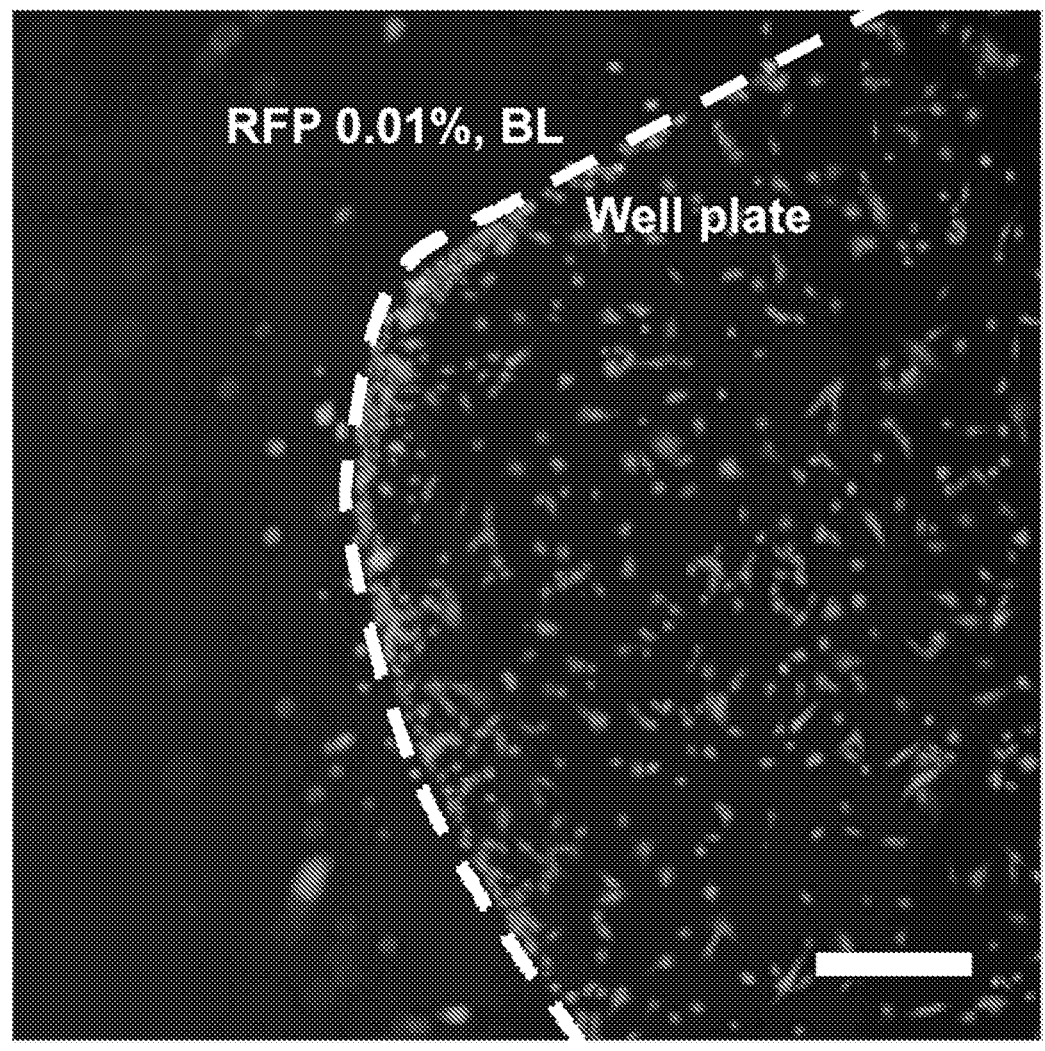

The cytocompatibility of HA precursor solution and gels were evaluated by corneal fibroblast viability. The concentration of RFP was fixed as 0.01% for cell viability test. After light exposure, the viscous HA solutions were transferred to the well plates, and the solution formed gel. The cells were cultured with HA gels overnight and there were no cytotoxic effects of HA gels initiated by both UV and BL to the cells (FIG. 14). The cells did not adhere on the HA gel surface, but the cells on the well plate adhered and remained viable. Moreover, there was no cytotoxic effects due to contact between the cells and the HA gel, indicated by the viability of the cells at the gel interface.

HA is widely used biocompatible biomaterial, and the conjugation of the thiol and methacrylate groups did not appear to affect the biocompatibility of HA.

A light-induced thiol-ene reaction could be used to rapidly form an HA gel and encapsulate proteins that could be released from the matrix on the order of days. We learned that BL is sufficient to trigger the thiol-ene reaction, but that this reaction proceeds over several minutes rather than going to completion during the light exposure interval. BL was as or more effective than UV at activating the thiol-ene reaction with RFP. For several minutes immediately after light exposure, the solution takes on a viscous and flowable state, which lends the material to topical application or injection. It then exhibits a steep modulus increase. Moreover, the resultant gel is transparent making it potentially suitable for ophthalmic applications. The fabrication procedure and resultant hydrogel had excellent cytocompatibility. The ability to crosslink HA using RFP, a known biocompatible photo-activator, with exposure to visible light, makes this system promising for potential therapeutic applications, in particular ones where in situ gel formation is desirable.

While the preferred embodiments of the invention have been illustrated and described, it will be appreciated that various changes can be made therein without departing from the spirit and scope of the invention.

What is claimed is:

1. A method of accelerating wound healing and reducing neovascularization and scar formation, in damaged tissue in a subject, the method comprising:
    a) collecting a bone marrow-derived mesenchymal stem cell (MSC) secretome from a mesenchymal stem cell;
    b) mixing the bone marrow-derived mesenchymal stem cell (MSC) secretome from the stem cell with a solution comprising at least one biocompatible polymer or biopolymer to form a mixture; wherein said at least one biocompatible polymer or biopolymer comprises a mixture of hyaluronic acid and chondroitin sulfate; and
    c) applying the mixture to the damaged tissue, wherein the bone marrow-derived mesenchymal stem cell (MSC) secretome from the stem cell accelerates healing at or under the surface of the damaged tissue; wherein the damaged tissue is ocular tissue, wherein the ocular tissue is corneal or stromal tissue;
    and wherein the bone marrow-derived MSC secretome reduces neovascularization and scar formation in the damaged tissue.

2. The method of claim 1, wherein said at least one biocompatible polymer or biopolymer encapsulates the bone marrow-derived MSC secretome in step b).

3. The method of claim 1, wherein said at least one biocompatible polymer or biopolymer is adherent to tissue.

4. The method of claim 1, wherein said at least one biocompatible polymer or biopolymer forms a hydrogel encapsulating the bone marrow-derived MSC secretome in step b).

5. The method of claim 1, wherein the subject is human.

6. The method of claim 1, further comprising preparing the damaged tissue prior to treating the subject by exfoliation or debridement of fibrotic or necrotic tissue.

7. The method of claim 1, further comprising administering one or more therapeutic agents to the subject.

8. The method of claim 7, wherein the one or more therapeutic agents are selected from the group consisting of an analgesic agent, an anti-inflammatory agent, and an anesthetic.

9. The method of claim 1, wherein step c) is repeated for multiple cycles—for a time period sufficient to effect at least a partial healing of the damaged tissue, or wherein step c) is repeated for multiple cycles—for a time period sufficient to effect a complete healing of the damaged tissue.

10. The method of claim 1, wherein damage to the ocular tissue is caused by a chemical burn, severe dry eye, keratoconjunctivitis sicca, Sjogren's syndrome, ocular graft-versus-host disease, ocular cicatricial pemphigoid, Stevens-Johnson syndrome, physical trauma, neurotrophic keratopathy, a recurrent corneal erosion, a corneal ulcer, exposure keratopathy, retinal disease or degeneration, or optic nerve damage or degeneration.

11. The method of claim 4, wherein the hydrogel molds to the contours of the ocular tissue surface.

* * * * *